US012742772B2

(12) United States Patent
Krishnan et al.

(10) Patent No.: US 12,742,772 B2
(45) Date of Patent: Sep. 22, 2026

(54) DNA-BASED VOLTMETER FOR ORGANELLES

(71) Applicant: The University of Chicago, Chicago, IL (US)

(72) Inventors: Yamuna Krishnan, Chicago, IL (US); Aneesh Tazhe Veetil, Chicago, IL (US); Anand Saminathan, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 997 days.

(21) Appl. No.: 17/758,608

(22) PCT Filed: Jan. 15, 2021

(86) PCT No.: PCT/US2021/013745
§ 371 (c)(1),
(2) Date: Jul. 11, 2022

(87) PCT Pub. No.: WO2021/194613
PCT Pub. Date: Sep. 30, 2021

(65) Prior Publication Data

US 2023/0324370 A1 Oct. 12, 2023

Related U.S. Application Data

(60) Provisional application No. 62/961,615, filed on Jan. 15, 2020.

(51) Int. Cl.
*G01N 33/50* (2006.01)
*G01N 33/58* (2006.01)

(52) U.S. Cl.
CPC ....... *G01N 33/5076* (2013.01); *G01N 33/582* (2013.01)

(58) Field of Classification Search
None
See application file for complete search history.

(56) References Cited

U.S. PATENT DOCUMENTS

| | | | | |
|---|---|---|---|---|
| 11,136,618 | B2 | 10/2021 | Krishnan et al. | |
| 2017/0101669 | A1* | 4/2017 | Krishnan ............. | C12Q 1/6825 |
| 2021/0096129 | A1 | 4/2021 | Krishnan et al. | |
| 2022/0011325 | A1 | 1/2022 | Krishnan et al. | |
| 2023/0055931 | A1 | 2/2023 | Krishnan et al. | |

FOREIGN PATENT DOCUMENTS

| | | | |
|---|---|---|---|
| WO | 2016-187284 | A1 | 11/2016 |
| WO | 2018-191561 | A1 | 10/2018 |
| WO | 2020-117701 | A1 | 6/2020 |
| WO | 2021-119448 | A1 | 6/2021 |
| WO | 2022-051724 | A2 | 3/2022 |

OTHER PUBLICATIONS

Hemmig et al. "Optical voltage sensing using DNA origami." Nano letters 18.3 (2018): 1962-1971 (Year: 2018).*
Hernández-Ainsa et al. "Voltage-dependent properties of DNA origami nanopores." Nano letters 14.3 (2014): 1270-1274 (Year: 2014).*
Waiczies et al. "Anchoring dipalmitoyl phosphoethanolamine to nanoparticles boosts cellular uptake and fluorine-19 magnetic resonance signal." Scientific reports 5.1 (2015): 8427. (Year: 2015).*
Zhang et al. "Choosing the right fluorophore for single-molecule fluorescence studies in a lipid environment." Biochimica et Biophysica Acta (BBA)-Biomembranes 1859.7 (2017): 1242-1253. (Year: 2017).*
Bradley et al., "Effects of Filipin, Digitonin, and Polymyxin B on Plasma Membrane of Ram Spermatozoa—An EM Study", Archives of Andrology, 1980, vol. 4, pp. 195-204.
Atakpa et al., "IP3 Receptors Preferentially Associate with ER-Lysosome Contact Sites and Selectively Deliver Ca2+ to Lysosomes", Cell Rep, 2018, vol. 25, pp. 3180-3193.
Cain et al., "Regulation of Endocytic pH by the Na+,K+-ATPase in Living Cells", Proc. Natl. Acad. Sci. USA, 1989, vol. 36, pp. 544-548.
Cang et al. "mTOR Regulates Lysosomal ATP-Sensitive Two-Pore Na(+) Channels to Adapt to Metabolic State", Cell, 2013, vol. 152, pp. 778-790.
Cang et al., "TMEM175 is an Organelle K(+) Channel Regulating Lysosomal Function", Cell, 2015, vol. 162, pp. 1101-1112.
Cao et al., "BK Channels Alleviate Lysosomal Storage Diseases by Providing Positive Feedback Regulation of Lysosomal Ca2+ Release", Dev. Cell, 2015, vol. 33, pp. 427-441.
Chakraborty et al., "High Lumenal Chloride in the Lysosome is Critical for Lysosome Function", Elife, 2017, vol. 6, pp. 1-21.
Crider et al., "Bafilomycin Inhibits Proton Flow Through the H+ Channel of Vacuolar Proton Pumps", J. Biol. Chem., 1994, vol. 269, No. 26, pp. 17379-17381.
Farsi et al., "Single-Vesicle Imaging Reveals Different Transport Mechanisms Between Glutamatergic and GABAergic Vesicles", Science, 2016, vol. 351, No. 6276, pp. 981-984.
Gagescu et al., "The Recycling Endosome of Madin-Darby Canine Kidney Cells is a Mildly Acidic Compartment Rich in Raft Components", Mol. Biol. Cell, 2000, vol. 11, pp. 2775-2791.
Gonin et al., "Cyclic AMP Increases Cell Surface Expression of Functional Na,K-ATPase Units in Mammalian Cortical Collecting Duct Principal Cells", Mol. Biol. Cell, 2001, vol. 13, pp. 255-264.
Grimm et al, "Whole-Cell Patch-Clamp Recordings for Electrophysiological Determination of Ion Selectivity in Channelrhodopsins", J. Vis. Exp., 2017, vol. 123, pp. 1-8.

(Continued)

*Primary Examiner* — Emily A Cordas
(74) *Attorney, Agent, or Firm* — McDonnell Boehnen Hulbert & Berghoff LLP

(57) ABSTRACT

This disclosure relates to methods for determining membrane potential across membranes of organelles and cells. More particularly, this disclosure relates to nucleic add complexes comprising a voltage-sensing fluorophore conjugated to one single-stranded nucleic acid molecule and methods for using such nucleic acid complexes in determining the membrane potential.

19 Claims, 23 Drawing Sheets

Specification includes a Sequence Listing.

(56) References Cited

OTHER PUBLICATIONS

Han et al., "Cell-Permeable Organic Fluorescent Probes for Live-Cell Long-Term Super-Resolution Imaging Reveal Lysosome-Mitochondrion Interactions", Nature Commun, 2017, vol. 8, pp. 1-9.
Hockey et al., "Dysregulation of Lysosomal Morphology by Pathogenic LRRK2 is Corrected by TPC2 Inhibition", J. Cell Sci., 2015, vol. 128, pp. 232-238.
Hover et al., "Bunyavirus Requirement for Endosomal K+ Reveals New Roles of Cellular Ion Channels During Infection", PLOS Pathogens, 2018, vol. 14, No. 1, pp. 1-21.
Johnson et al., "Protonmotive Force and Catecholamine Transport in Isolated Chromaffin Granules", J. Biol. Chem., 1979, vol. 254, No. 10, pp. 3750-3760.
Koivusalo et al., "In situ Measurement of the Electrical Potential Across the Lysosomal Membrane Using FRET", Traffic, 2011, vol. 12, pp. 972-982.
Liang et al., "Identification of a Pool of Non-Pumping Na/K-ATPase", J. Biol. Chem., 2007, vol. 282, No. 14, pp. 10585-10593.
López-Sanjurjo et al., "Lysosomes Shape Ins(1,4,5)P3-evoked Ca2+ signals by Selectively Sequestering Ca2+ Released from the Endoplasmic Reticulum", J. Cell Sci., 2013, vol. 126, pp. 289-300.
Miller et al., "Optically Monitoring Voltage in Neurons by Photo-Induced Electron Transfer Through Molecular Wires", Proc. Natl. Acad. Sci. USA, 2012, vol. 109, No. 6, pp. 2114-2119.
Numata et al., "Molecular Cloning and Characterization of a Novel (Na+, K+)/H+ Exchanger Localized to the Trans-Golgi Network", J. Biol. Chem., 2001, vol. 276, No. 20, pp. 17387-17394.
Rosenfeld et al., "Lysosome Proteins are Redistributed During Expression of a GTP-hydrolysis-defective rab5a", J. Cell Sci., 2001, vol. 114, pp. 4499-4508.
Russa et al. "Microtubule Remodeling Mediates the Inhibition of Store-Operated Calcium Entry (SOCE) During Mitosis In COS-7 Cells", Arch Histol Cytol, 2008, vol. 71, No. 4, pp. 249-263.
Schapiro et al., "Determinants of the pH of the Golgi Complex", J. Biol. Chem., 2000, vol. 275, No. 28, pp. 21025-21032.
Sun, et al., A Negative Feedback regulation of MTORC1 activity by the lysosomal Ca2+ channel MCOLN1 (mucolipin 1) using a CALM (calmodulin)-dependent mechanism. Autophagy 14(1), 38-52 (2018).
Surana, S., Bhat, J. M., Koushika, S. P. & Krishnan, Y. "An autonomous DNA nanomachine maps spatiotemporal pH changes in a multicellular living organism," Nature Commun, 2011, vol. 2, No. 340, pp. 1-7.
Vercesi et al., "Digitonin Permeabilization does not Affect Mitochondrial Function and Allows the Determination of the Mitochondrial Membrane Potential of Trypanosoma Cruzi in situ", J. Biol. Chem., 1991, vol. 266, No. 22, pp. 14431-14434.
Vonderheit et al., "Rab7 Associates with Early Endosomes to Mediate Sorting and Transport of Semliki Forest Virus to Late Endosomes", PLoS Biology, 2005, vol. 3, No. 7, pp. 1225-1238.
Zhang et al, "A Mechanically Driven Form of Kirigami as a Route to 3D Mesostructures in Micro/Nanomembranes", Proc. Natl. Acad. Sci. USA, 2015, vol. 112, No. 38, pp. 11757-11764.
Van Galen, J. et al. "Sphingomyelin homeostasis is required to form functional enzymatic domains at the trans-Golgi network," J. Cell Biol., 2014, vol. 206(5), 609-618.
Form PCT/ISA/201, PCT International Search Report issued in International Application No. PCT/US2021/013745 dated Nov. 11, 2021.
Form PCT/ISA/237, Written Opinion of the International Searching Authority issued in International Application No. PCT/US2021/013745 dated Nov. 11, 2021.
Huang, Yi-Lin et al., "A Photostable Silicon Rhodamine Platform for Optical Voltage Sensing," J. Am Chem Soc. (2015) vol. 137, No. 33, pp. 10767-10776.
Kulkarni, Rishikesh U., et al., "Voltage-sensitive Rhodol with Enhanced Two-photon Brightness," PNAS (2017) vol. 114, No. 11, pp. 2813-2818.
Miller, Evan W., et al. "Optically Monitoring Voltage in Neurons by Photo-induced Electron Transfer Through Molecular Wires," PNAS (2012) vol. 109, No. 6, pp. 2114-2119.
Hemmig, Elisa A., et al., "Optical Voltage Sensing Using DNA Origami," Nano Lett (2018) vol. 18, No. 3, pp. 1962-1971.
Saminathan, Anand et al., "A DNA-based Voltmeler for Organelles," Nature Biotechnology, 2019, vol. 16, pp. 1-19.
Chakraborty et al., "Nucleic Acid Based Nanodevices in Biological Imaging", Annu. Rev. Biochem., 2016, vol. 85, pp. 349-373.
Bhatia et al., "Icosahedral DNA Nanocapsules by Modular Assembly", Angew. Chem. Int. Ed. Engl., 2009, vol. 121, pp. 4198-4201.
Bhatia et al., "Quantum Dot-Loaded Monofunctionalized DNA Icosahedra for Single-Particle Tracking of Endocytic Pathways", Nat. Nanotechnol., 2016, vol. 11, pp. 1112-1119.
Dan et al., "DNA Nanodevices Map Enzymatic Activity in Organelles", Nat. Nanotechnol., 2019, vol. 14, No. 3, pp. 252-259.
Dong et al., "The Type IV Mucolipidosis-Associated Protein TRPML1 is an Endolysosomal Iron Release Channel", Nature, 2008, vol. 455, pp. 992-996.
Douglas et al., "Influence of the Ionic Environment on the Membrane Potential of Adrenal Chromaffin Cells and on the Depolarizing Effect of Acetylcholine", J. Physiol., 1967, vol. 191, pp. 107-121.
Famulok et al., "Functional Aptamers and Aptazymes in Biotechnology, Diagnostics, and Therapy", Chem. Rev., 2007, vol. 107, No. 9, pp. 3715-3743.
Krishnan et al., "Designer Nucleic Acids to Probe and Program the Cell", Trends in Cell Biology, 2012, pp. 1-10.
Leung et al., "A DNA Nanomachine Chemically Resolves Lysosomes in Live Cells", Nat. Nanotechnol., 2019, vol. 14, pp. 176-183.
Lee et al., "BK Channel Activation: Structural and Functional Insights", Trends Neurosci., 2010, vol. 33, pp. 415-423.
Lloyd-Evans et al., "Endolysosomal Calcium Regulation and Disease", Biochem. Soc. Trans., 2010, vol. 38, No. 6, pp. 1458-1464.
Magadán et al., "Rab22a Regulates the Sorting of Transferrin to Recycling Endosomes", Mol. Cell. Biol., 2006, vol. 26, No. 7, pp. 2595-2614.
Miller et al, "Small Molecule Fluorescent Voltage Indicators for Studying Membrane Potential", Curr. Opin. Chem. Biol., 2016, vol. 33, pp. 74-80.
Modi et al., "A DNA Nanomachine that Maps Spatial and Temporal pH Changes Inside Living Cells", Nat. Nanotechnol., 2009, vol. 4, pp. 325-330.
Modi et al., "Two DNA Nanomachines Map pH Changes Along Intersecting Endocytic Pathways Inside the Same Cell", Nat. Nanotechnol., 2013, vol. 8, pp. 459-467.
Modi et al, Recombinant Antibody Mediated Delivery of Organelle-Specific DNA pH Sensors Along Endocytic Pathways:, Nanoscale, 2014, vol. 6, pp. 1144-1152.
Mousavi et al., "Glutamate Receptor-Like Genes Mediate Leaf-to-Leaf Wound Signalling" Nature, 2013, vol. 500, pp. 422-426.
Narayanaswamy et al., "A pH-Correctable, DNA-Based Fluorescent Reporter for Organellar Calcium", Nat. Methods, 2019, vol. 16, No. 1, pp. 95-102.
Patel et al., "Scavenger Receptors Mediate Cellular Uptake of Polyvalent Oligonucleotide-Functionalized Gold Nanoparticles", Bioconjug Chem., 2010, vol. 21, No. 12, pp. 2250-2256.
Prindle et al., "Ion Channels Enable Electrical Communication in Bacterial Communities", Nature, 2015, vol. 527, pp. 59-63.
Raffaello et al., "Calcium at the Center of Cell Signaling: Interplay between Endoplasmic Reticulum, Mitochondria, and Lysosomes", Trends Biochem. Sci., 2016, vol. 41, No. 12, pp. 1035-1049.
Saha et al., "A pH-Independent DNA Nanodevice for Quantifying Chloride Transport in Organelles of Living Cells", Nat. Nanotechnol., 2015, vol. 10, pp. 645-651.
Schindelin et al., "Fiji: An Open-Source Platform for Biological-Image Analysis", Nat. Methods, 2012, vol. 9, No. 7, pp. 676-682.
Van Galen, et al., "Sphingomyelin Homeostasis is Required to Form Functional Enzymatic Domains at the Trans-Golgi Network", J. Cell Biol., 2014, vol. 206, No. 5, pp. 609-618.

(56) References Cited

OTHER PUBLICATIONS

Van Lengerich et al, "Covalent Attachment of Lipid Vesicles to a Fluid-Supported Bilayer Allows Observation of DNA-Mediated Vesicle Interactions", Langmuir, 2010, vol. 26, No. 11, pp. 8666-8672.
Xu et al., "Organellar Channels and Transporters", Cell Calcium, 2015, vol. 58, No. 1, pp. 1-10.
You et al., "DNA Probes for Monitoring Dynamic and Transient Molecular Encounters on Live Cell Membranes", Nat. Nanotechnol., 2017, vol. 12, No. 5, pp. 453-459.
Agard et al., "A Strain-Promoted [3 + 2] Azide-Alkyne Cycloaddition for Covalent Modification of Biomolecules in Living Systems", J. Am. Chem. Soc., 2004, vol. 126, pp. 15046-15047.
Alberts et al., "Ion Channels and the Electrical Properties of Membranes", NCBI Bookshelf, Molecular Biology of the Cell, 4th Edition, 2002, Retrieved from the Internet Jun. 16, 2023 as https://www.ncbi.nlm.nhi.gov/books/NBK2910/, pp. 1-21.
Chen, Lan Bo, "Mitochondrial Membrane Potential in Living Cells", Ann. Rev. Cell. Biol., 1988, vol. 4, pp. 155-181.
Click Chemistry for Biotechnology and Materials Science, 2009, DOI: 10.1002/978047074862, pp. 1-5 (Abstract Only).
Leonhardt et al., "Acid-Base Equilibria of Flurescein and 2', 7'-Dichlorofluorescrin in their Ground and Fluorescent States", The Journal of Physical Chemistry, 1971, vol. 75, No. 2, pp. 245-249.
Moore et al., "Purification and Concentration of DNA from Aqueous Solutions", Current Protocols in Molecular Biology, 2002, Chapter 2, Unit 2.1A, Supplement 59, pp. 1-10.
Nicholls et al., "Mitochondrial Membrane Potential and Neuronal Glutamate Excitotoxicity: Mortality and Millivolts", Trends Neurosci, 2000, vol. 23, No. 4, pp. 166-174.
Sabnis, R.W, Handbook of Acid-Base Indicators, 2007, 1st Edition, Description, pp. 1-2 (Abstract Only).
Schröder et al., "The Proteome of Lysosomes", Proteomics, 2010, vol. 10, pp. 4053-4076.
Whitaker et al., "Fluorescent Rhodol Derivatives: Versatile, Photostable Labels and Tracers," Analytical Biochemistry, 1992, vol. 207, pp. 267-279.
Zhao et al., "Visualizing Intercellular Tensile Forces by DNA-Based Membrane Molecular Probes", J. Am. Chem. Soc., 2017, vol. 139, pp. 18182-18185.
Zhong et al., "Lysosome Electrophysicology", Methods Cell Biol., 2015, vol. 126, pp. 197-215.
Chakraborty et al., "High Lumenal Chloride in the Lysosome is Critical for Lysosome Function", Elife, 2017, vol. 6, e28862, pp. 1-21.
Dong et al., "TRP Channels of Intracellular Membranes", J. Neurochem., 2010, vol. 113, pp. 313-328.
Fliegert et al., "Modulation of Ca2+ Entry and Plasma Membrane Potential by Human TRPM4b", FEBS J., 2007, vol. 274, pp. 704-713.
Grabe et al., "Regulation of Organelle Acidity", J. Gen. Physiol., 2001, vol. 117, pp. 329-344.
Guha et al., "Shibire Mutations Reveal Distinct Dynamin-Independent and -Dependent Endocytic Pathways in Primary Cultures of *Drosophila hemocytes*", J. Cell Sci, 2003, vol. 116, pp. 3373-338.
Helmchen et al., "Ca2+ Buffering and Action Potential-Evoked Ca2+ Signaling in Dendrites of Pyramidal Neurons", Biophysical Journal, 1996, vol. 70, pp. 1069-1081.
Jin et al., "Characterization and Application of a New Optical Probe for Membrane Lipid Domains", Biophysical Journal, 2006, vol. 90, pp. 2563-2575.
Kulkarni et al., "Voltage-Sensitive Rhodol with Enhanced Two-Photon Brightness", Proc. Natl. Acad. Sci. USA, 2017, vol. 114, No. 11, pp. 2813-2818.
Meeusen et al. "Mitochondrial Fusion Intermediates Revealed in Vitro", Science, 2004, vol. 305, pp. 1747-1752.
Mouli et al., "Frequency and Selectivity of Mitochondrial Fusion are Key to its Quality Maintenance Function", Biophys. J., 2009, vol. 96, pp. 3509-3518.
Post et al., "Class A Scavenger Receptors Mediate Cell Adhesion Via Activation of G(i/o) and Formation of Focal Adhesion Complexes", J. Lipid Res., 2002, vol. 43, pp. 1829-1836.
Ramzan et al., "Mitochondrial Respiration and Membrane Potential are Regulated by the Allosteric ATP-Inhibition of Cytochrome c Oxidase", Biochim. Biophys. Acta, 2010, vol. 1797, pp. 1672-1680.
Rubaiy, H. N., "A Short Guide to Electrophysiology and Ion Channels", J. Pharm. Pharm. Sci., 2017, vol. 20, pp. 48-67.
Santana et al., "How Does the Shape of the Cardiac Action Potential Control Calcium Signaling and Contraction in the Heart?", J. Mol. Cell Cardiol., 2010, vol. 49, pp. 901-903.
Shattock et al., "Measurement of Na(+)-K+ Pump Current in Isolated Rabbit Ventricular Myocytes Using the Whole-Cell Voltage-Clamp Technique. Inhibition of the Pump by Oxidant Stress", Circ. Res., 1993, vol. 72, pp. 91-101.
Srivastava et al., "Intracellular pH Sensors: Design Principles and Functional Significance", Physiology, 2007, vol. 22, pp. 30-39.
Surana et al., "An Autonomous DNA Nanomachine Maps Spatiotemporal pH Changes in a Multicellular Living Organism", Nature Communication, 2011, vol. 2, No. 340, pp. 1-6.
Wang et al., "A Voltage-Dependent K+ Channel in the Lysosome is Required for Refilling Lysosomal Ca2+ Stores", J. Cell Biol., 2017, vol. 216, No. 6, pp. 1715-1730.
Wang et al., "TPC Proteins are Phosphoinositide-Activated Sodium-Selective ion Channels in Endosomes and Lysosomes", Cell, 2012, vol. 151, pp. 372-383.
Yan et al., "Palette of Fluorinated Voltage-Sensitive Hemicyanine Dyes", Proc. Natl. Acad. Sci. USA, 2012, vol. 109, No. 50, pp. 20443-20448.

* cited by examiner a
M
R
Voltmeter
mV
-50
0
+50
3'
$D_A$
$D_T$
$D_V$
b
RVF
POPE
c
-100 mV
-60 mV
-20 mV
+20 mV
+40 mV
+100 mV
d
Norm. G/R
Norm. F/F$_0$
mV
-80
-40
0
40
80
1.3
1.1
0.9
0.7
e
Resting
-100 mV
+100 mV
0
0.5
f
Abs. G/R
0.35
0.3
0.25
0.2
0.15
R
-100
+100 a
b
-100 mV
-60 mV
-20 mV
+20 mV
+60 mV
+100 mV
c
IMP (mV)
Norm. G/R
PMP (mV)
d
HEK 293T
COS-7
RAW 264.7
BHK-21
e
$V_{Ly}$ (mV)
***
ns
*
**
COS-7
RAW 264.7
BHK-21
HEK 293T
Baf-A1
NS1619
ML-SA1
ML-SA1 +NS1619
Torin 1
Torin 1 + NS1619
f
$\Delta V_{mem}$ (mV)
Veh (Ly)
ML-SA1 (Ly)
ML-SA1 (EE)
Time (sec)

A
DV (RVF)
DV (DBCO)
EtBr
RVF
38mer
B
Voltair^PM
3'
D_A
D_T
D_V
D_A'
C
D_V
D_T
D_A
Atto647N

A pH 4.5
pH 5.0
pH 7.0
F/F0
mV
-100
-50
0
+50
+100
% ΔF/F (100 mV)
4.5
5.0
7.0

B

G/R
pH
4.0
4.5
5.0
5.5
6.0
6.5
7.0

A
hMSR1-CFP
DNA-Atto647N
Merge
-mBSA
+mBSA
DIC

B
1.0
0.5
0.0
PCC
EE
LE
Ly
0
40
80
120
Time (min)

D

| Protein | Inhibition | Activation | $\lvert \Delta V_{lys} \rvert$ (Initial – Final) | |
|---|---|---|---|---|
| | | | Electrophysiology | Voltair |
| **TPC2** | ATP | - | 20 mV[21] | - |
| | *trans NED-19* | - | - | 35 mV |
| **TRPML1** | - | ML-SA1 | 30 mV[23] | 90 mV |
| **Slo1** | - | cyto-$Ca^{2+}$ | 40 mV[22] | - |
| | | NS1619 | - | 50 mV |
| **mTORC1** | Torin-1 | - | n.d. | 60 mV |

DNA-BASED VOLTMETER FOR ORGANELLES

CROSS-REFERENCE TO RELATED APPLICATIONS

This application is a section 371 national phase of PCT/US2021/013745, filed Jan. 15, 2021, which claims the benefit of priority of U.S. Provisional Patent Application No. 62/961,615, filed Jan. 15, 2020, both which are hereby incorporated by reference in its entirety.

STATEMENT REGARDING FEDERALLY SPONSORED RESEARCH OR DEVELOPMENT

This invention was made with government support under Grant No. FA9550-19-0003 awarded by the Air Force Office of Scientific Research, Grant Nos. R21 NS114428 and 1R01NS112139-01A1 awarded by the National Institute of Health, Grant No. P30DK42086 awarded by the National Institute of Diabetes and Digestive and Kidney Diseases. The government has certain rights in the invention.

STATEMENT REGARDING SEQUENCE LISTING

A computer readable form of the Sequence Listing is filed with this application by electronic submission and is incorporated into this application by reference in its entirety. The sequence listing submitted herewith is contained in the text file created Jan. 26, 2023, entitled "20-037-WO-US_Sequence-Listing_ST25.txt" and 4 kilobytes in size.

BACKGROUND OF DISCLOSURE

Field of the Disclosure

This disclosure relates to methods for determining membrane potential across membranes of organelles and cells. More particularly, this disclosure relates to nucleic acid complexes comprising a voltage-sensing fluorophore conjugated to one single-stranded nucleic acid molecule and methods for using such nucleic acid complexes in determining the membrane potential.

Technical Background

Membrane potential is a key property of all biological membranes and underlies how membranes respond to electrical impulses and transduce chemical signals. It is therefore a fundamental signaling cue in all cells. Although the membrane potential of the plasma membrane is relatively straightforward to measure due to its accessibility to electrical and chemical probes, that of intracellular organelles is not. Since membranes of intracellular organelles enclose lumens of very different ionic compositions from the cytosol, they are therefore expected to maintain distinctive membrane potentials. In fact, electrophysiology on purified mitochondria and lysosomes isolated from disrupted cells have revealed that their membrane potentials are −140 mV (lumen negative) and +100 mV (lumen positive) respectively compared to −70 mV (cytosol negative) for the plasma membrane of a resting neuronal cell.

Electrophysiology on isolated organelles indicates that membrane potential is a major regulator of organelle function. The mitochondrial membrane potential generated by the Krebs cycle is harnessed to transport ions and charged compounds between the cytosol and the mitochondrial lumen. Its high negative membrane potential changes along with cellular metabolism thereby regulating mitochondrial fission and fusion. In fact, depolarized mitochondria cannot undergo effective fusion, and are degraded by mitophagy. Lysosomes harbor several voltage-gated ion channels and transporters, the functions of many of which are still unknown. Electrophysiology of isolated lysosomes reveals that membrane potential regulates lysosome functions such as the refilling of lumenal calcium and fusion with other organelles.

Importantly, the role of membrane potential in the function of several intracellular organelles remains unaddressed as they are refractory to electrophysiology and there is a paucity of organelle-specific probes. The pH sensitivity in fluorescent proteins limits their applicability in organelles where lumenal pH and membrane potential are co-dependent. Alternatively, electrochromic hemicyanine dyes or photoinduced electron transfer (PeT) based voltage sensitive dyes are particularly attractive for organelles due to their low capacitive loads, high temporal resolution, photostability and response range. However, unlike proteins, voltage sensitive dyes cannot be targeted to specific organelles other than mitochondria.

SUMMARY OF THE DISCLOSURE

The role of membrane potential in most intracellular organelles remains unexplored because of the lack of suitable tools. The inventors have determined that novel nucleic acid complexes of the disclosure (e.g., a fluorescent DNA-nanodevice) can efficiently and accurately determine the absolute membrane potential and can do so in specific organelles in live cells. The nucleic acid complexes of the disclosure are generally equipped with a voltage sensitive fluorophore, a reference fluorophore for ratiometric quantification, and can act as an endocytic tracer. With the nucleic acid complexes of the disclosure the membrane potential of different intracellular organelles can be measured in situ in live cells, which has not been possible previously.

Thus, one aspect of the disclosure provides a nucleic acid complex including:

- a first single-stranded nucleic acid molecule comprising a voltage-sensing fluorophore crosslinked to the first strand; and
- a second single-stranded nucleic acid molecule that is partially or fully complementary to the first single-stranded molecule,
  - wherein the nucleic acid complex further comprises a reference label conjugated to the first single-stranded nucleic acid molecule or the second single-stranded nucleic acid molecule and the reference label is capable of producing a signal.

Another aspect of the disclosure provides methods of determining the membrane potential in a cell. In general, such methods include providing a nucleic acid complex of the disclosure as described herein; measuring the intensity of the signal of the voltage-sensing fluorophore and the signal of the reference probe, wherein the intensity of the signal of the reference probe is independent on change in membrane potential; and determining the membrane potential from the measured signals.

Another aspect of the disclosure relates to a cell comprising a nucleic acid complex described herein that is conjugated to the cell (e.g., cell membrane). The nucleic acid complex may be reversibly conjugated to the cell, or the nucleic acid complex is irreversibly conjugated to the cell.

In some embodiments, the nucleic acid complex is conjugated to the organellar membrane.

Another aspect of the disclosure relates to methods for screening a candidate drug in a model cell or organism, the method including delivering the nucleic acid complex of the disclosure to the cell or organism; contacting the cell or organism with the candidate drug, measuring the intensity of the signal; and determining the membrane potential from the measured signal. In some embodiments, the model cell or organism is a model for a lysosomal storage disease. In some embodiments, the disease is a lysosomal storage disease. In some embodiments, the model cell or organism is a model for a disease in which membrane potential is implicated.

Another aspect of the disclosure relates to a method for detecting the severity of a disease, the progression of a disease, or the presence of a disease, the method including delivering the nucleic acid complex of the disclosure to a sample; measuring the intensity of the signal; and determining the membrane potential from the measured signal.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the invention will become apparent to those skilled in the art from this detailed description.

BRIEF DESCRIPTION OF THE DRAWINGS

The accompanying drawings are included to provide a further understanding of the systems and methods of the disclosure, and are incorporated in and constitute a part of this specification. The drawings are not necessarily to scale, and sizes of various elements may be distorted for clarity. The drawings illustrate one or more embodiment(s) of the disclosure and, together with the description, serve to explain the principles and operation of the disclosure.

DETAILED DESCRIPTION

Figure 1:
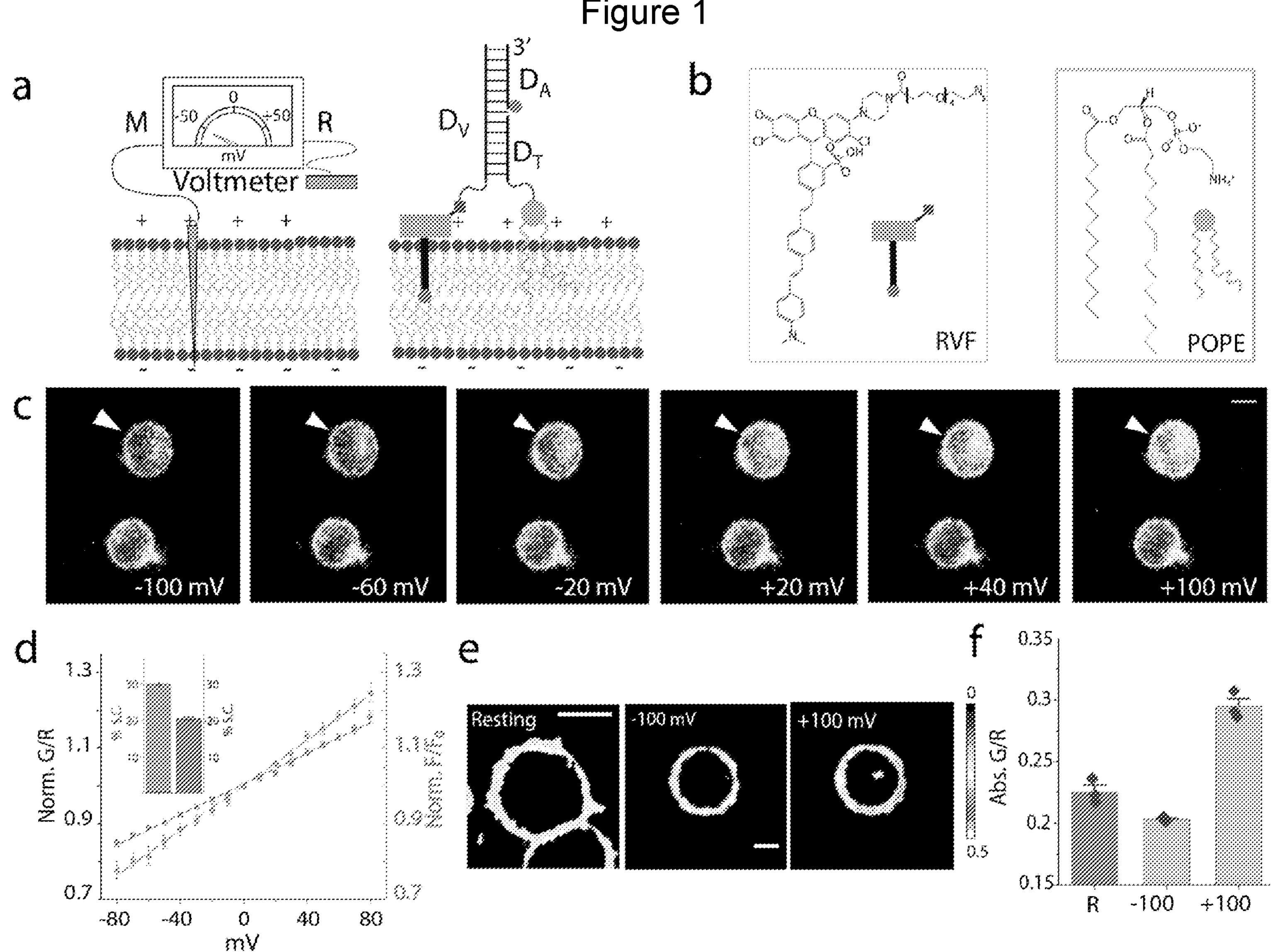
FIG. 1 illustrates design and characterization of Voltair probes. (A) Schematic of the working principle of DNA voltmeter Voltair: Measuring probe (M) is a voltage sensitive dye (RVF) conjugated to a DNA duplex that is membrane-tethered by attachment to a lipid anchor (POPE). Reference probe (R) is a DNA duplex with a reference dye (ATTO™647N) that together with RVF reports membrane potential ratiometrically. (B) Structure of a conjugatable version of RVF (RVF-$N_3$) and the lipid anchor POPE. (C) Images show pixel-wise ratio of RVF to ATTO™647N fluorescence intensities (G/R) as a function of membrane potential applied by whole cell voltage clamping. Voltage clamped cell shown by arrow head. Scale: 10 μm. (D) Sensor response of Voltair$^{PM}$ and unmodified RVF as a function of plasma membrane potential in HEK 293T cells. G/R values are normalized to that at 0 mV. Inset: Percentage signal change (S.C.) of Voltair$^{PM}$ and unmodified RVF from 0 to 100 mV in (D). (E, F) G/R values of the plasma membranes of resting cells (Res) and cells voltage clamped at −100 mV and +100 mV. Error bar represents mean±s.e.m. of three independent trials. Scale: 10 μm.

The particulars shown herein are by way of example and for purposes of illustrative discussion of certain embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

In view of the present disclosure, the methods and systems described herein can be configured by the person of ordinary skill in the art to meet the desired need. As provided above, inventors have found a novel nucleic acid complex, such as a DNA-based nanodevice referred to as Voltair in the Example, that functions as a non-invasive, organelle-targetable, ratiometric reporter of absolute organellar membrane potential in live cells. DNA is a versatile, programmable scaffold that is highly suited to chemical imaging of living systems. As a result, the complexes of the disclosure bearing a range of analyte detection chemistries have been used to quantitatively map diverse analytes in living systems. By leveraging the 1:1 stoichiometry of DNA hybridization, the inventors incorporated a reference fluorophore and the desired detection chemistry in a precise stoichiometry to yield ratiometric probes. For example, the inventors specifically measured the membrane potential of different organelles such as the early endosome, the late endosome and the lysosome, and mapped membrane potential changes as a function of endosomal maturation using the nucleic acid complex of the disclosure. The nucleic acid complex of the disclosure was also targeted to the recycling endosomes as well as the trans-Golgi network to quantify the membrane potentials. By measuring the contribution of the electrogenic Vacuolar $H^+$-ATPase (V-ATPase) proton pump to the membrane potentials of various organelles, the inventors determined that each organelle membrane showed different electrochemical characteristics.

As provided above, one aspect of the disclosure includes nucleic acid complexes. The nucleic acid complexes of the disclosure as described herein include a voltage-sensing fluorophore crosslinked to a first single-stranded nucleic acid molecule. Such voltage-sensing fluorophores may be single wavelength indicators or ratiometric indicators. In one embodiment, the voltage-sensing fluorophore is a single wavelength indicator. Numerous voltage-sensing fluorophores known in the art may be used in the complexes and methods of the disclosure, such as fluorophores including xanthenes, coumarins, cyanines, bimanes, etc. In certain embodiments, the voltage-sensing fluorophore comprises a xanthene moiety (e.g., comprises a rhodamine but may be further modified or substituted). In certain embodiments, the voltage-sensing fluorophore comprises rhodamine wherein any available position on the rhodamine may be functionalized as to allow for crosslinking to the first strand. For example, one of skill in the art recognizes that a hydrogen atom on the amine group may be replaced by a functional group that is configured to crosslink to the first strand. Thus, in certain embodiments, the voltage-sensing fluorophore comprises a moiety configured to insert into the biological membrane and optionally a spacer moiety.

The voltage-sensing fluorophore as described herein can be crosslinked to the first single-stranded nucleic acid molecule using linkers and methods known in the art. For example, the $Ca^{2+}$ fluorophore can be crosslinked using peptide chemistry, click chemistry, by forming ester, ether, thioether, disulfide, amine reactive N-Hydroxysuccinimidyl (NHS) esters, isocyanates, and isothiocyanates bonds, etc. In general, the Voltage-sensing fluorophore is crosslinked to the first strand through a linker moiety stable under physiological conditions.

In certain embodiments, the present inventors have determined that the voltage-sensing fluorophore can be crosslinked to the first single-stranded nucleic acid molecule using click chemistry. Thus, in certain embodiments, the voltage-sensing fluorophore is crosslinked to the first strand through a triazole, thioether, or alkenyl sulfide group. For example, the triazole, thioether, or alkenyl sulfide group can be formed from an azide or thiol moiety on the voltage-sensing fluorophore and an alkyne or alkene moiety on the first strand. In another example, the triazole, thioether, or alkenyl sulfide group can be formed from an azide or thiol moiety on the first strand and an alkyne or alkene moiety on the voltage-sensing fluorophore.

In certain embodiments, the voltage-sensing fluorophore of the disclosure as described herein includes the following formula:

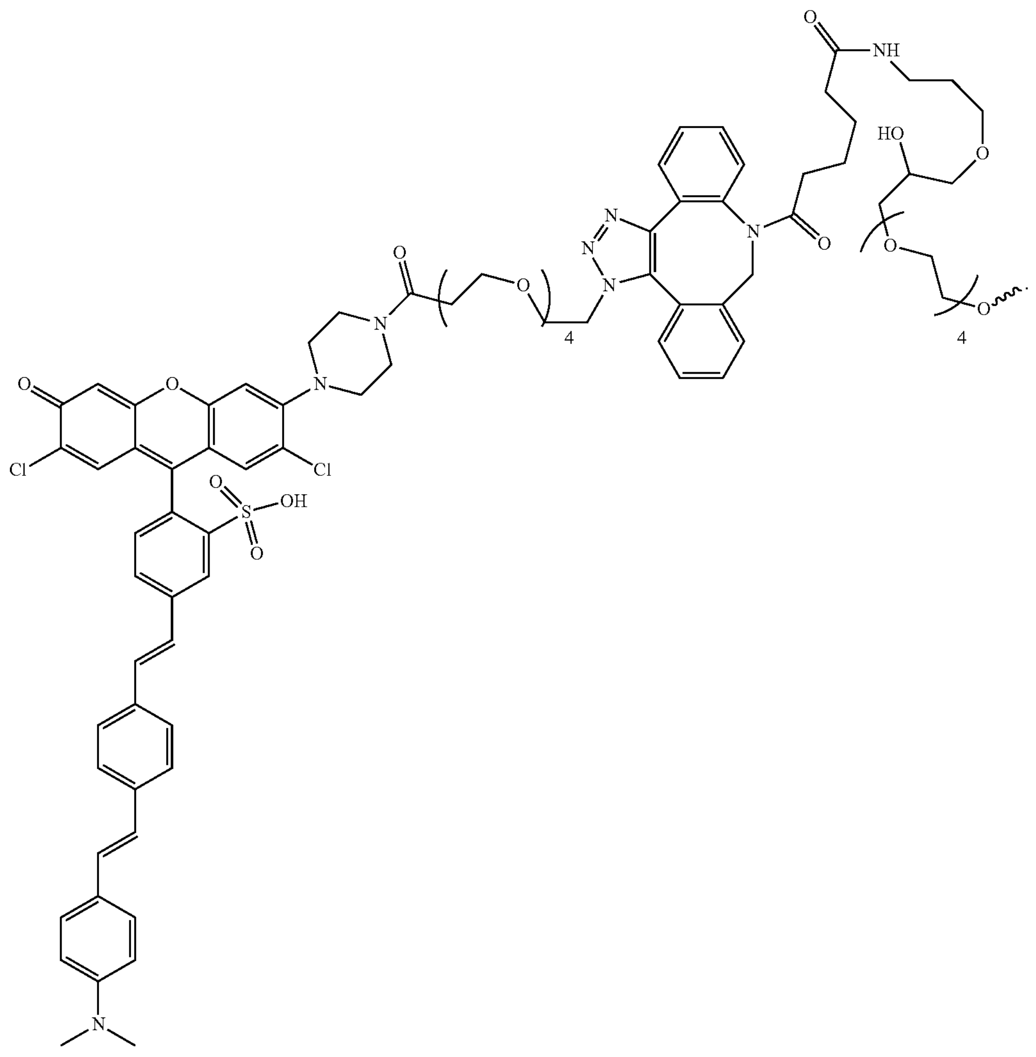

The nucleic acid complexes of the disclosure may include one or more reference labels capable of producing a signal. Such reference labels may be detectable by one or more means including, but not limited to, spectroscopic, photochemical, biochemical, immunochemical, or chemical assays. The method of linking or conjugating the label to the nucleotide depends on the type of label(s) used and the position of the label on the nucleotide.

In certain embodiments, the nucleic acid complexes of the disclosure include a reference label crosslinked to a first single-stranded nucleic acid molecule. In other embodiments, the nucleic acid complexes of the disclosure include a reference label crosslinked to a second single-stranded nucleic acid molecule.

In certain embodiments, nucleic acid complexes of the disclosure as describe herein comprises the 1:0.5 to 0.5:1 stoichiometry of the voltage-sensing fluorophore and the reference label. For example, in certain embodiments, the voltage-sensing fluorophore and the reference label are present in about 1:0.5 to 1:1 stoichiometry or in about 1:1 to 0.5:1 stoichiometry. In certain embodiments, the voltage-sensing fluorophore and the reference label are present in about 1:1 stoichiometry.

As used herein, "labels" are chemical or biochemical moieties useful for labeling a nucleic acid. Labels include, for example, fluorescent agents, chemiluminescent agents, chromogenic agents, quenching agents, radionucleotides, enzymes, substrates, cofactors, inhibitors, nanoparticles, magnetic particles, and other moieties known in the art capable of generating a measurable signal. Labels may be covalently or noncovalently joined to the nucleotide. In some embodiments of the nucleic acid molecules of the disclosure as described herein, the reference label is a "fluorescent dye" or a "fluorophore." In certain embodiments, the reference label is ATTO™ 647N.

Other dyes that may be used in as reference labels include, but are not limited to, the following dyes sold under the following trade names: 1,5 IAEDANS; 1,8-ANS; 4-methylumbelliferone; 5-carboxy-2,7-dichlorofluorescein; 5-carboxyfluorescein (5-FAM); 5-carboxytetramethylrhodamine (5-TAMRA); 5-hydroxy tryptamine (HAT); 5-ROX (carboxy-X-rhodamine); 6-carboxyrhodamine 6G; 6-JOE; 7-amino-4-methylcoumarin; 7-aminoactinomycin D (7-AAD); 7-hydroxy-4-methylcoumarin; 9-amino-6-chloro-2-methoxyacridine; ABQ; Acid Fuchsin; ACMA (9-amino-6-chloro-2-methoxyacridine); Acridine Orange; Acridine Red; Acridine Yellow; Acriflavin; Acriflavin Feulgen SITSA; ALEXA FLUOR®350; ALEXA FLUOR®430; ALEXA FLUOR®488; ALEXA FLUOR®532; ALEXA FLUOR®546; ALEXA FLUOR®568; ALEXA FLUOR®594; ALEXA FLUOR®633; ALEXA FLUOR®647; ALEXA FLUOR®660; ALEXA FLUOR®680; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO™-TAG CBQCA; ATTO™-TAG FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); BLANOPHOR® FFG; BLANOPHOR® SV; BOBO™-1; BOBO™-3; BODIPY®492/515; BODIPY®493/503; BODIPY®500/510; BODIPY®505/515; BODIPY®530/550; BODIPY®542/563; BODIPY®558/568; BODIPY®564/570; BODIPY®576/589; BODIPY®581/591; BODIPY®630/650-X; BODIPY®650/665-X; BODIPY®665/676; BODIPY® FL; BODIPY® FL ATP; BODIPY® FI-Ceramide; BODIPY®R6G SE; BODIPY®TMR; BODIPY®TMR-X conjugate; BODIPY®TMR-X, SE; BODIPY®TR; BODIPY®TR ATP; BODIPY®TR-X SE; BO-PRO™-1; BO-PRO™-3; Brilliant Sulphoflavin FF; Calcein; Calcein Blue; CALCIUM CRIMSON™; CALCIUM GREEN™; CALCIUM ORANGE™; CALCOFLUOR™ White; CASCADE BLUE®; Catecholamine; CCF2 (GENEBLAZER®); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; CY®2; CY®3.18; CY®3.5; CY®3; CY®5.18; CY®5.5; CY®5; CY®7; Cyan GFP; cyclic AMP FLUOROSENSOR™ (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DilC18(5)); DIDS; Dihydorhodamine 123 (DHR); Dil (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM® 1-43; FM® 4-46; FURA RED™; FURA RED/Fluo-3; Fura-2; Fura-2/BCECF; GENACRYL™ Brilliant Red B; GENACRYL™ Brilliant Yellow 10GF; GENACRYL™ Pink 3G; GENACRYL™ Yellow 5GF; GENEBLAZER® (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; LYSOTRACKER® Blue; LYSOTRACKER® Blue-White; LYSOTRACKER® Green; LYSOTRACKER® Red; LYSOTRACKER® Yellow; LYSOSENSOR™ Blue; LYSOSENSOR™ Green; LYSOSENSOR™ Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; MITOTRACKER® Green FM; MITOTRACKER® Orange; MITOTRACKER® Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant lavin E8G; OREGON GREEN™ 488-X; OREGON GREEN™; OREGON GREEN™ 488; OREGON GREEN™ 500; OREGON GREEN™ 514; Pacific Blue; Pararosaniline (Feulgen); PBFI; PE-Cy5; PE-Cy7; PerCP; PerCP-Cy5.5; PE-TEXAS RED® [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE—TEXAS RED®]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO®11; SYTO® 12; SYTO® 13; SYTO® 14; SYTO® 15; SYTO® 16; SYTO® 17; SYTO® 18; SYTO® 20; SYTO® 21; SYTO® 22; SYTO® 23; SYTO® 24; SYTO® 25; SYTO® 40; SYTO® 41; SYTO® 42; SYTO® 43; SYTO® 44; SYTO® 45; SYTO® 59; SYTO® 60; SYTO® 61; SYTO® 62; SYTO® 63; SYTO® 64; SYTO® 80; SYTO® 81; SYTO® 82; SYTO® 83; SYTO® 84; SYTO® 85; SYTO®X Blue; SYTO®X Green; SYTO®X Orange; TET™; Tetracycline; Tetramethylrhodamine (TRITC); TEXAS RED®; TEXAS RED®-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS; TMR; TO-PRO-1; TO-PRO-3; TO-PRO-5; TOTO-1; TOTO-3; TriColor (PE-Cy5); TRITC TetramethylRodamineIsoThioCyanate; True Blue; TRU-RED™; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; PHRODO® (available from Thermo Fischer Scientific, Inc. Waltham, MA), and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The voltage-sensing fluorophore and reference labels can be conjugated to the nucleic acid molecules directly or indirectly by a variety of techniques. Depending upon the precise type of voltage-sensing fluorophore or label used, the voltage-sensing fluorophore or label can be located at the 5' or 3' end of the oligonucleotide, located internally in the oligonucleotide's nucleotide sequence, or attached to spacer arms extending from the oligonucleotide and having various sizes and compositions to facilitate signal interactions.

Using commercially available phosphoramidite reagents, one can produce nucleic acid molecules containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Nucleic acid molecules may also incorporate functionalizing reagents having one or more sulfhydryl, amino or hydroxyl moieties into the nucleic acid sequence. For example, a 5' phosphate group can be incorporated as a radioisotope by using polynucleotide kinase and [γ32P] ATP to provide a reporter group. Biotin can be added to the 5' end by reacting an aminothymidine residue, introduced during synthesis, with an N-hydroxysuccinimide ester of biotin. Voltage-sensing fluorophore or labels at the 3' terminus, for example, can employ polynucleotide terminal transferase to add the desired moiety, such as for example, cordycepin, 35S-dATP, and biotinylated dUTP.

The nucleic acid molecules and complexes of the disclosure, in some embodiments, comprise a targeting moiety, such as a nucleic acid, small molecule, or polypeptide that has an affinity for a certain target or, by virtue of its chemical makeup, is targeted to a particular location in the cell. The targeting moiety can act as a handle to target the nucleic acid complexes of the disclosure to different subcellular locations. The targeting moiety may be a nucleic acid that binds to a receptor protein, and the receptor protein may be one that is intracellularly targeted or conjugated to a protein that is intracellularly targeted. The targeting moiety or receptor protein may be a targeting nucleic acid or a protein such as a plasma membrane protein that gets endocytosed, any proteins that possess a natural receptor, a protein that traffics between intracellular locations via the plasma membrane, toxins, viruses and viral coat proteins, cell penetrating peptides, signal sequences, intracellular targeting sequences, small organic molecules, endocytic ligands and trafficking proteins.

In some embodiments, the targeting moiety is a nucleic acid sequence. In some embodiments, the targeting moiety has a cognate artificial protein receptor. The artificial receptor may be, for example, a single chain variable fragment (scFv), transcription factor, Zn-fingered protein, leucine zipper, or DNA binding immunoglobulin.

The targeting moiety of the disclosure may be encoded on the same nucleic acid strand as the first single-stranded nucleic acid molecule, the second single-stranded nucleic acid molecule, the third single-stranded nucleic acid molecule (if present), or any combination thereof. In certain embodiments, the targeting moiety is encoded in the first and/or second single-stranded nucleic acid molecule. In certain embodiments, the targeting moiety is encoded in the third single-stranded nucleic acid molecule.

In some embodiments, the targeting moiety is selected from an aptamer, a single strand domain targeted to an artificial protein receptor, a nucleic acid phosphate backbone that binds an anionic-ligand binding receptor, and an endocytic ligand. In some embodiments, the targeting moiety comprises a peptide directly or indirectly conjugated to the nucleic acid molecule. In some embodiments, the targeting moiety peptide comprises one or more of a fusogenic peptide, a membrane-anchoring peptide, a sub-cellular localization sequence, or a cell-receptor ligand. In some embodiments, the sub-cellular localization sequence targets the nucleic acid complex to a region of the cell where spatial localization of a targeted protein is present. In some embodiments, the sub-cellular localization sequence targets the nucleic acid complex to a region of the cell selected from the group consisting of: the cytosol, the endoplasmic reticulum, the mitochondrial matrix, the chloroplast lumen, the medial trans-Golgi cistemae, the lumen of lysosome, the lumen of an endosome, the peroxisome, the nucleus, and a specific spatial location on the plasma membrane. In some embodiments, the sub-cellular organelle is one that exchanges membrane directly or indirectly with the plasma membrane.

In some embodiments of the nucleic acid complex as described herein, the targeting moiety comprises one or more of membrane-anchoring groups. For example, the membrane-anchoring group may comprise 1-palmitoyl-2-oleoyl-sn-glycero-3-phosphoethanolamine (POPE) moiety. In certain embodiments, the POPE moiety may be conjugated to the targeting moiety through an optional linker (e.g., a tetra-ethylene glycol linker).

A provided above, the nucleic acid complexes of the disclosure include a first single-stranded molecule and a second single-stranded nucleic acid molecule that is partially or fully complementary to the first single-stranded molecule. In certain embodiments, the nucleic acid complexes of the disclosure include a first single-stranded molecule, a second single-stranded nucleic acid molecule that is partially complementary to the first single-stranded molecule, and a third single-stranded nucleic acid molecule that is partially complementary to the first single-stranded molecule.

In certain embodiments of the methods and nucleic acid molecule and complexes described herein, the second nucleic acid strand and/or the third nucleic acid strand is one that is only partially complementary to the first nucleic acid. A nucleic acid strand is fully complementary when all bases are capable of forming conventional Watson-Crick base-pairing (e.g. G-C and A-T base pairing). A nucleic acid strand is partially complementary when at least one of the base pairs is not complementary to the opposing strand. In some embodiments, the second single nucleic acid strand comprises at least 4 non-complementary nucleic acid bases. In some embodiments, the second single nucleic acid strand comprises at least, at most, or exactly 2, 3, 4, 5, 6, 7, 8, 9, 10, 12, 14, 16, 18, or 20 (or any derivable range therein) non-complementary nucleic acid bases. In some embodiments, the second nucleic acid strand comprises 8 non-complementary nucleic acid bases.

In certain embodiments of the nucleic acid complexes of the disclosure, each of the first single-stranded nucleic acid molecule, the second single-stranded nucleic acid molecule, and/or the third single-stranded nucleic acid molecule is independently less than 200 nucleotides. In some embodiments, each of the first single-stranded nucleic acid molecule the second single-stranded nucleic acid molecule, and/or the third single-stranded nucleic acid molecule is independently less than, at least, or exactly 20, 30, 40, 60, 80, 100, 125, 150, 175, 200, 225, 250, 275, 300, 350, 400, 450, 500, 550, 600, 650, 700, 750, 800, 900, or 1000 nucleotides in length, or any derivable range therein.

In some embodiments, the nucleic acid complex of the present disclosure self assembles two or all three strands through Watson-Crick base pairing, which is stable under physiological conditions.

In some embodiments, the nucleic acid is a peptide nucleic acid (PNA). The strand is conjugated to voltage-sensing fluorophore. In some embodiments, the first strain comprises PNA and voltage-sensing fluorophore. In some embodiments, the reference label is conjugated to DNA sequence that is complementary to PNA of the sensing module.

In some embodiments, a DNA strand is used as first strand and/or the second strand. In an embodiment of the present disclosure, the nucleic acid complex has a dsDNA part (minimum 15 bp sequence) resulting from the hybridization of the first strand and the second strand, or the first strand and the third strand, or the first strand with the second strand and the third strand. In certain embodiments, the nucleic acid complex comprises $d(AT)_4$ sequence and hence is targeted to any given compartment in any cell that expresses scFv tagged protein of choice.

In an exemplary, non-limiting embodiment, the nucleic acid complex as described herein comprises the first strain having the sequence 5'-ATCAACACTGCACACCAGACAGCAAGATCC-TATATATA/the voltage-sensing fluorophore/-3' (SEQ ID NO:01) or 5-/the voltage-sensing fluorophore/-TATATATAG-GATCTTGCTTCTGTGCCTGCAGTGTTGAT-3' (SEQ ID NO: 05).

In an exemplary, non-limiting embodiment, the nucleic acid complex as described herein comprises the second strain having the sequence 5-/the reference label/GGTGTGCAGTGTTGAT-3' (SEQ ID NO:02), 5'-TATATATAGGATCTTGCTGTCTGGTGTGCAG-TGTTGAT-/the reference label/-3' (SEQ ID NO:03), or 5-/the reference label/ATCAACACTGCAGGC-ACAGAGTCTGGTG-3' (SEQ ID NO: 06).

In an exemplary, non-limiting embodiment, the nucleic acid complex as described herein comprises the third strain having the sequence 5'-/membrane-anchoring group/TATATATAG-GATCTTGCTGTCT-3' (SEQ ID NO:04) or 5'-CACCAGACAGCAAGATCCTATATATAGGGG-GAUCAAUCCAAGGGACCCGGAAACG CUCCC-UUACACCCC-3' (SEQ ID NO: 07).

In an exemplary, non-limiting embodiment, the nucleic acid complex as described herein comprises the first strain having the sequence 5'-ATCAACACTGCACACCAGACAGCAAGATCC-TATATATA/the voltage-sensing fluorophore/-3' (SEQ ID NO:01), the second strain having the sequence 5'-/the reference label/GGTGTGCAGTGTTGAT-3' (SEQ ID NO:02), and the third strain having the sequence 5'-membrane-anchoring group/TATATATAG-GATCTTGCTGTCT-3' (SEQ ID NO:04).

In an exemplary, non-limiting embodiment, the nucleic acid complex as described herein comprises the first strain having the sequence 5'-ATCAACACTGCACACCAGACAGCAAGATCC-TATATATA/the voltage-sensing fluorophore/-3' (SEQ ID NO:01) and the second strand has the sequence 5'-TATATATAGGATCTTGCTGTCTGGTGTG-CAGTGTTGAT-/the reference label/-3' (SEQ ID NO:03).

In an exemplary, non-limiting embodiment, the nucleic acid complex as described herein comprises the first strain having the sequence 5-/the voltage-sensing fluorophore/-TATATATAG-GATCTTGCTTCTGTGCCTGCAGTGTTGAT-3' (SEQ ID NO: 05), the second strand has the sequence 5-/the reference label/ATCAACACTGCAGG-CACAGAGTCTGGTG-3' (SEQ ID NO: 06), and the third strand has the sequence 5'-CACCA-GACAGCAAGATCCTATATATAGGGGGAU-CAAUCCAAGGGACCCGGAAACG CUCCCUUA-CACCCC-3' (SEQ ID NO: 07).

As provided above, one aspect of the disclosure provides methods of determining the membrane potential in a cell.

The methods described herein may be used to monitor the membrane potential in real-time during cellular processes. In some embodiments, the methods are for monitoring endosomal maturation, organelle damage, or membrane repair.

The membrane potential, for example, may be determined in early endosome, late endosome, plasma membrane, lysosome, autophagolysosome, recycling endosome, cis Golgi network (CGN), trans Golgi network (TGN), endoplasmic reticulum (ER), peroxisomes, or secretory vesicles. In certain embodiments, the methods of the disclosure are suitable for determining the membrane potential in early endosome, late endosome, plasma membrane, lysosome, autophagolysosome, recycling endosome, or TGN.

Protein-based voltage indicators while powerful, have limited applicability to acidic organelles, as they are pH sensitive and cannot yet provide absolute membrane potential. Voltage sensitive dyes are attractive due to their low capacitive loads and pH insensitivity, but, on their own, cannot be targeted to organelles. The nucleic acid complex of the disclosure has the advantages of having the voltage sensitive fluorophore with the organelle-targetability of proteins to non-invasively measure the membrane potential of organelles. Thus, in certain embodiments, the methods of the disclosure are suitable for determining the membrane potential in organelles (e.g., endocytic, lysosomal, endosomal, golgi complex, intracellular, etc.). The method may be configured to determine the membrane potential in a single organelle in certain embodiments. In other embodiments, the method may be configured to determine in a plurality of individual organelles.

In order to determine the membrane potential, the intensity of the signal of the voltage-sensing fluorophore and the signal of the reference probe is measured. The membrane potential is then determined from the measured signals. The intensity of the signal of the reference probe is independent on change in membrane potential, whereas the intensity of the signal of the voltage-sensing fluorophore is dependent on change in membrane potential. In addition, in certain embodiments, the intensity of one or both signals (e.g., the signal from the voltage-sensing fluorophore, the signal of the reference probe, or both signals) varies as a function of at least the orientation of the voltage-sensing fluorophore in or on the membrane. In certain other embodiments, the intensity of the signal is irrelevant of the orientation of the voltage-sensing fluorophore.

As used herein, an increase or a decrease in a signal from the nucleic acid complex may refer to the change in a signal in the sample compared to a reference sample. The reference sample may be a control sample (e.g., an untreated population of cells where the effects of a drug or agent are being examined), or it may be the same sample at a different period of time, for instance, where the membrane potential is being monitored to follow one or more cellular processes.

In some embodiments, the signal intensity (e.g., the signal intensity from the voltage-sensing fluorophore) changes by at least twenty percent as the membrane potential is raised. In some embodiments, the signal intensity changes by at least 10, 20, 25, 30, 35, 40, 45, 50, 55, 60, 65, 70, 75, 80, 85, or 90% or any derivable range therein when the membrane potential is raised.

Fluorescence in the sample can be measured in a variety of ways, such as using a fluorometer or fluorescence microscopy. In general, excitation radiation, from an excitation source having a first wavelength, passes through excitation optics. The excitation optics cause the excitation radiation to excite the sample. In response, labels in the sample emit radiation which has a wavelength that is different from the excitation wavelength. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the membrane potential is determined by comparing the measured signal to a reference value. In some embodiments, the signal value and/or reference value is normalized. In some embodiments, the method further comprises creating a standard curve. A standard curve can be created by measuring the signal intensity at different known membrane potential values. A curve can be plotted as signal intensity vs. membrane potential. The signal intensity of an unknown membrane potential can then be determined by finding the corresponding reference value on the plot.

In some embodiments, the membrane potential may be monitored for the purposes of examining cellular phenomena and/or screening the effects of various compounds, wherein the level of the signal from a nucleic acid complex (e.g., increased or decreased signal) in a test sample at a first time point is determined and compared with the level found in a test sample obtained at a later time point. The change in signal may reflect a relative change in the membrane potential between the two samples. For example, an increase in signal from one time point to another may indicate an increase in the membrane potential between the two time points. Likewise, a decrease in signal from one point to another may indicate a decrease in the membrane potential. The absolute level of signal may be compared to a reference sample of known standards or reference samples in order to determine the precise membrane potential of the sample. The sample can be classified or assigned to a particular membrane potential value based on how similar the measured levels were compared to the control levels for a given group.

As one of skill in the art will understand, there will be a certain degree of uncertainty involved in making this determination. Therefore, the standard deviations of the control group levels can be used to make a probabilistic determination and the method of this disclosure are applicable over a wide range of probability-based determinations. Thus, for example, and not by way of limitation, in one embodiment, if the measured level of signal falls within 2.5 standard deviations of the mean of any of the control groups, then that sample may be assigned to that group. In another embodiment if the measured level of signal falls within 2.0 standard deviations of the mean of any of the control groups then that sample may be assigned to that group. In still another embodiment, if the measured level of signal falls within 1.5 standard deviations of the mean of any of the control groups then that sample may be assigned to that group. In yet another embodiment, if the measured level of signal is 1.0 or less standard deviations of the mean of any of the control groups levels then that sample may be assigned to that group. Thus, this process allows determination, with various degrees of probability, in which group a specific sample should be placed.

Statistical methods can also be used to set thresholds for determining when the signal intensity in a test sample can be considered to be different than or similar to the reference level. In addition, statistics can be used to determine the validity of the difference or similarity observed between a test sample's signal intensity and the reference level. Useful statistical analysis methods are described in L. D. Fisher & G. vanBelle, Biostatistics: A Methodology for the Health Sciences (Wiley-Interscience, NY, 1993). For instance, confidence ("p") values can be calculated using an unpaired 2-tailed t test, with a difference between groups deemed significant if the p value is less than or equal to 0.05.

To minimize artefactually low fluorescence measurements that occur due to cell movement or focusing, the fluorescence of the nucleic acid complex can be compared to the fluorescence of a second sensor, e.g., a second nucleic acid complex that is also present in the measured sample. The second nucleic acid complex should have an emission spectrum distinct from the first nucleic acid complex so that the emission spectra of the two sensors can be distinguished. Because experimental conditions such as focusing and cell movement will affect fluorescence of the second sensor as well as the first sensor, comparing the relative fluorescence of the two sensors may allow for the normalization of fluorescence. A convenient method of comparing the samples is to compute the ratio of the fluorescence of the first fluorescent protein sensor to that of the second fluorescent protein sensor.

The nucleic acid complexes as described herein can be readily introduced into a host cell, e.g., a mammalian (optionally human), bacterial, parasite, yeast or insect cell by any method in the art. For example, nucleic acids can be transferred into a host cell by physical, chemical or biological means. It is readily understood that the introduction of the nucleic acid molecules yields a cell in which the membrane potential may be monitored. Thus, the method can be used to measure membrane potential in cells cultured in vitro. The nucleic acid complex of the disclosure can also be readily introduced into a whole organism to measure the membrane potential in a cell or tissue in vivo. For example, nucleic acid complex of the disclosure can be transferred into an organism by physical, chemical or biological means, e.g., direct injection. In certain embodiments, the methods for introducing nucleic acid complexes of the disclosure may be those disclosed in Chakraborty et al., "Nucleic Acid-Based Nanodevices in Biological Imaging," *Annu. Rev. Biochem.* 85:349-73 (2016), incorporated in its entirety by reference herein.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the nucleic acid complex of the disclosure into host cells (in vitro, ex vivo or in vivo). In some embodiments, the nucleic acid complex of the disclosure may be associated with a lipid. The nucleic acid complex of the disclosure associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/nucleic acid complex compositions are not limited to any particular structure in solution. For example, they may be present in a bilayer structure, as micelles, or with a "collapsed" structure. They may also simply be interspersed in a solution, possibly forming aggregates which are not uniform in either size or shape.

In some embodiments, the one or more nucleic acid complexes of the disclosure are linked to a targeting sequence that directs the nucleic acid complex to a desired cellular compartment.

The methods, compositions, nucleic acid complexes, and kits of the disclosure can be used for the detection of diseases, the monitoring of diseases, and as a drug screening platform. In some embodiments of the disclosure, the disease is characterized as a lysosomal dysfunction disease or its pathology includes lysosomal dysfunction. Such disease includes, but is not limited to, autosomal recessive osteopetrosis, Farber disease, Krabbe disease (infantile onset and late onset), Fabry disease (Alpha-galactosidase A), Schindler disease (Alpha-galactosidase B), Sandhoff disease (infantile, juvenile, or adult onset), Tay-Sachs, juvenile hexosaminidase A deficiency, chronic hexosaminidase A deficiency, glucocerebroside, Gaucher disease (Type I, II, and III), lysosomal acid lipase deficiency (early onset and late onset), Niemann-Pick disease (Type A and B), sulfatidosis, metachromatic leukodystrophy (MLD), saposin B deficiency, multiple sulfatase deficiency, mucopolysaccharidoses: MPS I Hurler Syndrome, MPS I S Scheie Syndrome, MPS I H-S Hurler-Scheie Syndrome, Type II (Hunter syndrome), Type III (Sanfilippo syndrome), MPS III A (Type A), MPS III B (Type B), MPS III C (Type C), MPS III D (Type D), Type IV (Morquio), MPS IVA (Type A), MPS IVB (Type B), Type VI (Maroteaux-Lamy syndrome), Type VII Sly Syndrome, Type IX (Hyaluronidase Deficiency); Mucolipidosis: Type I (Sialidosis), Type II (I-cell disease), Type III (Pseudo-Hurler Polydystrophy/Phosphotransferase Deficiency), Type IV (Mucolipidin 1 deficiency); Niemann-Pick disease (Type C and D), Neuronal Ceroid Lipofuscinoses: Type 1 Santavuori-Haltia disease/Infantile NCL (CLN1 PPT1), Type 2 Jansky-Bielschowsky disease/Late infantile NCL (CLN2/LINCL TPP1), Type 3 Batten-Spielmeyer-Vogt disease/Juvenile NCL (CLN3), Type 4 Kufs disease/Adult NCL (CLN4), Type 5 Finnish Variant/Late Infantile (CLN5), Type 6 Late Infantile Variant (CLN6), Type 7 CLN7, Type 8 Northern Epilepsy (CLN8), Type 8 Turkish Late Infantile (CLN8), Type 9 German/Serbian Late Infantile (Unknown), Type 10 Congenital Cathepsin D Deficiency (CTSD); Wolman disease, alpha-mannosidosis, beta-mannosidosis, aspartylglucosaminuria, fucosidosis, lysosomal transport diseases, cystinosis, pycnodysostosis, salla disease/sialic acid storage disease, infantile free sialic acid storage disease (ISSD), glycogen storage diseases, Type II Pompe Disease, Type IIIb Danon disease, and cholesteryl ester storage disease. In some embodiments, the disease is autosomal recessive osteopetrosis. In some embodiments, the disease is Niemann-Pick C disease. In certain embodiments, the disease is osteopetrosis, Mucolipidosis (e.g., Type IV), Gaucher disease, or Niemann-Pick C disease.

In some embodiments, the disease is characterized as a disease in which membrane potential is implicated (e.g., linked to mitochondrial membrane potential), or which can benefit from modifying or disrupting the membrane potential. Such disease includes, but is not limited to, bacterial (e.g., staphylococcal), viral (e.g., coronavirus), fungal, or parasitic infection, Parkinson's disease and an autoimmune disease such as rheumatoid arthritis and lupus.

The materials and components described for use in the methods may be suited for the preparation of a kit. Thus, the disclosure provides a detection kit useful for determining the membrane potential in an organelle, cell or organism. Specifically, the technology encompasses kits for determining the membrane potential of one or more cells in a sample. For example, the kit can comprise a nucleic acid complex as described herein.

In some embodiments, the methods described herein may be performed by utilizing pre-packaged diagnostic kits comprising the necessary reagents to perform any of the methods of the technology. For example, such a kit would include a detection reagent for determining the membrane potential of an organelle, cell or organism. In one embodiment of such a kit, the detection reagents are the nucleic acid complexes of the disclosure. Oligonucleotides are easily synthesized and are stable in various formulations for long periods of time, particularly when lyophilized or otherwise dried to a powder form. In this form, they are easily reconstituted for use by those of skill in the art. Other reagents and consumables required for using the kit could be easily identified and procured by those of skill in the art who wish to use the kit. The kits can also include buffers useful in the methods of the technology. The kits may contain instructions for the use of the reagents and interpreting the results.

In some embodiments, the technology provides a kit comprising at least one sample (e.g., a fluorophore standard) packaged in one or more vials for use as a control. Each component of the kit can be enclosed within an individual container and all of the various containers can be within a single package, along with instructions for performing the assay and for interpreting the results of the assays performed using the kit.

In some embodiments, the kit comprises a device for the measurement of the membrane potential in a cell sample. In some embodiments, the device is for measuring membrane potential in cell culture or in whole, transparent organisms (e.g., *C. elegans*, coelomocytes in nematodes, or microglia in zebrafish brains).

Definitions

The terms "a," "an," "the" and similar referents used in the context of describing the invention (especially in the context of the following embodiments and claims) are to be construed to cover both the singular and the plural, unless otherwise indicated herein or clearly contradicted by context.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye.

As used herein, "crosslinked" refers to a covalent connection between the nucleic acid molecule and another moiety of interest, such as the fluorophore. In certain embodiments, the crosslink between the nucleic acid molecule and this moiety is water compatible. In certain embodiments, the crosslink between the nucleic acid molecule and this moiety is stable under physiological conditions.

As used herein, "nucleic acid," "nucleotide sequence," or "nucleic acid sequence" refer to a nucleotide, oligonucleotide, polynucleotide, or any fragment thereof and to naturally occurring or synthetic molecules. The term "peptide nucleic acid" or "PNA" as used herein generally refers to nucleic acid analogue in which the sugar phosphate backbone of natural nucleic acid has been replaced by a synthetic peptide backbone. The term "RNA equivalent" in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. It is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides. In the present disclosure, PNA or PNA strand or PNA sequence is used interchangeably and has the same scope or meaning. In the present disclosure, DNA or DNA strand or DNA sequence is used interchangeably and has the same scope or meaning. In the present disclosure, RNA or RNA strand or RNA sequence is used interchangeably and has the same scope or meaning.

One nucleic acid sequence may be "complementary" to a second nucleic acid sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15M NaCl, 0.015M sodium citrate, pH 7.2).

All percentages, ratios and proportions herein are by weight, unless otherwise specified.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the disclosure are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of various aspects of the disclosure are described herein, including the best mode known to the inventors for carrying out the methods described herein. Of course, variations on these described embodiments will become apparent to those of ordinary skill in the art upon reading the description. The skilled artisan will employ such variations as appropriate, and as such the methods of the disclosure can be practiced otherwise than specifically described herein. Accordingly, the scope of the disclosure includes all modifications and equivalents of the subject matter recited in the claims appended hereto as permitted by applicable law. Moreover, any combination of the herein-described elements in all possible variations thereof is encompassed by the disclosure unless otherwise indicated herein or otherwise clearly contradicted by context.

Examples

Certain aspects of the disclosure are illustrated further by the following examples, which are not to be construed as limiting the disclosure in scope or spirit to the specific methods and materials described in them.

Materials and Methods

Reagents: All modified oligonucleotides (Table 1) were purchased from IDT (USA). Fluorescently labelled oligonucleotides were subjected to ethanol precipitation and quantified by UV absorbance at 260 nm. CELLMASK™ reagents and TMR-Dextran were purchased from molecular probes/Life Technologies (USA). Maleylated BSA (mBSA) and fluorescent transferrin (Tf-ALEXA FLUOR®546) were conjugated according to previously published protocols. Torin-1, ML-SA1, NS1619 and trans-Ned-19 were purchased from Cayman Chemical (USA). Phenyl triflimide was purchased from TCi America (USA). N-Boc-piperazine was purchased from Oakwood chemicals (USA). Azido-PEG4-NHS was purchased from Click Chemistry tools (USA). 1-palmitoyl-2-oleoyl-sn-glycero-3-phosphoethanolamine lipid was purchased from Avanti lipids (USA). All other reagents were purchased from Sigma-Aldrich (USA) unless otherwise specified.

Figure 5:
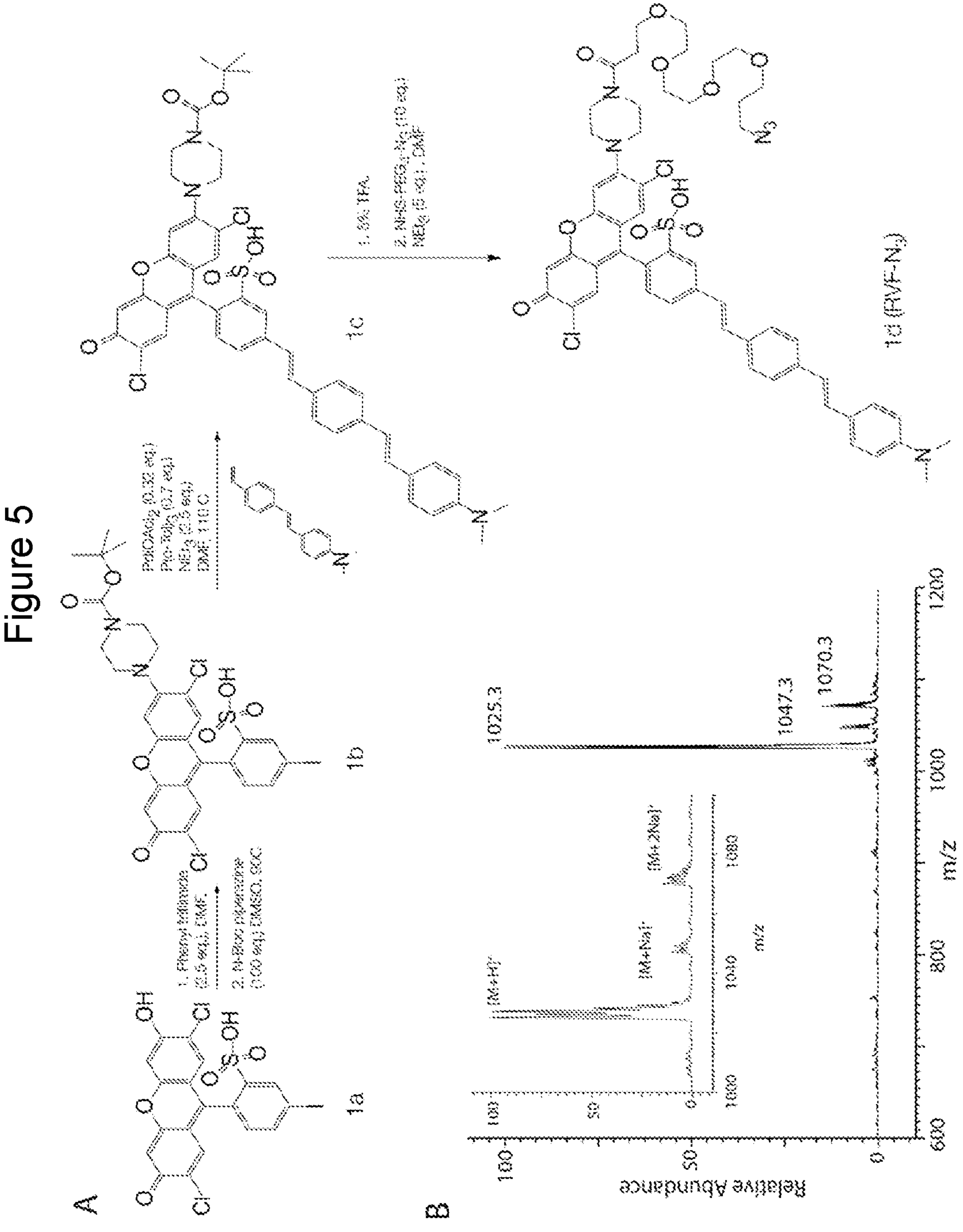
FIG. 5 illustrates synthesis of conjugatable RVF-$N_3$. (A) Reaction scheme for synthesis of azido-RVF. The azido group in RVF is utilized to conjugate it to the DNA strand $D_V$, the sensing component in the Voltair probes. (B) ESI-MS of RVF-$N_3$. Inset shows the region corresponding to the M+2 peaks arising from the CI isotopes.

Synthesis of RVF: Synthesis scheme shown in FIG. 5. Compound 1a (0.2 g, 0.36 mmol) was suspended in N,N-dimethylformamide (DMF) (1.4 mL) and cooled to 0° C.. Triethylamine (2.7 mL) and Phenyl triflimide (0.25 g, 0.72 mmol, 2 eq.) were added dropwise. The ice bath was removed and the reaction was stirred at room temperature for 2 hours. The reaction mixture was then diluted in water and extracted with dichloromethane (DCM) twice. Organic extracts were washed three times with brine and 1M HCl. The product was concentrated via rotor evaporation and dry DMSO was added (2 mL). N-Boc piperazine (3.72 g, 20 mmol, 100 eq.) was added and the reaction mixture was kept at 100° C. overnight. The reaction mixture was then diluted in water, extracted in DCM twice then washed with brine twice. The mixture was dried over anhydrous $Na_2SO_4$ and concentrated under reduced pressure. Silica gel column chromatography was performed in 5% methanol in chloroform to get 1b (0.08 g, 28%). ESI-MS (−) Expected mass=728.98, found=729.0.

A reaction tube was charged with 1b (70 mg, 0.0956 mmol), $Pd(OAc)_2$ (6.87 mg, 0.0306 mmol, 0.32 eq.), tri-o-tolylphosphine (20.4 mg, 0.067 mmol, 0.7 eq.) and (E)-N,N-dimethyl-4-(4-vinylstyryl)aniline (26.23 mg, 1.052 mmol, 1.1 eq.) which was previously synthesized according to literature. The tube was evacuated and backfilled with $N_2$ three times. 1 mL of dry DMF and 500 μL dry triethylamine were added via syringe, and the reaction was stirred at 110° C. overnight. The reaction mixture was diluted in water and extracted with DCM twice. The organic extract was washed with brine twice and concentrated under reduce pressure. Silica gel column chromatography was performed in 5% methanol in DCM to get somewhat orange-brown solid 1c (20 mg, 25%). ESI-MS (+), Expected mass=851.29, found=851.2.

A reaction vial with 1c (5 mg, 6.7 nmol) was placed in 5% TFA in DCM overnight for deprotection. TFA was removed under reduced pressure and Azido-PEG4-NHS ester (26 mg, 6.7 nmol, 10.0 eq.), 300 μL dry DMF, and 200 μL triethylamine were added. The mixture was stirred for 4 hours at room temperature. The reaction mixture was then diluted in water, extracted to DCM twice, washed with brine three times, dried over anhydrous $Na_2SO_4$ and concentrated under reduced pressure. Silica gel column chromatography was performed with 2% methanol in DCM, slowly increasing the gradient to 10%, to get reddish brown solid 1d (2 mg, 30%). ESI—MS(+), Expected mass=1025.23, found=1025.3.

Sample preparation See Table 1 for detailed sequence information. Strands $D_V$, $D_T$ and $D_A$ form Voltair$^{PM}$, $D_V$ and $D_A$' form Voltair$^{IM}$ and Voltair$^{TGn}$, $D_V^{RE}$, $D_A^{RE}$ and $D_{Tf}$ forms Voltair$^{RE}$.

TABLE 1

Sequences used for Voltair probe assemblies.

| SEQ. No | Strand | Sequence (5' to 3') | Notes |
|---|---|---|---|
| 1 | $D_V$ | ATCAACACTGCACACCAGACAGCAAGATC CTATATATA-voltage-sensing fluorophore | Sensing stand - voltage-sensing fluorophore is ispacer 18 DBCON conjugated to RVF |
| 14 | $D_T$ | membrane-anchoring group - TATATATAGGATCTTGCTGTCT | Targeting strand - the membrane-anchoring group is DBCO-TEG conjugated to POPE |
| 2 | $D_A$ | reference label - GGTGTGCAGTGTTGAT | Normalizing strand - PM reference label is ATTO™647N |
| 3 | $D_A$' | TATATATAGGATCTTGCTGTCTGGTGTGC AGTGTTGAT-reference label | Normalizing strand - Intracellular Membrane (IM) reference label is ATTO™647N |
| 5 | $D_V^{RE}$ | voltage-sensing fluorophore-TATATATAGGATCTTGCTTCTGTGCCTGC AGTGTTGAT | RE sensing strand - voltage-sensing fluorophore is RVF conjugated to DBCO-TEG ispacer 18 |
| 6 | $D_A^{RE}$ | reference label-ATCAACACTGCAGGCACAGAGTCTGGTG | RE normalizing stand reference label is ATTO™647N |
| 7 | $D_{Tf}$ | CACCAGACAGCAAGATCCTATATATAGGG GGA**U**C**AAU**CC**AAGGGA**CCC**GGAAA**C**G**CU CCCUU**ACA**CCCC | RE targeting strand - modified with RNA aptamer. The portion of sequence that is underlined corresponds to RNA aptamer against hTfR; bold letters indicate 2' fluoro modified bases. |

Sensing domain ($D_V$, $D_V^{RE}$): DBCO modified single stranded DNA was conjugated to RVF using a previously reported copper free click chemistry protocol (FIG. 6). 10 μM of the 3'-DBCO modified 38 base strand (IDT, USA) was coupled to the azide containing RVF (50 μM, 5 eq.) in 20 mM sodium phosphate buffer, pH 7.4. The reaction mixture was stirred for 4 hours at room temperature (RT). Upon completion, unconjugated fluorophores were removed by ethanol precipitation. RVF conjugated DNA was reconstituted in 10 mM phosphate buffer, pH 7.4 and the final concentration was quantified using UV absorbance at 260 nm.

Figure 6:
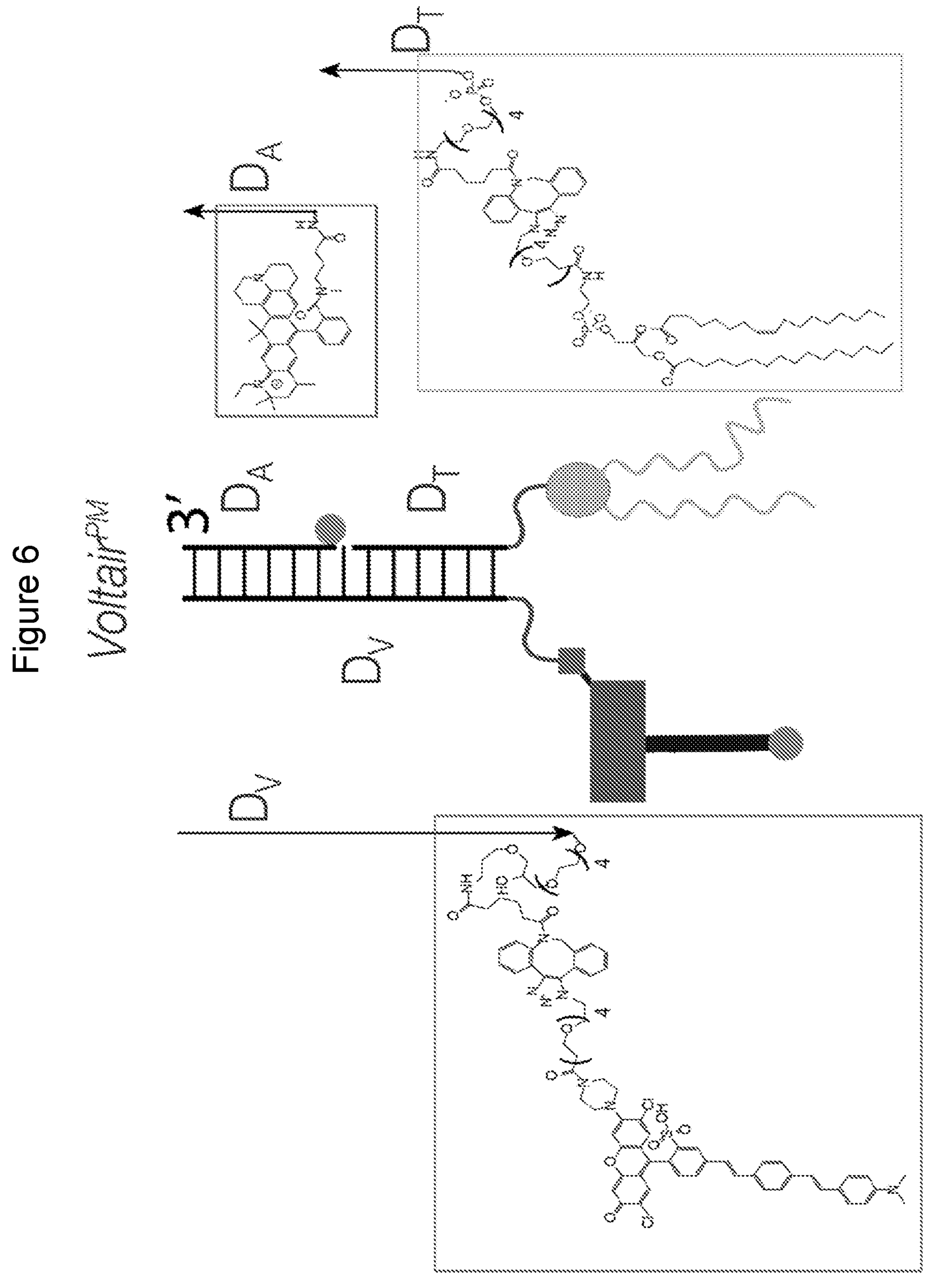
FIG. 6 illustrates components of Voltair$^{PM}$. Voltair$^{PM}$ is a trimeric complex comprising of voltage sensing strand $D_V$, normalizing strand $D_A$ and targeting strand $D_T$. $D_V$ is constructed by coupling RVF-$N_3$ to DBCO-ispacer18-DNA. $D_A$ strand is an ATTO™647N modified at 5' end of DNA. $D_T$ is constructed by coupling POPE-$N_3$ to DBCO labeled DNA. These individual strands are assembled to form the complete sensor.

Targeting domain ($D_T$): 1-palmitoyl-2-oleoyl-sn-glycero-3-phosphoethanolamine (POPE) was conjugated to NHS-PEG4-Azide using an established protocol. 20 μM of the 5'-DBCO modified 22 base strand (IDT, USA) was coupled to azido-POPE (40 μM, 2eq.) in 20 mM sodium phosphate buffer, pH 7.4 and stirred for 4 hours at RT (FIG. 6).

Construction of Voltair$^{PM}$ Voltair$^{IM}$ and Voltair$^{RE}$: Stock solution of Voltair$^{PM}$ was prepared at a final concentration of 10 μM by mixing $D_V$, $D_T$ and $D_A$ (ATTO™647N-5' modified strand) at an equimolar ratio in 10 mM sodium phosphate buffer, pH 7.4 (FIG. 6, 7). For Voltair$^{IM}$ samples, $D_V$ (Voltage sensing strand of Voltair$^{P}$) and $D_A$' (ATTO™647N-3' modified 38 mer strand) were mixed at an equimolar ratio with a final concentration of 10 μM (Table R2). For Voltair$^{RE}$ samples, 10 μM of $D_V^{RE}$, $D_{Tf}$ and $D_A^{RE}$ were mixed at an equimolar ratio. For all samples, annealing was performed by heating the reaction mixture to 95° C. for 15 min and gradually cooling to RT, at 1° C./3 min. Annealed samples were equilibrated at 4° C. overnight.

Gel electrophoresis: For gel electrophoresis 15% native polyacrylamide gels were used for annealed samples. Denaturing polyacrylamide gels containing 12-15% acrylamide [38:2 acrylamide/bisacrylamide] were used for dye conjugated single strand samples. Gels were run in 1×TBE buffer (100 mM Tris. HCl, 90 mM boric acid and 2 mM EDTA, pH 8.3) at RT. Non-fluorescent samples were stained with ethidium bromide (1 μg/mL) for 10 mins prior to visualization. Samples were observed by Biorad Universal Hood II Gel Doc system (Bio-Rad Laboratories, Inc.)

Figures 8, 9:
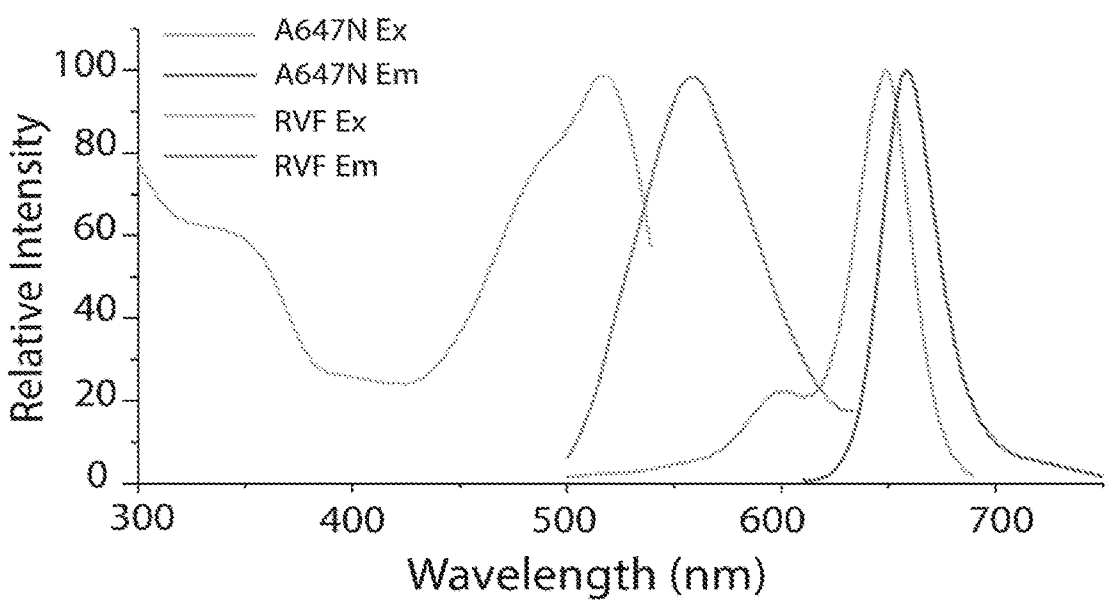
FIG. 8 illustrates spectral characteristics of Voltair probe. Normalized excitation and emission spectra of RVF and ATTO™647N. The reference dye (ATTO™647N) was chosen for the minimal overlap of its excitation spectra with the emission spectrum of the sensing (RVF) dye.
FIG. 9 illustrates RVF fluorescence characteristics are insensitive to changes in physiological pH. (A) Voltage sensing characteristics of RVF in the plasma membrane of HEK 293T cells at pH 7, 5 and 4.5 in UB4 buffer. A linear fit to each dataset is plotted. Inset shows the percentage fold change per 100 mV at indicated pH. Error bars indicate s. e. m. of n=3 experiments. (B) Normalized G/R ratios of Voltair$^{PM}$ recorded in fluorescence spectrometer in UB4 buffers as a function of pH. Error bars indicate S.D. of n=3 measurements.

In vitro spectroscopic measurements: Fluorescence spectra were recorded on a FLUOROMAX®-4 scanning Spectro-fluorometer (Horiba Scientific, Edison, NJ, USA). The Voltair$^{IM}$ was diluted to 100 nM in universal buffer, UB4 buffer (20 mM HEPES, MES and sodium acetate, 150 mM KCl, 5 mM NaCl, 1 mM $CaCl_2$ and $MgCl_2$) of desired pH for all in vitro fluorescence experiments. For recording spectra, Voltair$^{IM}$ samples were excited at 520 nm and 650 nm and emission spectra were collected between 525-600 nm and 655-750 nm respectively (FIG. 8). In order to study the pH sensitivity of Voltair probes, buffers of indicated pH (4-7) were incubated with Voltair$^{IM}$ for 30 mins prior recording. The pH sensitivity was obtained by plotting the ratio of RVF emission intensity (G, $\lambda_{Ex}$=520 nm) at 550 nm and emission intensity of normalizing dye (R, $\lambda_{Ex}$=650 nm) at 665 nm, as a function of pH (FIG. 9). Mean of G/R ratio from three independent experiments and their standard deviation were plotted for each pH value.

Cell culture, plasmids and transfection: Human embryonic kidney cells (HEK 293T), BHK-21 cells, human dermal fibroblasts (HDF), RAW 264.7, THP-1 and T-47D cells were a kind gift from Dr. Bryan Dickinson (Department of Chemistry, University of Chicago), Dr. M. Gack (Department of Microbiology, the University of Chicago), J. Rowley's lab (University of Chicago), Dr. Christine A. Petersen (Department of Epidemiology, University of Iowa), Dr. D. Nelson (Department of Pharmacological and Physiological Sciences, the University of Chicago) and G. Greene (The Ben May Department for Cancer Research, the University of Chicago), respectively. COS-7 cells were purchased from ATCC. Cells were cultured in Dulbecco's Modified Eagle's Medium (Invitrogen Corporation, USA) containing 10% heat inactivated Fetal Bovine Serum (FBS) (Invitrogen Corporation, USA), 100 U/mL penicillin and 100 µg/mL streptomycin and maintained at 37° C. under 5% $CO_2$. HEK 293T cells were passaged and plated at a confluency of 20-30% for electrophysiology experiments, and 50-70% for transfection and intracellular measurements.

The hMSR1 sequence was cloned into the PCS2NXE vector (4,103 bp) containing the CMV promoter for overexpression in mammalian cell lines. The hMSR1-CFP plasmid (5973 bp) was constructed by cloning hMSR1 sequence into pECFP-C1 plasmid (4731 bp). The identity of each construct was confirmed by sequencing, using forward primer (5' to 3') GGGACATGGGAATGCAATAG (SEQ ID NO:08) and reverse primer (5' to 3') CTCAAGGTCTGAGAATGTTCCC (SEQ ID NO:09).

The mCherry-TGNP-N-10 was a gift from Michael Davidson (Addgene plasmid #55145) and Rab7-RFP was a gift from Ari Helenius (Addgene plasmid #14436, Vonderheit & Helenius, *PLoS Biol.* 3, e233 (2005)). Construction of scFv-furin construct is reported previously by Modi et al. (*Nat. Nanotechnol.* 8, 459-467 (2013)).

HEK 293T cells were transiently transfected with respective plasmids using TransIT®-293 transfection reagent (MIRUS). After a 4-hour incubation the transfected medium was replaced with fresh medium. Labeling experiments were performed on cells 48 hours post transfection.

Figure 11:
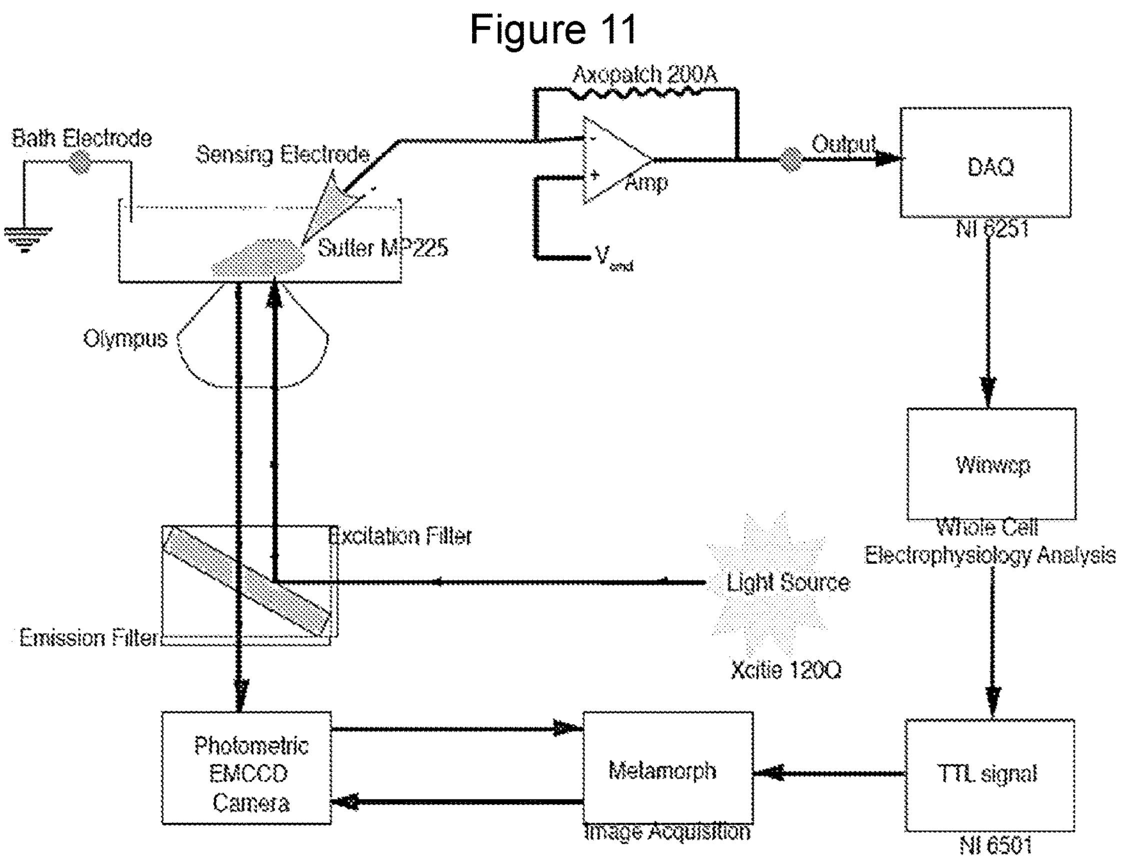
FIG. 11 illustrates optical electrophysiology set up for single cell voltage clamping. Schematic shows the equipment workflow of electrophysiology measurements. Recordings were performed with an Axopatch 200A amplifier. The signals were digitized with NI-6251 DAQ and recorded using WinWCP software (Strathclyde Electrophysiology Software). The patch pipette was positioned using MP325 motorized manipulator. Image acquisition software METAMORPH® premier Ver. 7.8.12.0 was linked to an NI-6501 to enable voltage triggered image acquisition. When applying a voltage pulse across the cell membrane a digital output pulse was generated by WinWCP to trigger imaging. Images are acquired using IX83 widefield microscope, 60×, 1.4 NA, Oil objective.

Electrophysiology: A schematic of the electrophysiology equipment used for whole cell patch clamp recording is shown in FIG. 11. Recordings of Voltair$^{PM}$ labelled HEK 293T cells were performed with an Axopatch 200A amplifier (Molecular Devices). The signals were digitized using an NI-6251 DAQ (National Instruments). The amplifier and digitizer were controlled using WinWCP software (Strathclyde Electrophysiology Software). Patch pipettes were pulled using a Sutter P-97 Micropipette puller. Borosilicate glass capillaries (Sutter) of dimension 1.5 mm×0.86 mm (OD/ID) were pulled using the program: Heat—Ramp, Pull—0, Vel—21, Time—1(Delay), Loops—5. Patch pipettes with resistances between 5-10 MOhm were used in voltage clamping experiments. The patch pipette was positioned using an MP325 motorized manipulator (Sutter). Image Acquisition software METAMORPH® premier Ver. 7.8.12.0 was linked to an NI-6501 DAQ to enable voltage triggered image acquisition. When applying a voltage pulse across the cell membrane a digital output pulse was generated by WinWCP to trigger imaging. For all measurements the extracellular solution composition was 145 mM NaCl, 20 mM glucose, 10 mM HEPES, pH 7.4, 3 mM KCl, 2 mM $CaCl_2$, 1 mM $MgCl_2$ (310 mOsm) and the intracellular solution composition was 115 mM potassium gluconate, 10 mM EGTA tetrapotassium salt, 10 mM HEPES, pH 7.2, 5 mM NaCl, 10 mM KCl, 2 mM ATP disodium salt, 300 µM GTP trisodium salt (290 mOsm).

For plasma membrane voltage clamping experiments, 1 µM RVF or 500 nM Voltair$^{PM}$ was incubated with HEK 293T cells for 30 mins in Hank's Balanced Salt Solution (Thermofisher) at room temperature. Labelled cells were washed three times with 1×PBS and incubated in extracellular solution for whole cell voltage clamping. Whole cell voltage clamping was performed according to an established protocol. Electrophysiological measurements were made from a single HEK 293T cell, without physical interaction with nearby cells to avoid interference from gap junctions. For background subtraction, bleaching correction and lamp fluctuation compensation, imaging field was chosen with at least one more HEK 293T cell that is not clamped. Once clamped, membrane potential is changed from −100 mV to +100 mV in 10 mV increments at 1000 ms intervals. Around 200 ms after the voltage is changed three images are taken in quick succession. Voltage clamp experiments were also performed with extracellular solutions of different pH, to study the effect of pH on voltage sensitivity of RVF (FIG. 9).

Figure 20:
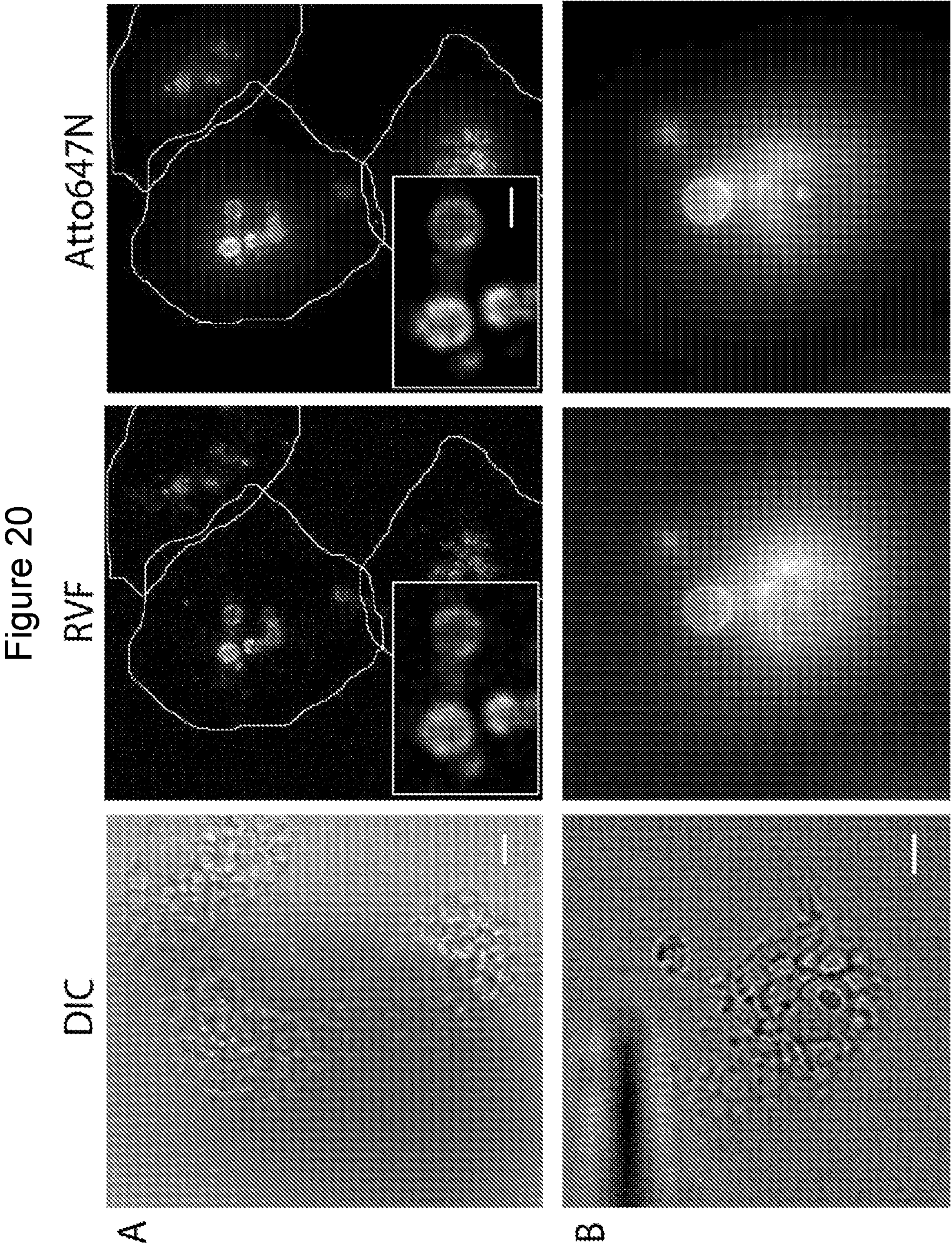
FIG. 20 illustrates isolation of enlarged lysosomes containing Voltair$^{IM}$. (A) Localization of Voltair$^{IM}$ on lysosomal membrane of Cos7 cells treated overnight with 1 μM Vacuolin-1. (B) Isolation of Voltair$^{IM}$ containing endolysosome using patch pipette for voltage clamping experiments. Scale: 5 μm.

Endo-lysosomal electrophysiology: COS-7 cells were treated with 1 µM vacuolin-1 overnight to increase the size of lysosomes to 1-3 µm. Enlarged lysosomes of COS-7 cells were labeled with 500 nM Voltair$^{IM}$, by 30 mins pulse in HBSS followed by 2 hr. chase in complete media containing 1 µM vacuolin-1 (FIG. 20). Patch pipettes used for whole cell voltage clamping, was briefly pressed against the edge of the cell and quickly pulled away in the direction perpendicular to axis of pipette to rupture the cell membrane. Enlarged endolysosome containing Voltair$^{IM}$ was pushed out of the ruptured cell using the same patch pipette (FIG. 20). Borosilicate glass capillaries (Sutter) of dimension 1.5 mm×0.86 mm (OD/ID) were pulled using the program: Heat—520, Pull—0, Vel—20, Time—200, Loops—4. Fire polished patch pipettes with resistances between 15-20 MOhm were used in voltage clamping experiments. After giga-ohm seal formation, break in was performed by a zap protocol (5V: 0.5-5 s) till appearance of capacitance transients. In order to minimize fluorescence interference from other lysosomes, patched lysosome is moved away from the cell prior to imaging. For all measurements the cytoplasmic solution composition was 140 mM K-gluconate, 4 mM NaCl, 1 mM EGTA, 20 mM HEPES, pH 7.2, 0.39 mM $CaCl_2$, 2 mM $MgCl_2$, 2 mM ATP disodium salt, 300 µM GTP trisodium salt and the composition of pipette solution was 145 mM NaCl, 2 mM $CaCl_2$, 1 mM $MgCl_2$, 10 mM HEPES, 10 mM MES pH 4.6, 10 mM glucose, 5 mM KCl. The voltage clamping and imaging protocol was followed as discussed in electrophysiology section above.

Microscopy: Wide field microscopy was carried out on an IX83 inverted microscope (Olympus Corporation of the Americas, Center Valley, PA, USA) using either a 100× or 60×, 1.4 NA, DIC oil immersion objective (PLAPON, Olympus) and EVOLVE® Delta 512 EMCCD camera (Photometrics, USA). Filter wheel, shutter and CCD camera were controlled using METAMORPH® premier Ver 7.8.12.0 (Molecular Devices, LLC, USA). Images on the same day were acquired under the same acquisition settings (exposure 100 ms and EM gain at 100 for ATTO™647N, exposure 200 ms and EM gain 300 for RVF). All the images were background subtracted by taking mean intensity over an adjacent cell free area. The mean intensity in each endosome/lysosome was measured in the sensing channel (G) and the normalizing channel (R). Filter sets, purchased from Chroma, suitable for each fluorophore were selected to minimize excitation and emission from other dyes in the sample. RVF channel images were obtained using 500/20 band pass excitation filter, 535/30 band pas emission filter and 89016 dichroic. For ATTO™647N, images were obtained using the 640/30 band pass excitation filter, 705/72 band pass emission filter and 89016 dichroic. Pseudo-color images were generated by calculating the G/R ratio per pixel in Fiji using the Image calculator module. For cytosolic calcium recording, fluorescence of Fluo-4 was recorded by exciting at 480 nm and collecting emission at 520 nm. Images were acquired using a 480/20 band pass excitation filter, 520/40 band pass emission filter and 89016 dichroic.

Figure 21:
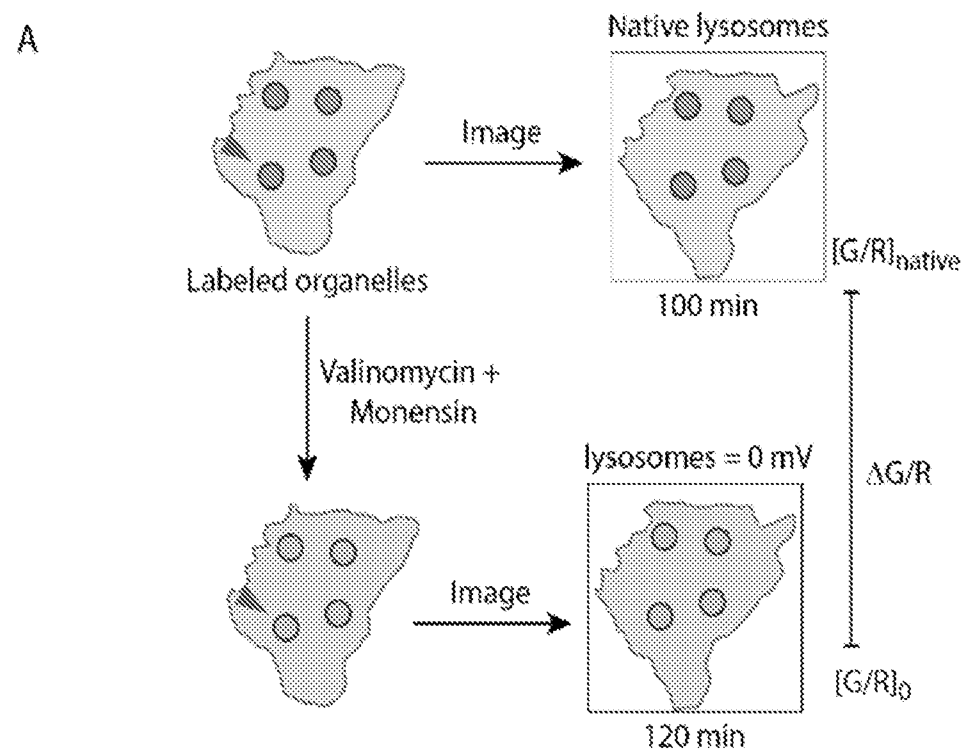
FIG. 21 illustrates measurement of organelle membrane potential using lysosomes as an example. (A) Schematic of imaging protocol of organelles labeled with Voltair$^{IM}$. Native organelles are imaged in G and R channels, neutralized with valinomycin-monensin cocktail and again imaged in the G and R channels. G/R values of native organelle membrane potential are normalized to the G/R values of neutralized organelle membrane potential (0 mV). (B) Representative images of Voltair m labeled lysosomes of the same cell in G and R channels before and after treatment with valinomycin and monensin. Corresponding G/R maps of native and neutralized lysosomes display the membrane potential of each lysosome has increased after treatment.
Figure 21:
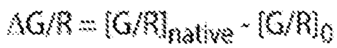
Figure 21:
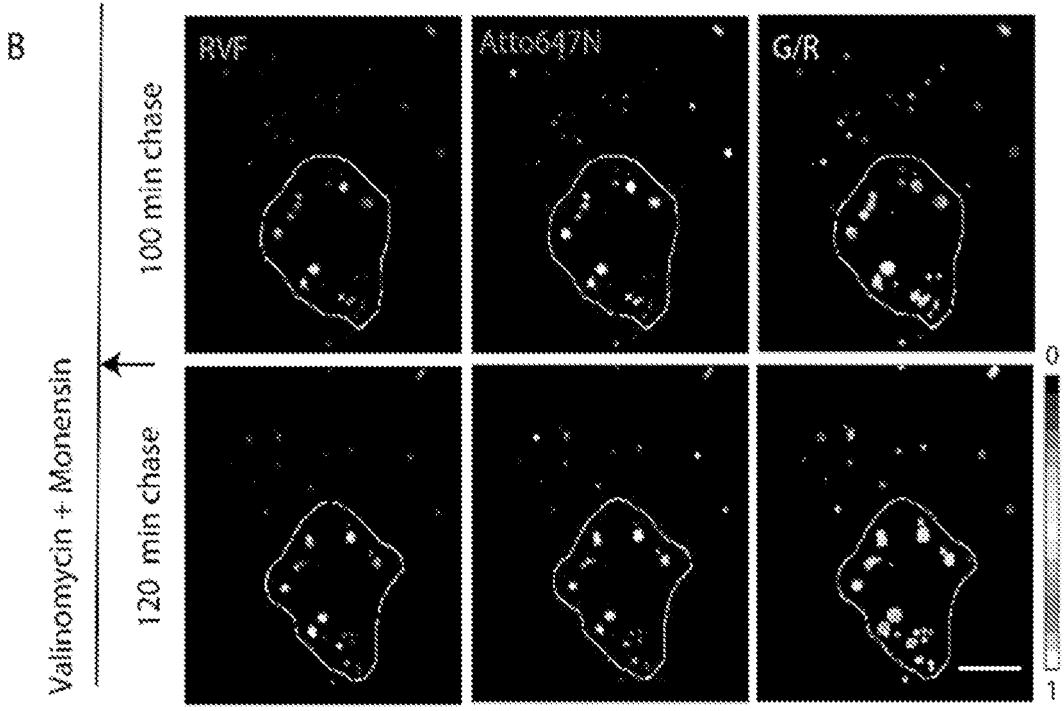

Intracellular membrane potential measurements were performed by recording images in the sensing channel (G) and the normalizing channel (R) in cells where each specific compartment was labeled. After acquisition of G and R images, intracellular membrane potential was neutralized (~0 mV) by adding 50 μM valinomycin and monensin in high $K^+$ buffer, for 20 mins at room temperature. A set of G and R images of same cells were acquired after valinomycin and monensin or pharmacological treatments as shown in FIG. 21. These images of neutralized endosomes were used as a baseline measurement to correct for variations in autofluorescence. To record all endo-lysosomal compartments in the cell, Z-stacks (30 planes, Z distance=0.8 μm) were captured and a maximum intensity projection was used to produce a single image for analysis.

Confocal images were captured with a LEICA® TCS SP5 II STED laser scanning confocal microscope (LEICA® Microsystems, Inc. Buffalo Grove, IL, USA) equipped with a 63×, 1.4 NA, Oil immersion objective. RVF was excited using an argon laser with 514 nm wavelength, CFP by 458 nm and ATTO™647N using a He—Ne laser with 633 nm wavelength. CELLMASK™ orange stain was excited by 543 nm and all emissions were filtered using Acousto Optical Beam Splitter (AOBS) with settings suitable for each fluorophore and recorded using hybrid detectors (HyD).

Time lapse Imaging: Lysosomes of COS-7 cells labeled with Voltair$^{IM}$ (FIG. 22B, C) were sequentially imaged on a widefield microscope with 60× magnification in G and R channel at 10-20s interval for a duration of 20 mins. Image acquisition was briefly paused at indicated time for addition of chemicals (ML-SA1, Baf-A1, ATP or DMSO) to cells. To minimize bleaching, time-lapse imaging was done at single focal plane. Z-drift compensator module from IX83 was applied to minimize out of focus drift during time lapse imaging. The extracellular ATP induced cytosolic calcium increase was imaged by labeling COS-7 cells with cell permeable calcium sensitive dye Fluo4-AM ester. Time-lapse imaging of Fluo-4 labeled COS-7 cells were acquired using a 480/20 band pass excitation filter, 520/40 band pass emission filter and 89016 dichroic, at 1s interval for 20 mins.

Competition assay: HEK 293T cells transfected with hMSR1-CFP were washed with 1×PBS, pH 7.4 prior to labeling with the DNA device. Cells were incubated with 20 μM maleylated BSA (mBSA) for 15 min, followed by a 20 min pulse of 500 nM DNA device and 20 μM mBSA to allow internalization by receptor mediated endocytosis. Control cells were washed and pulsed for 20 mins in 500 nM DNA device without mBSA. Cells were then washed three times with 1×PBS and chased for 30 mins in complete DMEM media. Complete media was replaced with OPTI-MEM® solution (Thermofisher) and imaged by widefield microscopy for quantification and confocal microscopy for representative images. Similar protocol was followed for other cell types shown in FIG. 14. Whole cell intensities in the ATTO™647N channel were quantified for cells expressing hMSR1-CFP observed in CFP channel. The mean intensity from three different experiments were normalized against the no mBSA control, for n~50 cells.

Figure 28:
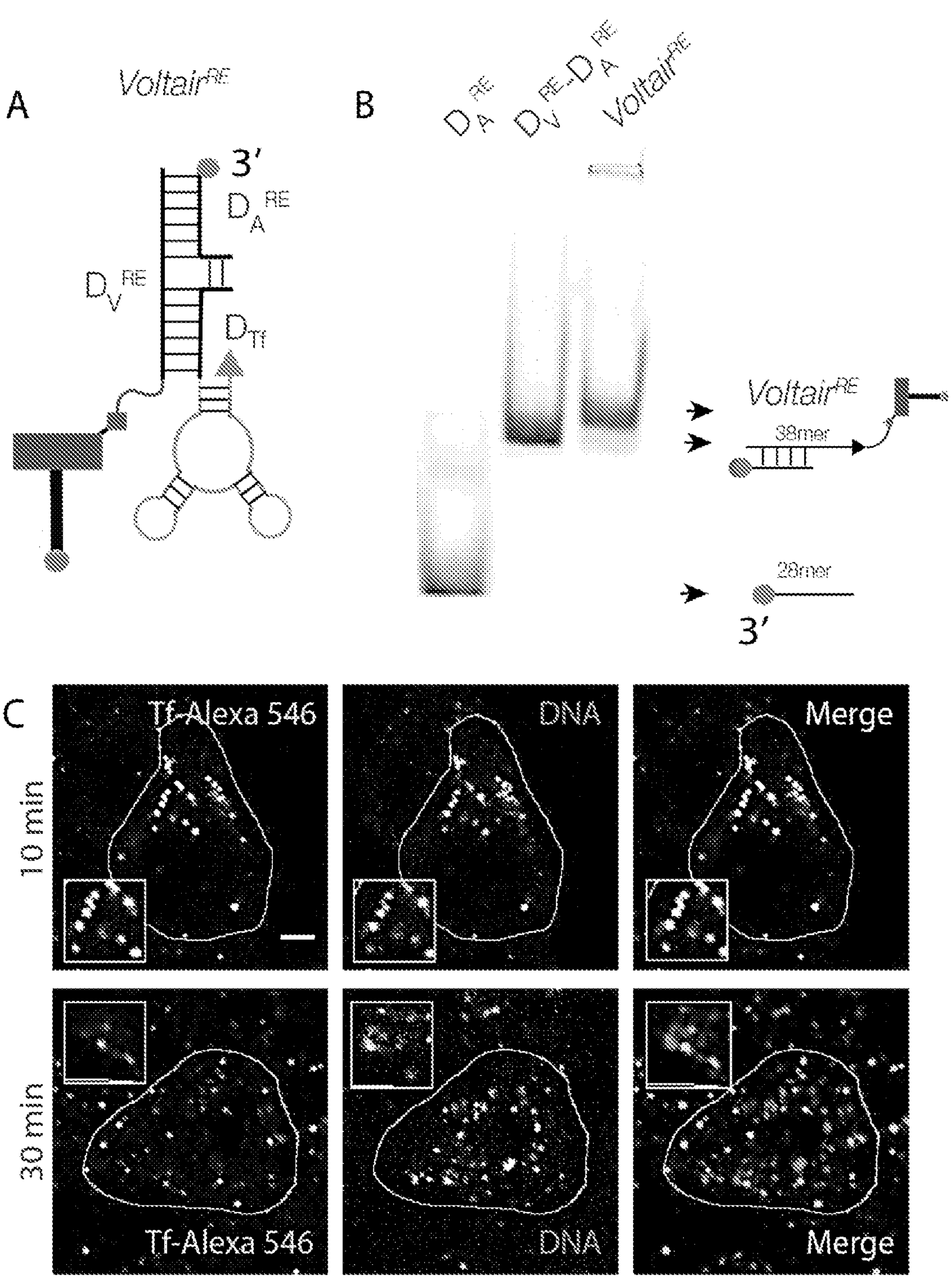
FIG. 28 illustrates characterization of Voltair$^{RE}$. (A) Voltair$^{RE}$ is a trimeric complex comprising of voltage sensing strand $D_V^{RE}$, normalizing strand $D_A^{RE}$ and targeting strand $D_{Tf}$. (B) 15% Native polyacrylamide gel electrophoresis imaged in ATTO™647N channel, showing the formation of Voltair$^{RE}$. (C) Colocalization of fluorescently labeled transferrin with early endosomes labeled by DNA-ATTO™647 duplex in 10 mins and 30 mins of chase time (Scale=5 μm).
Figure 29:
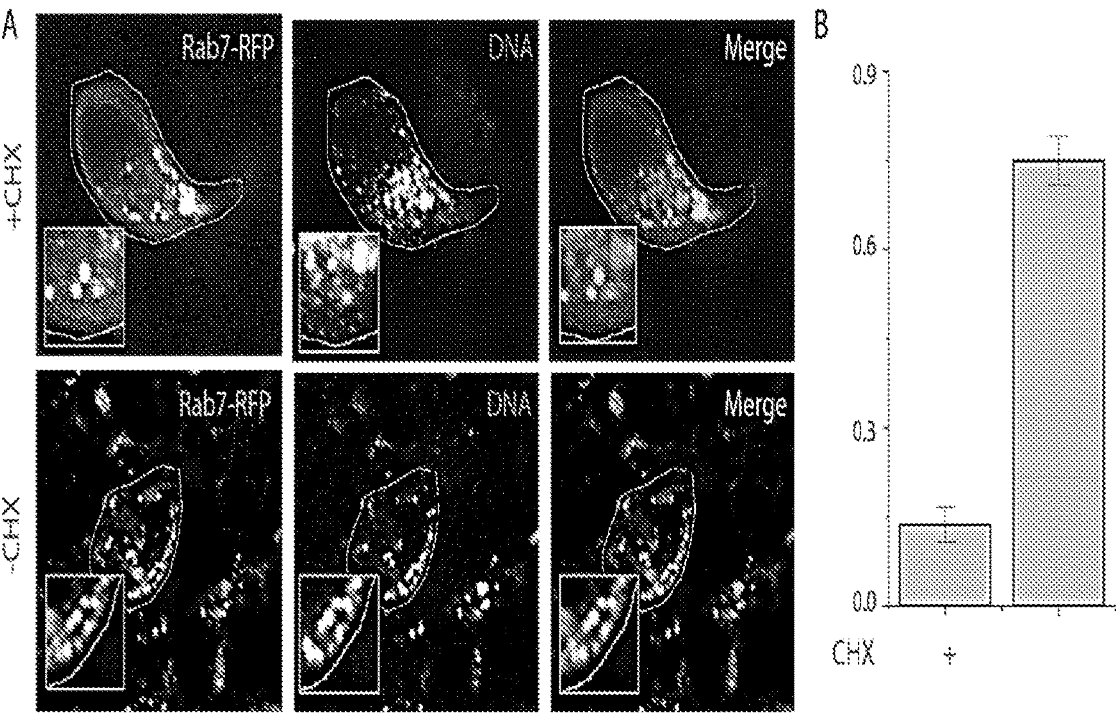
FIG. 29 illustrates trafficking of Voltair$^{TGN}$ in ScFv-Furin expressed cells. (A) Colocalization of Voltair$^{TGN}$ with late endosome marker Rab7-RFP in presence and absence of 125 μg/mL cycloheximide (CHX). (scale=5 μm). (B) Pearson's correlation coefficient (PCC) for (A). Error bar represents S.E.M of 15 individual cells.
Figure 30:
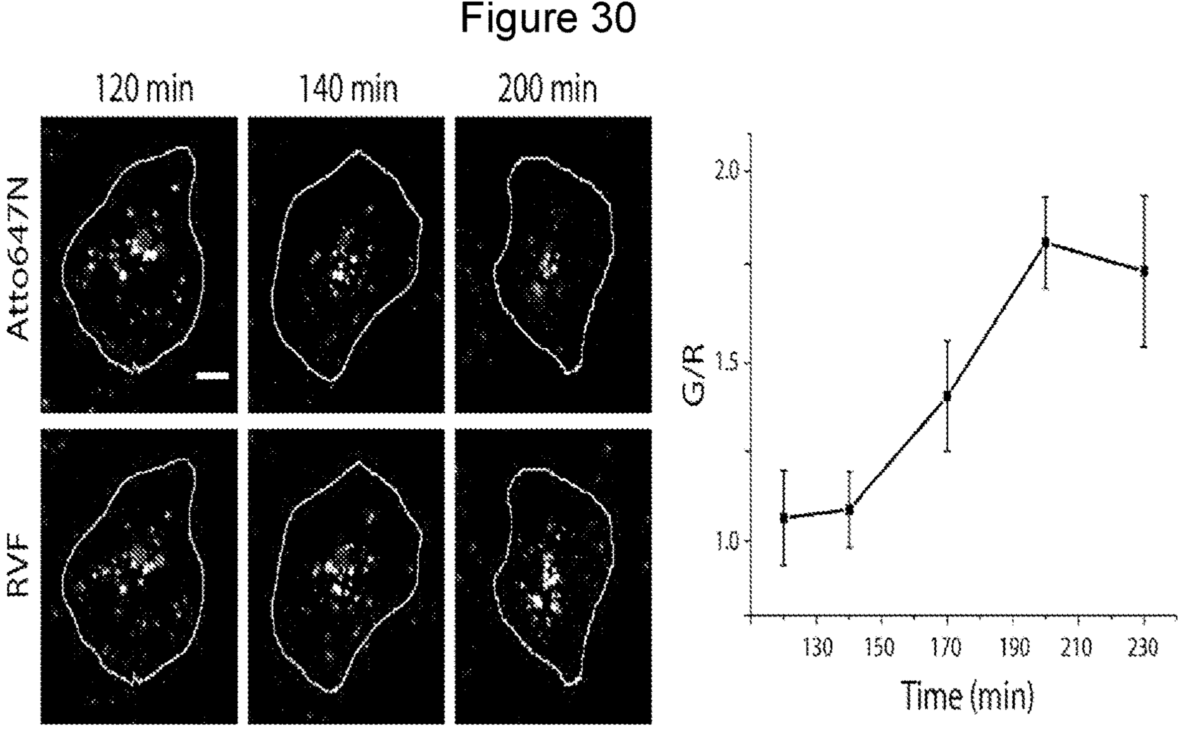
FIG. 30 illustrates stability of Voltair$^{IM}$ in HEK 293T cells. Stability is evaluated from the fluorescence intensity ratio of non-degradable, membrane impermeable RVF (G) to ATTO™647N (R), which upon DNA degradation leaks out of the endosome. The ratio of G/R as a function of chase times reveals that Voltair$^{IM}$ remains stable up to 140 minutes. Scale=10 μm, error bars indicate s.e.m. of n=3 experiments.

Co-localization and labeling experiments: In order to find out time points when internalized DNA devices specifically label different intracellular organelles, co-localization experiments with different organelle specific markers as a function of time were performed in HEK 293T cells. Transferrin receptors are known to recycle to plasma membrane via early endosome (EE) and recycling endosome (RE), therefore fluorescent Transferrin was used to specifically label EE by pulsing it for 10 minute prior to imaging and label RE with an additional chase time of 30 mins (FIG. 28). Rab7-RFP is a well-established late endosome (LE) marker, and was transiently expressed in HEK 293T cells to label LE. Transient expression of TGN46-mCherry specifically labels trans Golgi network (TGN). Finally, TMR-Dextran a specific marker for lysosome (Ly) after previously reported chase times, was pulsed for 1 hour, followed by 16 hours chase in complete media to label lysosomes.

To find out the trafficking time of DNA device in specifically labeling EE, HEK 293T cells transfected with hMSR1, were pulsed with 500 nM DNA device containing ATTO™647N for 10 minutes and chased for indicated time. These cells were also pulsed with 100 nM Tf-ALEXA FLUOR®546 for 10 mins to visualize the early endosomes. A stock solution of Tf-ALEXA FLUOR®546 was prepared according to previously established methods. Images of the ALEXA FLUOR®546 channel and the ATTO™647N channel were acquired by confocal imaging (microscopy methods) and Pearson correlation coefficient (PCC) value were calculated using Fiji plugin coloc2.

To find out the trafficking time of DNA device in specifically labeling LE or Ly, HEK 293T-hMSR1 cells were transfected with Rab7-RFP for LE or pre-pulsed & chased with TMR-Dextran for Ly. These cells were then pulsed with 500 nM DNA device for 30 mins and chased for indicated time. PCC of DNA device colocalization with EE, LE or Ly was plotted with respect to chase time. A maximum PCC value represents the time point at which DNA device is localized to the specific organelle. The trafficking time of DNA device with transferrin aptamer and $d(AT)_4$ tag in labeling RE and TGN, respectively, have been established previously. Briefly, recycling endosomes are targeted by pulsing Voltair$^{RE}$ in 1×HBSS, for 10 mins at 37° C., followed by 30 mins of chase in complete media at 37° C. Trans Golgi network is targeted by pulsing Voltair$^{IM}$ in complete media containing cycloheximide (CHX) for 90 mins at 37° C., followed by 90 mins chase in the same media.

Pharmacological drug treatments: Organelles of HEK 293T or COS-7 cells were labeled with Voltair$^{IM}$ according to labeling protocols discussed above. Labelled cells were treated with ML-SA1 (20 μM), NS1619 (15 μM) or trans-ned-19 (1 μM) for 15 mins in HBSS solution at room temperature. Torin-1 (1 μM) was treated to labelled cells during the chase period (50 mins), to inhibit mTOR. Bafilomycin-A1 (500 nM) was added to cells for 30 mins in 1×HBSS and incubated at 37C prior organellar voltage measurements. After acquisition of G and R images of drug treated cells, intracellular membrane potential was neutralized (~0 mV) by adding 50 μM valinomycin and monensin in high $K^+$ buffer, for 20 mins at room temperature. A set of G and R images of same cells were acquired after valinomycin and monensin treatment, where these images of neutralized organelles were used as a baseline measurement for internal control (FIG. 21)

Figure 3:
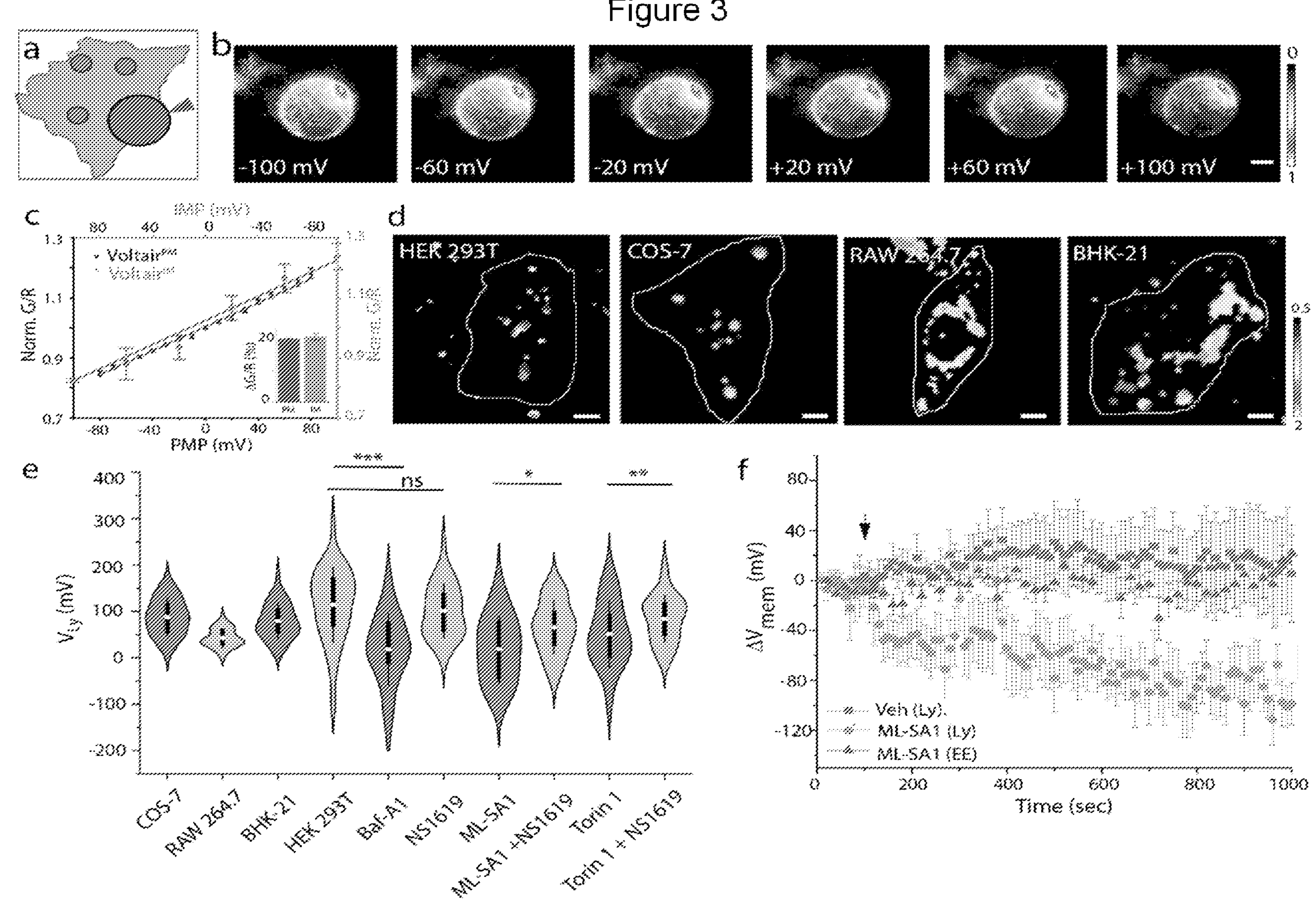
FIG. 3 illustrates Voltair$^{IM}$ measures lysosomal membrane potential. (A) Schematic showing voltage clamping of enlarged lysosome labeled with Voltair$^{IM}$. Arrowheads indicate patch pipette. (B) Images show pixel-wise G/R ratio of Voltair$^{IM}$ labelled on the inner leaflet of lysosomes as a function of membrane potential applied by whole lysosome voltage clamping. (C) Sensor response of Voltair$^{PM}$ (square) and Voltair$^{IM}$ (circle) as a function of membrane potential (PMP: Plasma membrane potential, IMP: Intracellular membrane potential). Error bars indicate mean±s.e.m. of three independent measurements. Inset: Percentage change in signal of Voltair$^{PM}$ and Voltair$^{IM}$ from 0 to 100 mV in (C). (D) Representative G/R images of the Voltair$^{IM}$ labeled lysosomes from different cell types. Scale bar=5 μm. (E) Plot of measured lysosomal resting membrane potential ($V_{Lys}$) in HEK 293T, COS-7, RAW 264.7 and BHK-21 cells and of HEK 293T $V_{Lys}$ values given by Voltair$^{IM}$ in presence of V-ATPase inhibitor Bafilomycin (Baf-A1, 500 nM), mTORC1 inhibitor Torin-1 (1 μM), the TRPML-1 activator ML-SA1 (20 μM), and the Slo1 activator, NS1619 (15 μM). Violin plots show kernel smooth distribution, box indicates interquartile range 25-75; Error bars indicate mean±s.d. of 100 lysosomes; ns, not significant (P>0.05); **P<0.01; *P<0.05 (Unpaired two sample t test). (F) Time-lapse plot of ΔVmem vs time upon TRPML1 activation in Voltair$^{IM}$ labeled lysosomes, in Voltair$^{IM}$ labeled Endosome. DMSO (Veh.) treatment, Error bar represents standard deviation from n=10 cells.

Image analysis: Images were analyzed with Fiji or imageJ (NIH, USA). For organellar voltage measurements, regions of cells containing single isolated endosomes/lysosomes in each ATTO™647N (R) image were manually selected and the coordinates saved in the ROI plugin in ImageJ. Similarly, for background computation, a nearby region outside endosomes/lysosomes were manually selected and saved as an ROI. The same regions were selected in the RVF (G) image by recalling the ROIs. After background subtraction, mean intensity for each endosome (G and R) was measured and exported to ORIGINPRO® (OriginLab, USA). A ratio of G to R intensities (G/R) was obtained from these values by dividing the mean intensity of a given endosome in the G image with the corresponding intensity in the R image. The same protocol for individual endosomes was used in the calibration, therefore G/R ratio correspond to membrane potential calibrated intracellularly. To minimize the measurement error due to low fold change of Voltair probes, the same endosomes or lysosomes are measured post addition of valinomycin and monensin which neutralizes the membrane potential in presence of 150 mM KCl. For TGN voltage measurements, total cell intensity was recorded and background subtraction was performed by manually selecting a region outside the cell. For a given experiment, membrane potential of an organelle population was determined by converting the mean $[G/R]_V$–$[G/R]_O$ value of the distribution to voltage values according to intracellular voltage calibration profile (FIG. 3C). The mean value of each organelle population across three trials on different days is determined and the final data is presented as mean±S.E.M. Representative images are shown in pseudo-color images, where G and R images were modified by thresholding in ImageJ to get G' and R' images. Using ImageJ's Image calculator module, G' images were divided by R' images to generate an image where each pixel represents [G/R]v.

For whole cell patch clamp, image analysis was performed using custom MATLAB® code. A series of images corresponding to a voltage sweep from −100 to +100 mV was collected and input into the program. By identifying changes in intensity from the first to last image a region of interest corresponding to the clamped cell was selected. Other cells present in the image were also selected based on an intensity threshold. The region containing no cells was used to subtract background noise from the detector from all regions. Intensity from unclamped cells was measured in each image and used to correct for photobleaching or fluctuation in lamp intensity. After background corrections the average intensity of the patch clamped cell was then measured for each individual image in the series and normalized against the value at −60 mV. This analysis code will be shared upon request.

Plasma membrane Cholesterol modulation: HeLa cells were incubated with either 5 mM Methyl-β-cyclodextrin (MβCD) in HBSS alone or 4.5 mM MβCD complexed with 0.5 mM cholesterol for 1 h. The former treatment depletes cholesterol levels in the plasma membrane while the latter treatment increases cholesterol levels in the plasma membrane. HeLa cells treated thus, were then labeled with $Voltair^{PM}$ in HBSS for 20 mins and voltage clamped from −100 to +100 mV and simultaneously imaged in the red and green channels.

Statistical analysis: For statistical analysis between two samples, two-sample two tailed test assuming unequal variance were used. For comparison of multiple samples, one-way ANOVA with a post hoc Tukey test or Fischer test was used. All statistical analysis was performed in Origin (Student version). Violin plots show the Kernel smooth distribution of data points and embedded box plots indicate 25-75% percentile, with median shown as white circle and error bars represents standard deviation.

Figure 7:
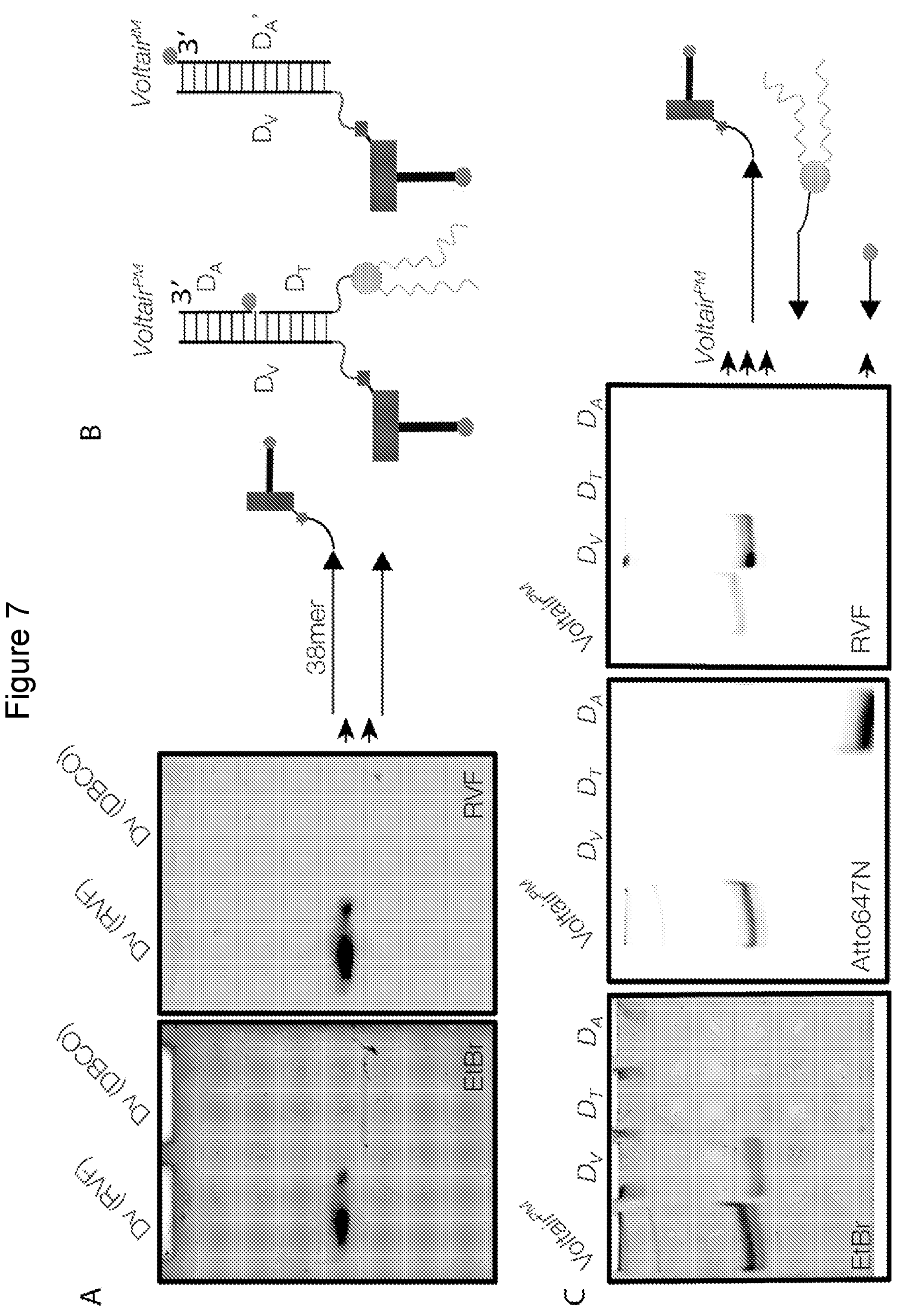
FIG. 7 illustrates gel characterization of Voltair$^{PM}$. (A) 15% Denaturing polyacrylamide gel electrophoresis in 1×TBE, showing the conjugation of RVF-$N_3$ to the DNA strand $D_V$ bearing a 3' DBCO functionality. Gels are imaged in the EtBr channel that stains DNA as well as the rhodamine channel for RVF. (B) Schematic showing the components of Voltair$^{PM}$ and Voltair$^{IM}$. (C) 15% Native polyacrylamide gel electrophoresis showing the formation of Voltair m. Gels were stained with EtBR and imaged in the EtBr, ATTO™647N as well as RVF channels.

Characterization of Voltair using gel electrophoresis. Copper free click reaction of RVF to DBCO labeled strand ($D_V$) was validated by 15% Denaturing PAGE run in 1×TBE, at 150 V. Conjugation of 1 KDa (RVF) to 10 KDa (DBCO-strand) causes the slow mobility shift of $D_V$ strand in FIG. 7. Furthermore, the lower mobility band was confirmed to contain RVF by fluorescence imaging in the rhodamine channel (excited by Epi-light and filtered by 560DF50). The $D_V$ strand was purified and hybridized with the normalizing ($D_A$) and targeting module ($D_T$) as described in sample preparation section. A 15% native PAGE was run to characterize the formation of complete sensor. In 15% acrylamide gels there is a large shift between duplex DNA and ssDNA. Under these conditions the increased persistence length of dsDNA leads to much slower mobility of $Voltair^{PM}$ with respect to single strand components ($D_V$, $D_T$, $D_A$). This therefor validates the assembly of the full sensor at high yield. It was confirmed the slower mobility band contains RVF and the normalizing dye by imaging fluorescence in rhodamine channel (RVF) and ATTO™647N channel (FIG. 7).

pH and lipid insensitivity of Voltair probes. Endocytic compartments show increasing levels of lumenal acidity along the maturation pathway, ranging from pH 6.5 at EE to pH 4.5 at Ly in mammalian cells. Most fluorescein-based probes are sensitive to acidic pH. Protonation of phenolic —OH moiety (pKa=6.4) of fluorescein-based chromophore decreases the fluorescence and hence used as well-established pH sensors. This aspect of pH interference makes it difficult to uncouple the probes ability to sense signals. Thus, a voltage sensitive dye (RVF) that could reliably sense at acidic pH was chosen. RVF comprise of dichlorosulforhodol dye, which is expected to have very low pKa due to two reasons. (i) dichlorofluorescein derivatives have lower pKa (~4.5) than fluorescein due to the negative inductive effect of chloro substitution at the ortho position of the phenolic OH. (ii) rhodol fluorophores have lower pKa than fluorescein (pKa of Rhodal=5.5). To confirm the pH independence of RVF in sensing voltage, HEK 293T cells were labeled with 1 μM RVF and voltage clamped from −100 mV to +100 mV with extracellular solutions of pH 4.5, 5 and 7 (FIG. 9). To ensure pH insensitivity of complete sensor $Voltair^{IM}$, fluorescence spectra of RVF and ATTO™647N were recorded at different pH (4.0-7.0). G/R ratios were calculated by dividing the emission spectra maxima of RVF (550 nm) to that of ATTO™647N (665 nm) and plotted with respect to pH as shown in FIG. 9.

Figure 13:
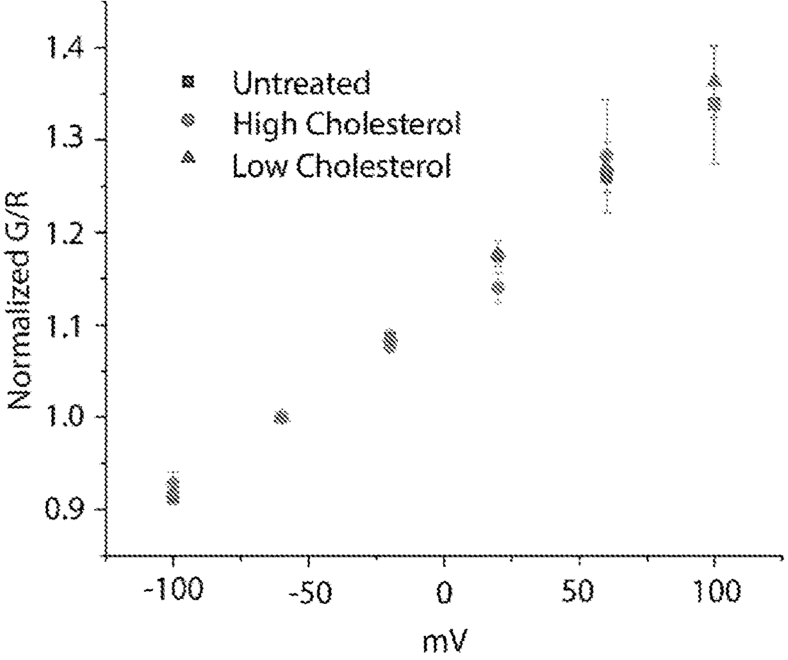
FIG. 13 illustrates RVF fluorescence characteristics are insensitive to changes in cholesterol levels. Voltage sensing characteristics, fluorescence ratio G/R w.r.t. clamped voltage −100 mV to +100 mV, of Voltair$^{PM}$ on the plasma membrane of Hela cells with altered levels of cholesterol. G/R values are normalized to −60 mV. Error bars indicate s. e. m. of n=3 experiments.

Photoinduced electron transfer (PeT) based voltage dyes are significantly different from the charge shift voltage sensitive dyes that are based on Stark shift or electrochromism. Unlike charge shift dyes, the fluorescence spectra of PeT-based dyes are expected to be insensitive to the effect of lipid composition since sulfo-fluorescein (the voltage-sensitive fluorophore in Voltair) is perched outside the outer leaflet of the plasma membrane due to anionic nature of the sulfonate group. However, to check whether this was indeed the case, experiments on $Voltair^{PM}$-labeled cells were performed and checked the response characteristics of the probe as a function of lipid composition of the plasma membrane (FIG. 13). The studies showed that Voltair performance characteristics is independent of lipid composition of the membrane, and depends strictly on the membrane potential across the membrane. Cholesterol is a major component of plasma membrane and intracellular membranes, with 35% at plasma membrane, 20% at lysosome and 10% at Golgi. The cholesterol levels on the plasma membrane of Hela cells were therefore modulated and whole cell voltage clamping from −100 mV to +100 mV was performed. Fluorescence intensity ratios (G/R) as a function of membrane potential in cells reveal that Voltair performance characteristics were insensitive to cholesterol levels in the membrane, i.e., lipid composition of the membrane (FIG. 13).

DNA-lipid conjugate labels plasma membrane: To anchor DNA based probes to the outer membrane leaflet of cell, the DNA backbone was conjugated to 1-palmitoyl-2-oleoyl-sn-glycero-3-phosphoethanolamine lipid (POPE). POPE-DNA conjugates have been previously shown to effectively label the plasma membrane of cells. For efficient insertion, the DNA duplex was coupled to POPE via tetraethylene glycol linker, providing additional flexibility and spacing (FIG. 6, 10). DNA-lipid conjugates show reversibility in anchoring due to negatively charged DNA as a hydrophilic head group. The cells were labeled with 500 nM DNA-POPE or Voltair$^{PM}$ for 20 mins at room temperature, washed the cells three times with 1×PBS and incubate the cells in extracellular buffer.

Voltair$^{IM}$ stability assay: Endo-lysosomal nucleases have been reported to degraded nucleic acids trafficked to lysosomes. In order to reliably measure membrane potential, Voltair$^{IM}$ probes must be stable at the time point when the measurement is made. The stability of Voltair$^{IM}$ was assessed by recording the fluorescence signal of RVF inside lysosomes with respect to ATTO™647N signal. Degradation of Voltair$^{IM}$ results in free RVF which docks in the inner leaflet and ATTO™647N which leaks out of the lysosome membrane. Therefore, the ratio of intensities should decrease as the DNA scaffold is degraded. Plotting G/R ratio of lysosomes with respect to time revealed that Voltair$^{IM}$ probes are fully stable up to 140 min.

Organellar membrane potential measurements: Intracellular measurements of membrane potential are performed by calculating G/R values of single endo-lysosomes. The intracellular calibration plot yields the sensitivity slope as m=0.00206±1.062E-4, using which the following equation was formulated to calculate membrane potential.

$$V = K \times (1 - G/R);\ K = 1/\text{m} = 485 \pm 25\ \text{mV};$$

The error in measurements is caused by two factors, (1) fluorescence measurement error in a recording G/R values (G/R±ΔG/R) and (2) Calibration error in whole lysosome voltage clamp. Calibration error is calculated by considering the error in measurement of K. (K±ΔK). Error analysis was performed to calculate the membrane potential error shown in Table 2.

DISCUSSION

Using a DNA-based nanodevice, called Voltair, that functions as a non-invasive, organelle-targetable, ratiometric reporter, the membrane potential can now be measured in several organelles in situ. By targeting Voltair to the endo-lysosomal pathway using scavenger receptor-mediated endocytosis, the membrane potential of the early endosome was measured, the late endosome and the lysosome in live cells. Changes in membrane potential that occur as a function of endosomal maturation can thereby be measured, which has not been previously possible. Time lapse imaging of lysosomal membrane potential upon various pharmacological treatments reveals that lysosomal membrane potential drops when cytosolic $Ca^{2+}$ is elevated.

Next, Voltair was modified to engage either the transferrin receptor or furin to target Voltair to either the recycling endosomes or the trans-Golgi network. The inventors could thus quantify the membrane potentials of these organelles in live cells. The contribution of the electrogenic Vacuolar $H^+$-ATPase (V-ATPase) proton pump to the membrane potentials of the lysosome was assessed, the recycling endosome and the trans-Golgi network, and found that different organelle membranes have distinct electrochemical characteristics.

Design and Characterization of Voltair Devices

Resting membrane potential is measured by the difference in electrical potential of two electrodes, a sample electrode inserted into the biological membrane and a reference electrode located outside the biological membrane of interest (FIG. 1A). The DNA nanodevice Voltair, uses a similar concept, where the fluorescence of a reporter probe inserted into the biological membrane is compared to a reference probe at a different wavelength located outside the biological membrane (FIG. 1A).

Voltair comprises a 38-base pair DNA duplex with three modules (FIG. 1A and Table 1). The first module is the measuring probe, denoted $D_V$, is a 38-mer single-stranded DNA conjugated at its 3' end to a previously characterized voltage sensing dye (RVF) which inserts into the biological membrane. The synthesis is described in Materials and Methods (FIG. 5-8). The fluorophore in RVF is quenched by photoinduced electron transfer (PeT) due to hyperconjugation with the lone pair of electrons on its dimethyl aminobenzyl moiety (FIG. 1B). When a potential difference is applied along the long axis of RVF, the local electric field modulates electron transfer, and therefore quenching, which affects RVF fluorescence. Specifically, plasma-membrane depolarization decreases electron transfer and increases fluorescence (FIG. 1A). RVF has high photostability, no capacitive load, is pH insensitive from pH 4.5-7.5, which makes it suitable to interrogate diverse membranes at different physiological pH (FIG. 9).

The second module in Voltair is the reference probe that is insensitive to membrane potential. The reference dye corrects for intensity changes due to different sensor concentrations arising from non-uniform cellular uptake or inhomogeneous probe distribution. Thus, the ratio of RVF and reference dye intensities are proportional only to membrane potential. The reference dye, ATTO™647N, is attached to the 5' end of $D_A$ and is chosen for its high photostability, minimal spectral overlap with RVF, insensitivity to pH, voltage and other ions (red circle, FIG. 1A).

Figure 10:
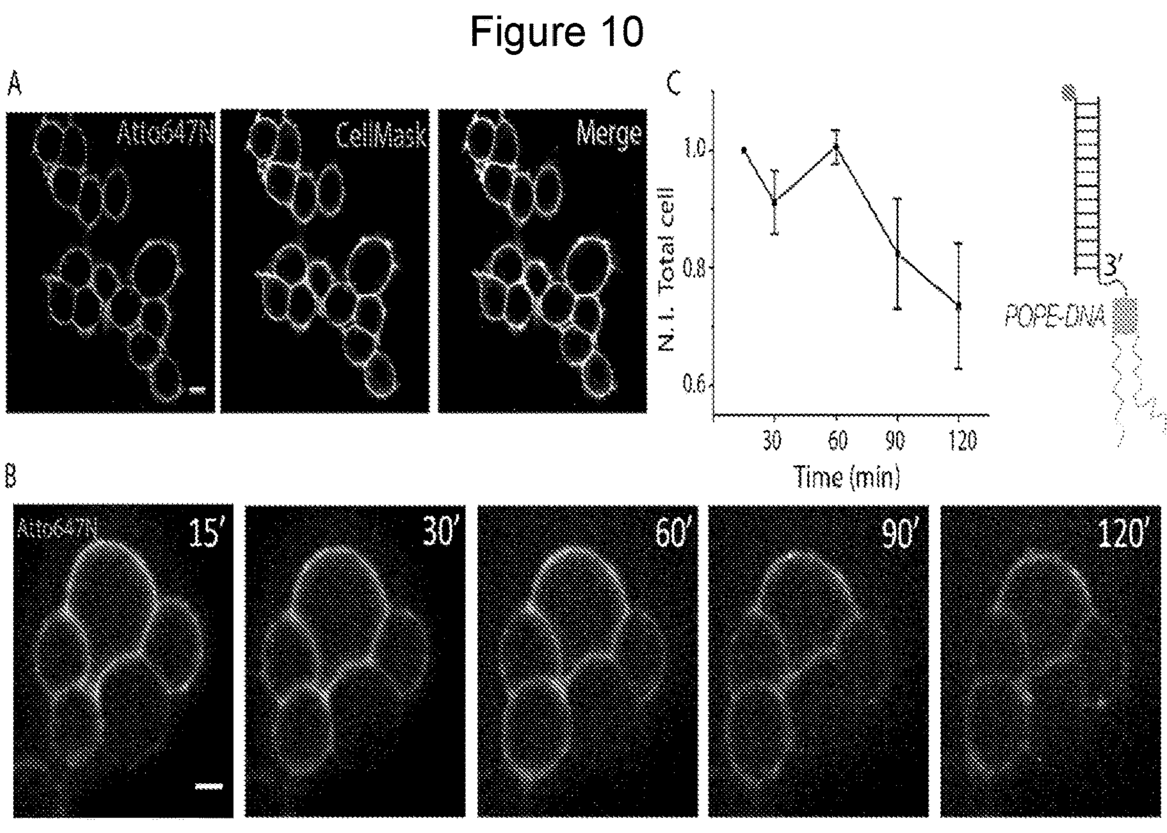
FIG. 10 illustrates plasma membrane labeling with POPE-DNA. (A) Colocalization of Voltair$^{PM}$ with plasma membrane marker CELLMASK™ orange in HEK 293T cells. (B) Time lapse images of HEK 293T cells labelled with POPE-DNA (500 nM) as a function of time shows a loss of signal only beyond 60 min. Scale=10 μm. (C) Normalized total cell intensity (N.I. Total cell) shown in (B) as a function of time. Error bar indicates S.D. of n=15 cells.

The third module in Voltair is a targeting moiety that can be changed to yield different variants for Voltair localization either at the plasma membrane, or in membranes of specific organelles. The Voltair$^{PM}$ variant has a targeting motif that localizes Voltair to the plasma-membrane by chemically conjugating the 5' end of $D_T$ to 1-palmitoyl-2-oleoyl-sn-glycero-3-phosphoethanolamine (POPE) moiety via a tetraethylene glycol linker. When Voltair$^{PM}$ is added to the culture media, the POPE moiety inserts into the outer leaflet of the plasma membrane, anchoring Voltair$^{PM}$ to the cell surface (FIG. 10). Thus, RVF is inserted in a defined orientation with respect to the membrane potential vector, and the anionic DNA duplex prevents any potential flipping of the RVF moiety in the membrane. For as long as ~2 h post-labeling, neither RVF nor DNA conjugated to POPE are endocytosed by HEK 293T cells, as these cells do not express scavenger receptors (FIG. 10, 18).

The Voltair$^{IM}$ variant labels intracellular organelles by leveraging the ability of duplex DNA to double as a ligand for scavenger receptors. The DNA-based targeting motif imposes an over-riding trafficking signal that enables Voltair internalization into a specific intracellular organelle. The DNA duplex binds scavenger receptors at the plasma-membrane and undergoes scavenger receptor-mediated endocytosis, trafficking to early endosomes, which mature to late endosomes, and finally to lysosomes, in a time-dependent manner. Both Voltair variants are assembled by annealing equimolar amounts of the component strands to yield probes with a precise 1:1 stoichiometry of the sensing dye (RVF) and reference dye (ATTO™647N). The formation and integrity of Voltair$^{PM}$ and Voltair$^{IM}$ were confirmed using gel electrophoresis (FIG. 7). The disclosure describes later in detail how the targeting motifs localize the Voltair probes selectively at the plasma membrane or inside an organelle.

Figure 12:
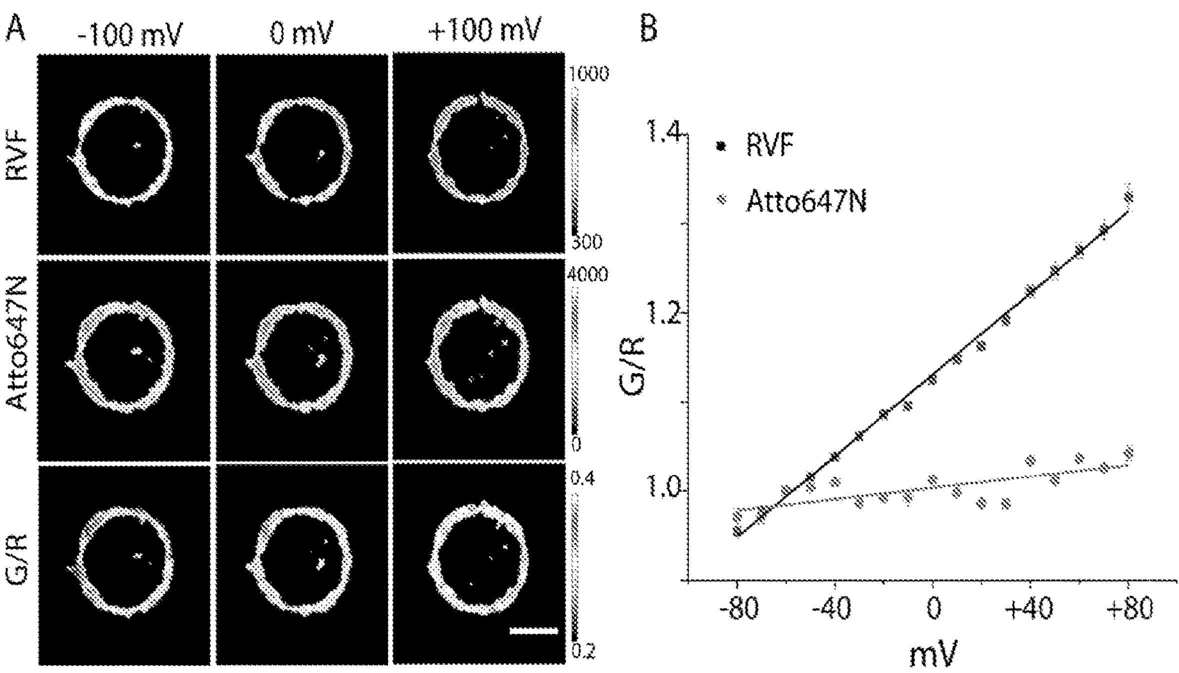
FIG. 12 illustrates voltage sensitivities of RVF and ATTO™647N in Voltair$^{PM}$. (A) Representative images of Voltair$^{PM}$ labelled HEK 293T cells voltage clamped from −100 mV to +100 mV, according to the pixel-wise fluorescence intensities of RVF (G), ATTO™647N (R) and ratio G/R. Scale bar=10 μm. (B) Normalized RVF and ATTO™647N intensities of Voltair m labelled HEK 293T cells voltage clamped from −80 mV to +80 mV. Error bars indicate s. e. m. of N=3 experiments.

The voltage-sensitive response of Voltair$^{PM}$ was first characterized using whole-cell voltage clamping using the set-up described in FIG. 11 (methods). Both Voltair$^{PM}$ and Voltair$^{IM}$ report on membrane potential by sequentially exciting RVF and ATTO™647N and monitoring their emission intensities at $\lambda_{em}$=540 nm (G for RVF) and $\lambda_{em}$=665 nm (R for ATTO™647N) (FIG. 8). The plasma membrane of HEK293T cells was efficiently labeled by Voltair$^{PM}$, as seen by colocalization with the membrane stain CELLMASK™ (FIG. 10). Next, single Voltair$^{PM}$ labeled cells were voltage clamped from −100 mV to +100 mV, at increments of 10 mV, and fluorescence images of RVF (G channel) and ATTO™647N (R channel) were sequentially acquired at each clamped voltage, from which the pseudo-colored G/R images were generated as described (FIG. 1C, methods). Notably, the whole-cell intensity images in the G channel of voltage-clamped cells changed as a function of the applied voltage, while the R channel was constant (FIG. 12). Unclamped cells showed negligible variation in either channel. The uniform 1:1 ratio of RVF: ATTO™647N in Voltair$^{PM}$ yield highly reproducible G/R values as a function of applied voltage as seen in the calibration plot of Voltair$^{PM}$ (FIG. 1D). The fold change in G/R signal from 0 mV to +100 mV (ΔG/R) was found to be 1.2 for Voltair$^{PM}$ which matched well with that of unconjugated RVF (FIG. 1D, inset). The charge shift voltage sensitive dyes e.g., di-4-ANEPPDHQ, that are based on Stark shift or electrochromism show changes in fluorescence as a function of lipid composition. Although RVF senses voltage by a completely different mechanism, i.e., PeT, the response characterisitics of Voltair$^{PM}$ as a function of the lipid composition of plasma membrane were checked (FIG. 13). The voltage-sensing characteristics of Voltair$^{PM}$ was indeed insensitive to lipid composition (FIG. 13). Based on the G/R value obtained for resting cells labeled with Voltair$^{PM}$, it was found that the resting potential was −50 mV, consistent with previous measurements (FIG. 1E, F).

Targeting Voltair$^{IM}$ To Membranes of Specific Endocytic Organelles

Figure 2:
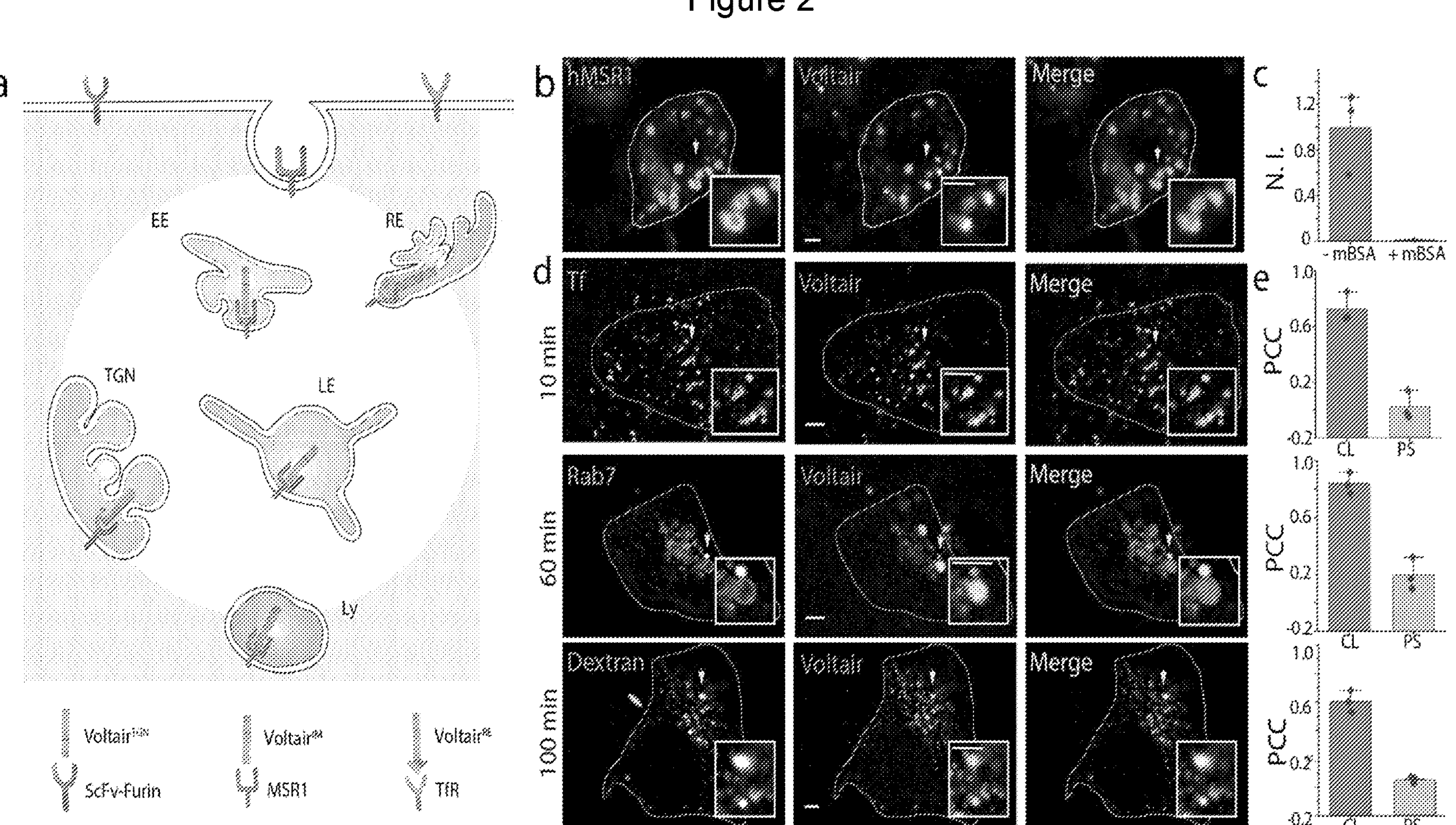
FIG. 2 illustrates targeting Voltair$^{IM}$ to membranes of specific endocytic organelles. (A) Schematic of targeting strategy: Voltair$^{IM}$ undergoes scavenger receptor mediated endocytosis by binding scavenger receptors. Endocytosed Voltair$^{IM}$ traffics in a time-dependent manner from the plasma membrane to the early endosome, the late endosome and then the lysosome. (B) Colocalization between internalized Voltair$^{IM}$ and human macrophage scavenger receptors (hMSR1-CFP) transfected in HEK 293T cells. (C) Normalized intensity of Voltair$^{IM}$ uptake in cells, in absence and presence of mBSA (30 eq.) (D) Co-localization between various endocytic organelle markers and Voltair$^{IM}$ at the indicated chase times. Early endosomes are labelled with Transferrin-ALEXA FLUOR®546 (Tf), late endosomes are labelled with Rab7-mRFP (Rab7) and lysosomes are labelled with TMR dextran (Dextrans). Scale bar=5 μm. (E) Pearson's correlation coefficient (PCC) of Voltair colocalization (CL) with corresponding endocytic markers in (D) along with pixel shift (PS). Error bar represents mean±s.e.m. of three independent trials.
Figures 14, 15:
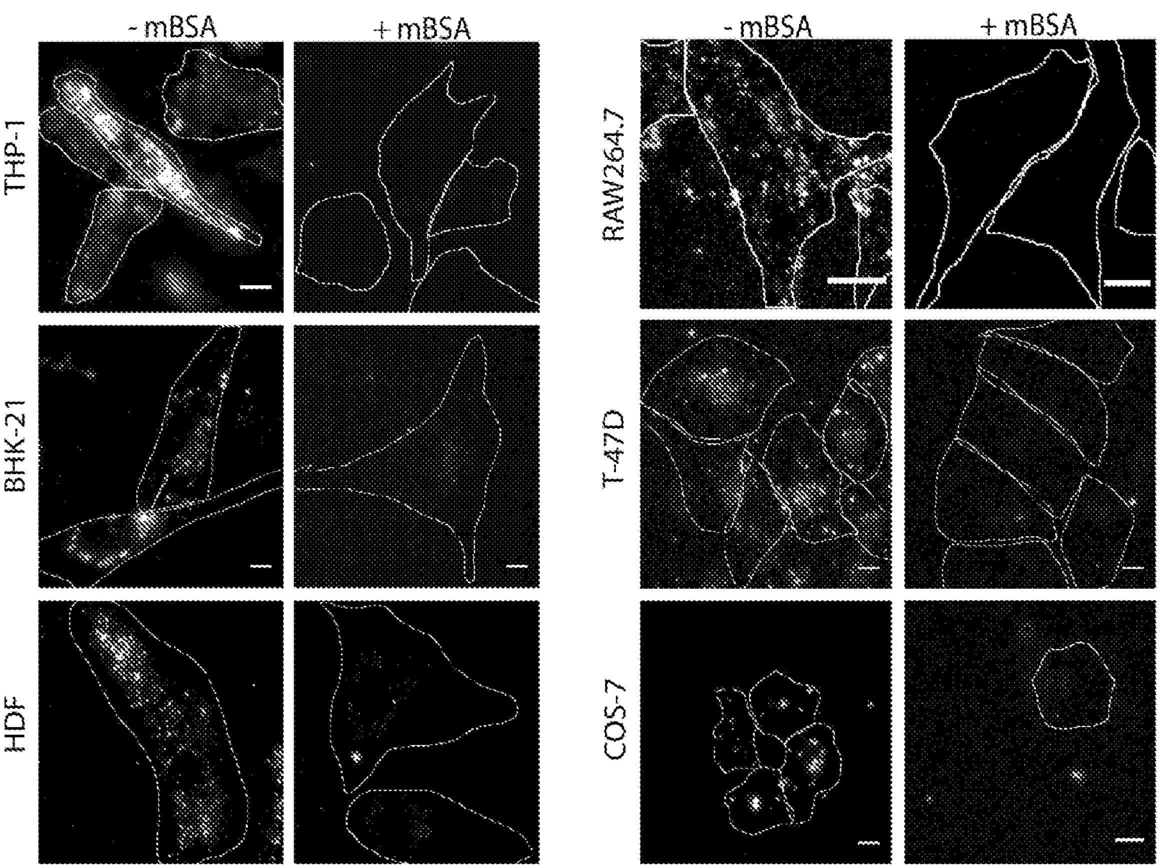
FIG. 14 illustrates DNA uptake by cell types expressing endogenous levels of scavenger receptor. Representative images of different cell lines demonstrating uptake of DNA nanodevices to intracellular compartments, via endogenous scavenger receptor. Competitive inhibition of DNA—scavenger receptor interaction with maleylated BSA, decreases uptake in these cells. THP-1: human monocyte derived cell line; BHK-21: Baby Hamster Kidney cells; HDF: Human Dermal Fibroblast primary cells; RAW 264.7: Mouse macrophage cell line; T-47D: breast cancer cell line; COS-7: Monkey kidney cell line. Scale: 10 μm.
FIG. 15 illustrates Voltair$^{IM}$ uptake by HEK cells expressing human scavenger receptor (hMSR1). (A) Upper Panels: Voltair$^{IM}$ is endocytosed by HEK 293T cells expressing hMSR1-CFP. Colocalization of hMSR1 (CFP channel) with Voltair$^{IM}$ (ATTO™647N channel) in punctate structures. Lower panels: Uptake of Voltair$^{IM}$ is efficiently competed out in the presence of maleylated BSA (mBSA) a good ligand for hMSR1. Scale bar=10 μm. (B) Pearson's correlation coefficient (PCC) of colocalization with endocytic markers as a function of Voltair$^{IM}$ chase times. Error bars indicate the standard deviation for n=50 cells.

Given the favorable reporter characteristics of Voltair$^{PM}$, the inventors then targeted the variant, Voltair$^{IM}$, in organelles along the endo-lysosomal pathway using scavenger receptor mediated endocytosis (FIG. 2A). DNA-based probes can label endocytic organelles precisely and in diverse cell types that express scavenger receptors such as THP-1 (Human monocyte cell line), RAW 264.7 (Mouse macrophage cell line), T-47D (breast cancer cell line), BHK-21 (Baby Hamster Kidney fibroblast), HDF (Human Dermal fibroblast) and COS-7 cells (Monkey kidney cells) (FIG. 14). HEK 293T cells on the other hand, do not express scavenger receptors. While this is ideal for plasma membrane immobilization of Voltair$^{PM}$, it prevents endosomal uptake of Voltair nanodevices. Therefore, human macrophage scavenger receptor (hMSR1) fused to CFP was overexpressed in HEK293T cells by transient transfection. These transfected cells effectively endocytosed Voltair$^{IM}$ through receptor-mediated endocytosis (FIG. 2B-C). Colocalization between hMSR1-CFP and Voltair$^{IM}$ indicated uptake by scavenger receptors (FIG. 2B). This was reaffirmed by competing out Voltair$^{IM}$ uptake with excess maleylated BSA, a strong ligand for scavenger receptors (FIG. 2C, 15).

Figure 16:
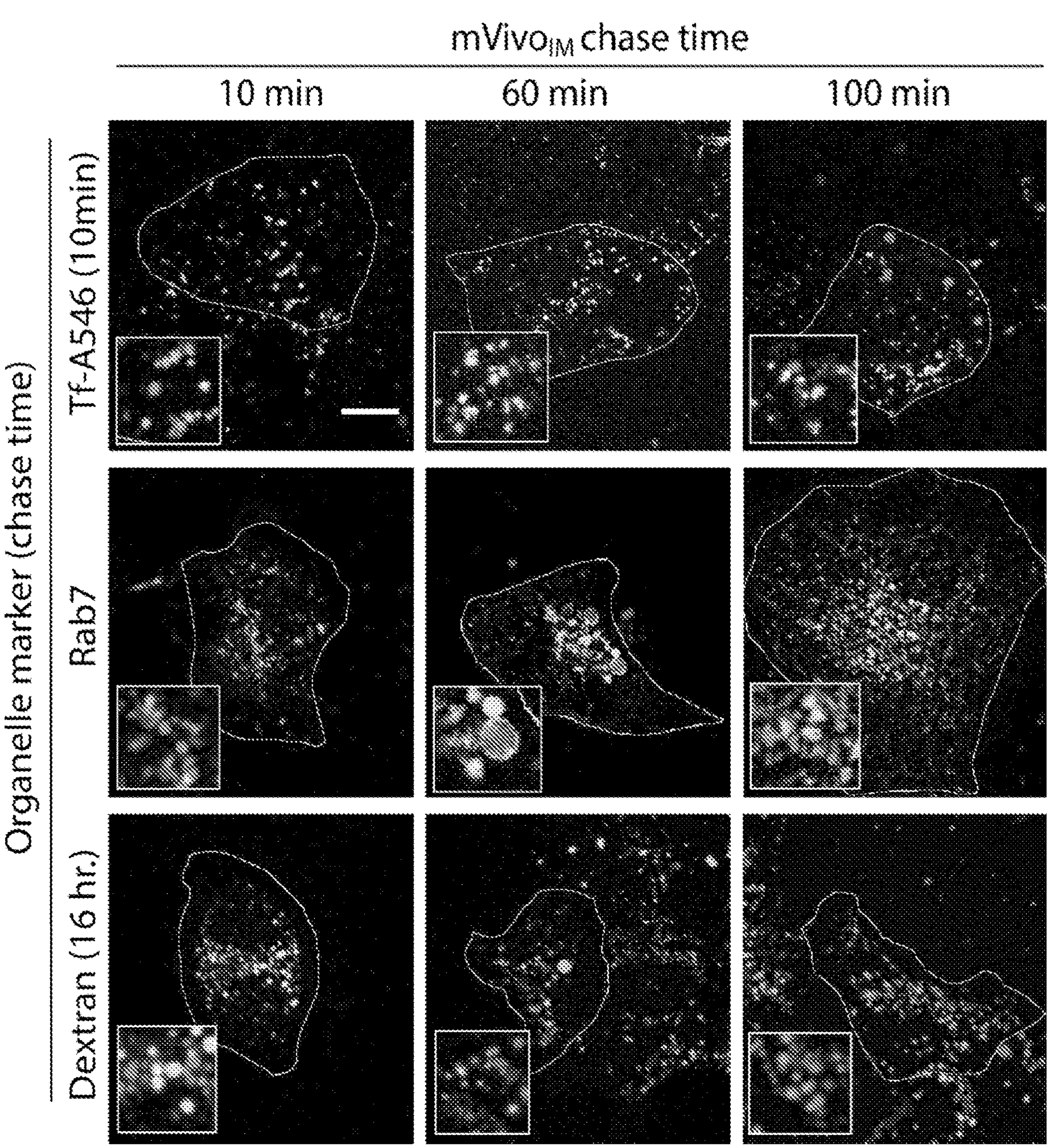
FIG. 16 illustrates time dependent trafficking of Voltair$^{IM}$. Representative colocalization of singly labeled Voltair$^{IM}$ and endosomal markers in HEK 293T cells expressing hMSR1. Early endosomes are labeled with 10 min pulse ALEXA FLUOR®546-labeled transferrin (Tf-A546). Late endosomes are labeled with Rab7-mRFP. Lysosomes are labeled by pulsing TMR-Dextran for 1 hour and chasing for 16 hours. Voltair$^{IM}$ was pulsed for 10 min and chased for indicated time and imaged accordingly. Pearson's correlation coefficients are shown in FIG. 2 of the main manuscript. Scale bar=10 μm.
Figure 17:
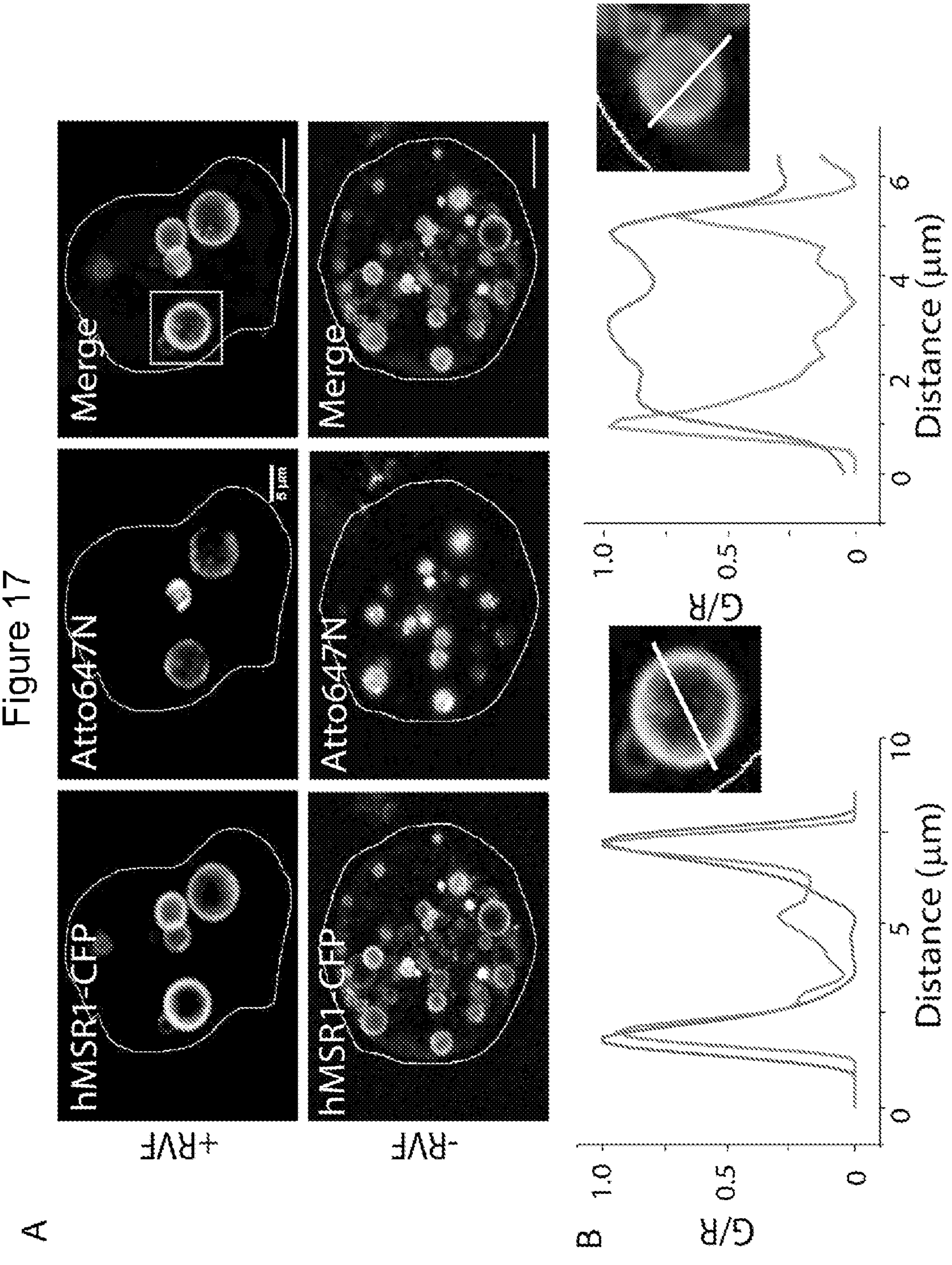
FIG. 17 illustrates Voltair$^{IM}$ inserts into the membrane of the intracellular organelle because the RVF moiety acts as a lipid anchor. (A) Vacuolin-1 treated HEK 293T cells labeled with Voltair$^{IM}$ show the DNA probe inserted into the lumenal leaflet of lysosomal membranes. When labeled with a duplex DNA lacking lipophilic RVF, the DNA probe fails to localize at the membrane. (B) Line profile of vacuolin-1 treated single lysosome shows the colocalization of DNA probe with hMSR1-CFP present on the endo-lysosomal membrane. Scale=5 μm.
Figure 18:
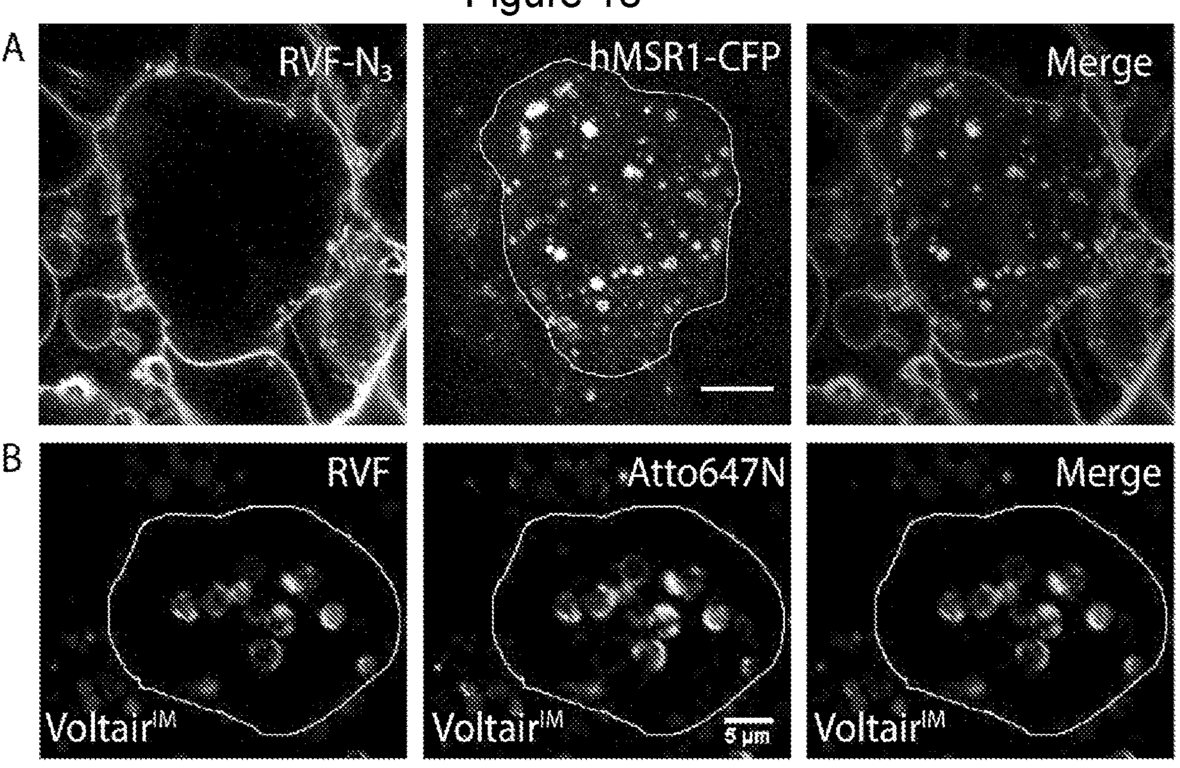
FIG. 18 illustrates conjugation to the DNA duplex reprograms the affinity of RVF to intracellular membranes. (A) Incubating RVF with hMSR1-CFP expressing HEK 293T cells results in RVF labeling only the plasma membrane. (B) RVF is conjugated to duplex DNA to give Voltair$^{IM}$. hMSR1 expressing HEK 293T cells incubated with Voltair$^{IM}$ imaged in the RVF channel and the ATTO™647N channel (DNA) shows that RVF now labels organellar membranes. Cells were treated with Vacuolin-1 to swell the vesicles in order to confirm tethering to intracellular membranes. Scale: 5 μm.
Figure 19:
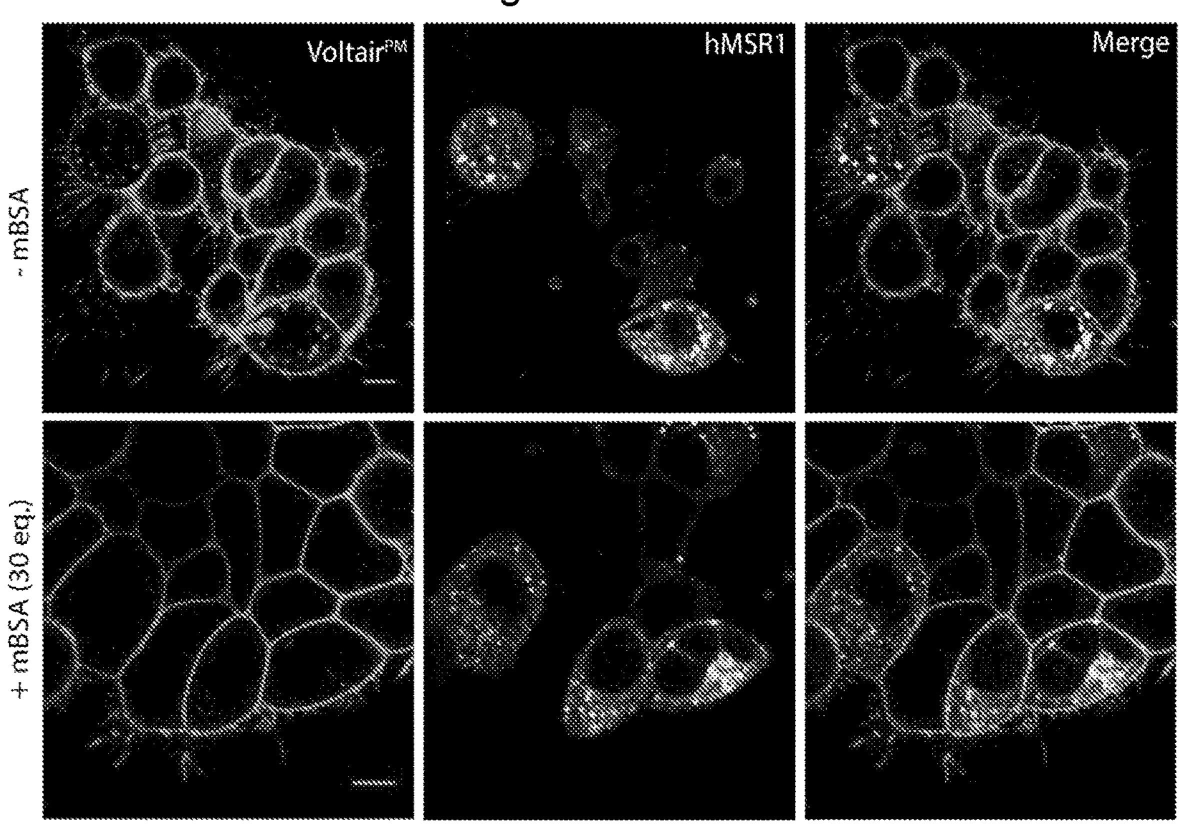
FIG. 19 illustrates maleylated BSA blocks endocytosis of Voltair$^{PM}$ in hMSR1 expressing HEK 293T cells. Representative images of Voltair$^{PM}$ localization in CFP-hMSR1 transfected HEK 293T cells, where 500 nM Voltair$^{PM}$ was pulsed and chased for 30 mins in the presence and absence of 30eq. mBSA. Scale: 10 μm.

It was then determined the timepoints of localization of internalized Voltair$^{IM}$ devices at each stage along the endo-lysosomal pathway in HEK 293T cells (FIG. 2D, E). For this, time-dependent colocalization with various endocytic markers was performed. Briefly, HEK 293T cells expressing hMSR1 were pre-labeled with endocytic markers i.e., ALEXA FLUOR®546-labeled transferrin, Rab7-mRFP and TMR-Dextran, that each specifically labeled early endosomes, late endosomes or lysosomes, respectively. These cells were then pulsed with singly-labeled Voltair$^{IM}$. Colocalization was monitored as a function of different chase times (FIG. 2D, 16). The inventors found that Voltair$^{IM}$ localized in early endosomes at ~10 min, in late endosomes at ~60 min, and in lysosomes at ~100 min. In Voltair$^{IM}$, the RVF moiety functions both as a voltage sensitive dye as well as a lipid anchor that tethers Voltair$^{IM}$ to the lumenal face of the organelle membrane (FIG. 17). In parallel, the duplex DNA moiety allows scavenger receptor binding and also allows RVF insertion into the intracellular membrane surrounding the receptor, and therefore overrides the affinity of RVF to the plasma membrane (FIG. 18). Thus, integration onto a duplex DNA scaffold successfully imposes the scavenger receptor-mediated endocytic program on to RVF (FIG. 18B, 19).

Calibration of Voltair Probes in Intracellular Organelles

Next, the response characteristics of Voltair in intracellular membranes was mapped. To achieve this, whole endo-lysosomal voltage clamping was performed while simultaneously imaging Voltair$^{IM}$ ratiometrically on the inner leaflet of lysosomal membrane. Treating COS-7 cells with vacuolin-1 swells up lysosomes to sizes of 1-3 μm. Vacuolin-1 treated COS-7 cells were labelled with Voltair$^{IM}$ as described in methods (FIG. 20A). The Voltair$^{IM}$ labeled enlarged lysosomes were isolated using a patch pipette and voltage clamped from −100 mV to +100 mV (FIG. 20B, FIG. 3A). Fluorescence images of RVF (G) and ATTO™647N (R) were acquired sequentially at each indicated clamped membrane potential and an intra-organellar calibration plot of normalized G/R versus membrane potential was constructed (FIG. 3B, C). The calibration plot of Voltair$^{IM}$ in lysosomes showed 20%-fold change per 100 mV, quantitatively recapitulating its voltage-sensing characteristics in the plasma membrane (FIG. 3C, inset). The intra-organellar calibration profile of Voltair$^{IM}$ was used to compute the membrane potential in all subsequent experiments.

In Situ Measurement of Absolute Lysosomal Membrane Potential

Figure 22:
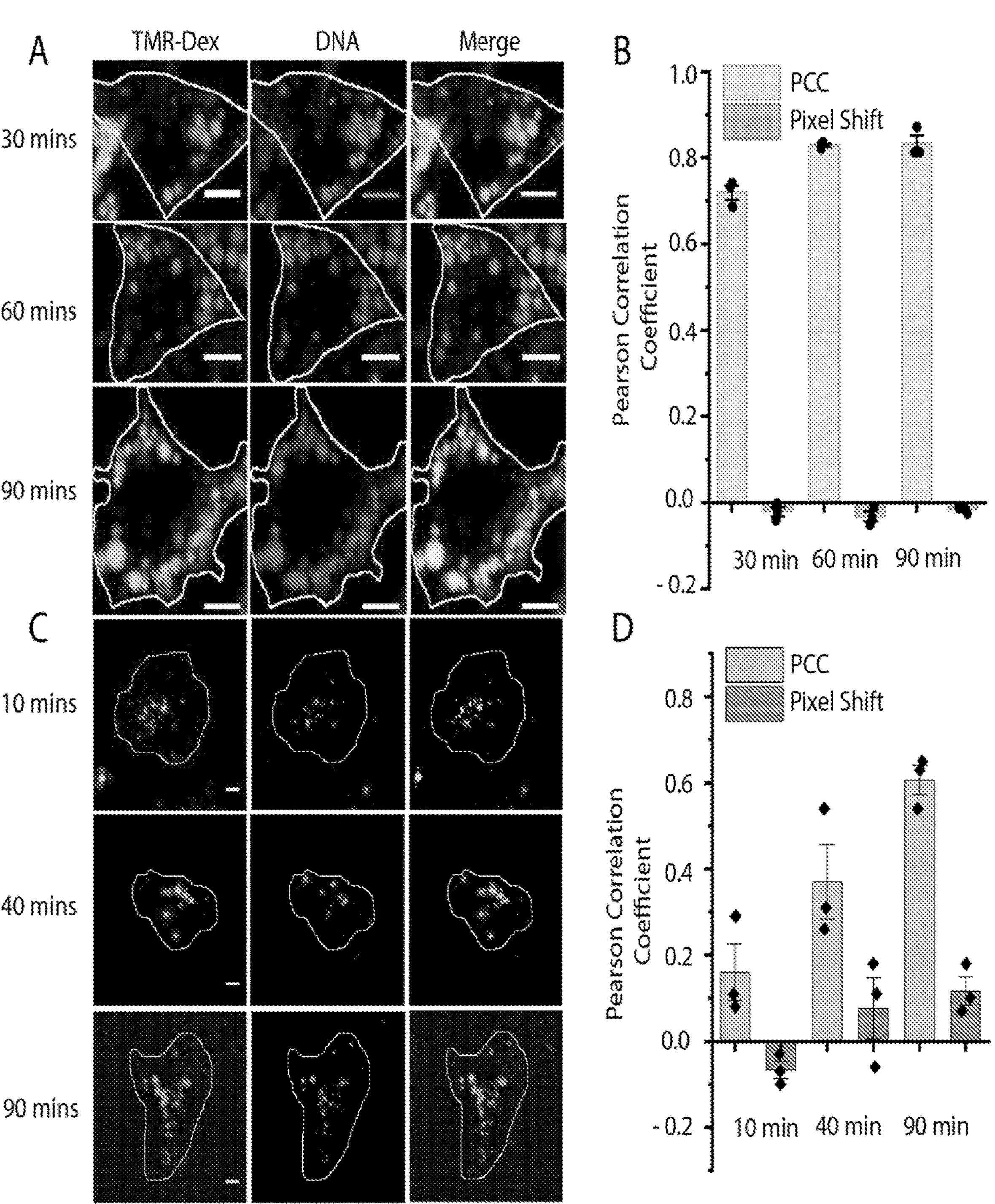
FIG. 22 illustrates targeting DNA nanodevices to lysosomes in RAW 264.7 and COS-7. (A) Representative colocalization of DNA {red}chased at indicated time and lysosomal marker in Raw 264.7 cells. Scale bar=10 μm. (B) Pearson's correlation coefficient (PCC) of colocalization with TMR-Dextran as a function of DNA chase times. Error bars indicate the standard error of mean for n=3 experiments. (C) Representative colocalization of DNA chased at indicated time and lysosomal marker in COS-7 cells. Scale bar=10 μm. (D) Pearson's correlation coefficient (PCC) of colocalization with TMR-Dextran as a function of DNA chase times. Error bars indicate the standard error of mean for n=3 experiments.

Voltair$^{IM}$ performance in lysosomes in situ in live cells was first validated, given that this organelle has been rigorously addressed using electrophysiology. Fluorescence images in the G and R channels of Voltair m labeled lysosomes in HEK293T cells were acquired and the pseudo-colored G/R images were computed (FIG. 3D, 21). FIG. 3E shows the distribution of G/R values in lysosomes and from the intracellular calibration plot it could be determined the corresponding membrane potential. Considering the lumen to be positive and the cytoplasmic face negative, the membrane potential of lysosomes ($V_{Ly}$) was found to be +114 mV. This is in line with other electrophysiological studies of lysosomal membrane potential in different cell types that were found to lie between −30 mV to +110 mV. The lysosomal membrane potential was then compared across different cell lines (FIG. 22). It was found that COS-7 and BHK-21 cells showed slightly lower overall values of membrane potential +80 mV (lumen positive) compared to HEK 293T cells. Those in RAW macrophages were even more depolarized with values centered at +40 mV (lumen positive), comparable to +20 mV reported in previous literature (FIG. 3D, E). Such variations in the mean resting potential in different cell types could arise from the differential lysosomal membrane protein composition across these cell types.

Figure 23:
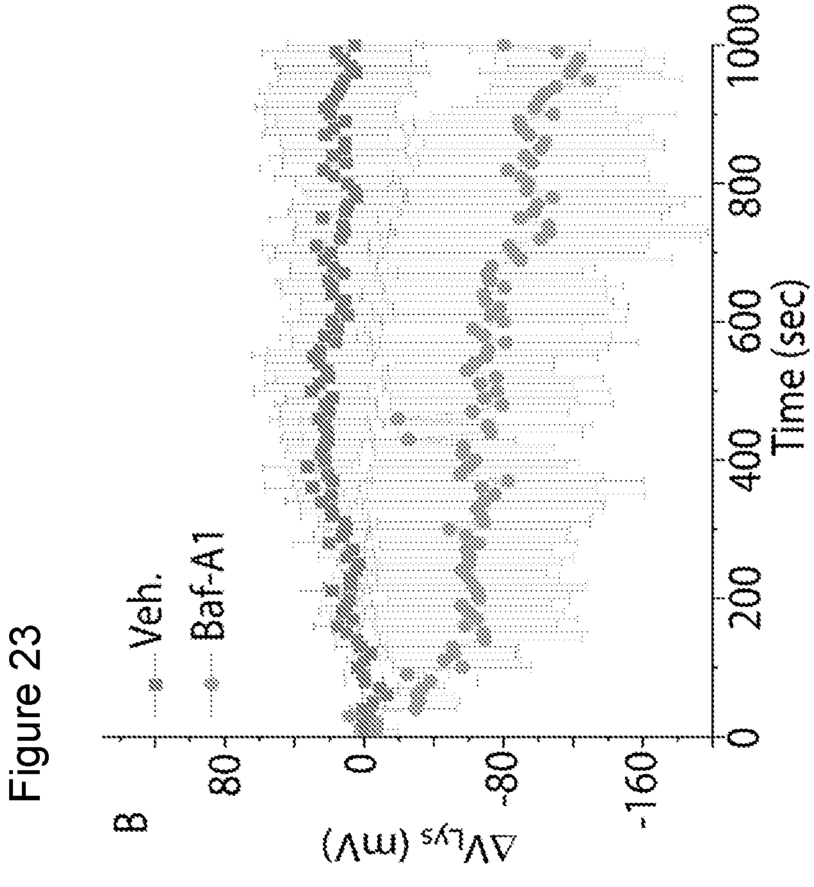
FIG. 23 illustrates Time-lapse imaging of Voltair$^{IM}$ labeled lysosome upon pharmacological treatment. (A) G/R values of Voltair$^{PM}$ labelled lysosomes in presence (Baf-A1) and absence (Veh.—DMSO) of 500 nM Bafilomycin A1. Error bars indicate mean±s.e.m. of three independent measurements; ***P<0.001 (Unpaired two sample t test). (B) Dynamic G/R vs time plot shows depolarization of lysosomal membrane potential upon V-ATPase inhibition. Error bar represents standard deviation from n=10 cells.
Figure 23:
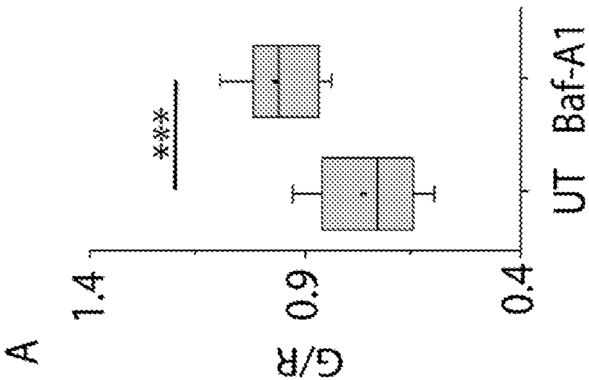

Next, whether Voltair$^{IM}$ had the sensitivity to report changes in lysosomal membrane potential upon treatment with common pharmacological reagents that activate pumps, channels and transporters on the lysosomal membrane was checked. The electrogenic proton pump V-ATPase acidifies many organelles by hydrolyzing ATP and generating membrane potential across organelle membranes. Inhibiting V-ATPase with bafilomycin A1 stops proton transport, which neutralizes membrane potential in purified, highly acidic synaptic vesicles. It was found that Voltair$^{IM}$ labeled lysosomes showed a large increase in G/R values upon bafilomycin A1 treatment (500 nM) compared to untreated cells, revealing that lysosomal membrane potential ($V_{Lys}$) was dissipated by inhibiting V-ATPase (FIG. 23). From the in-cell calibration plot (FIG. 3C), $V_{Lys}$ was reduced by ~100 mV from the resting membrane potential, consistent with studies on other highly acidic V-ATPase regulated organelles such as synaptic vesicles. (FIG. 3E, 23).

Figure 24:
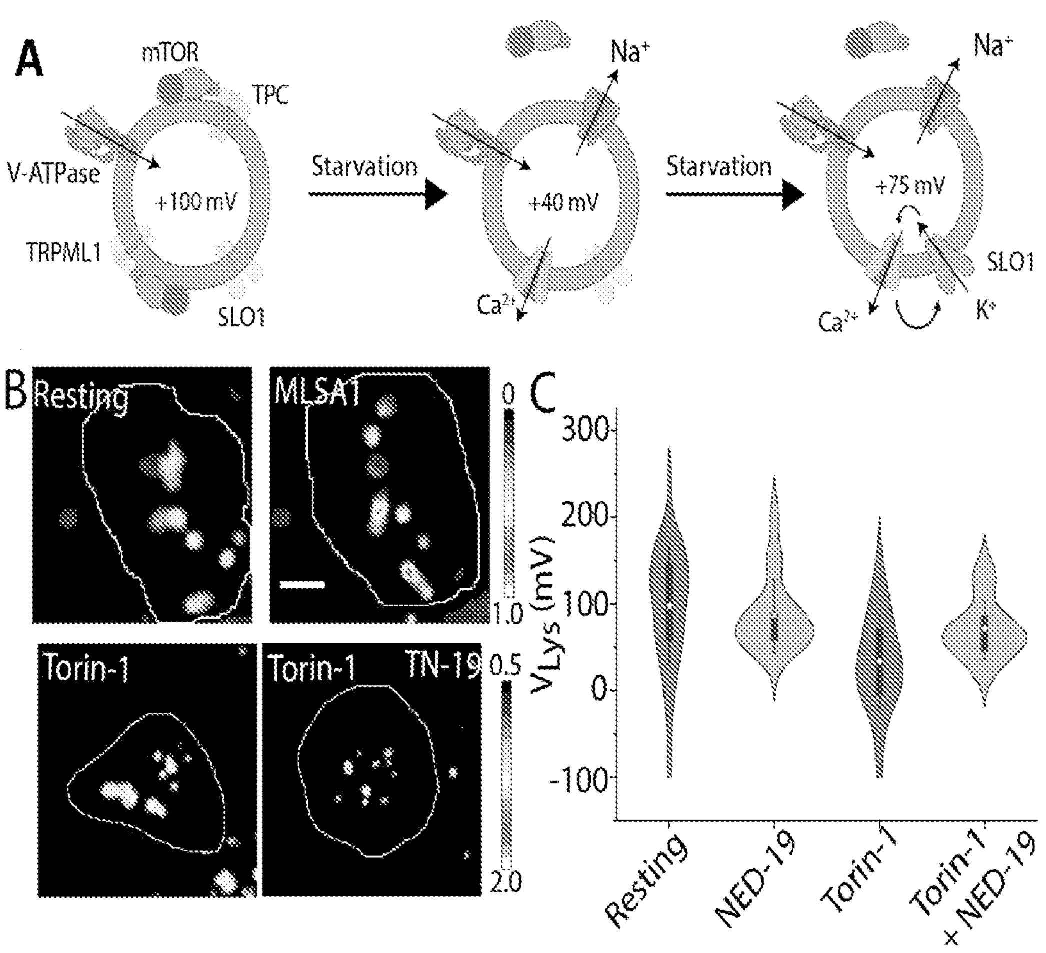
FIG. 24 illustrates lysosomal membrane potential changes under starvation. (A) Model: Starvation promotes dissociation of mTORC1 from lysosomes, activating TPC and TRPML1 channels that release cations and depolarize lysosomes. Low lysosomal membrane potential ($V_{Lys}$) as well as released $Ca^{2+}$ promote the opening of the voltage activated channel Slo1, which, by coupling to TRPML1 releases lysosomal $Ca^{2+}$ by positive feedback. (B) Representative G/R images of lysosomes in HEK 293T cells in presence of indicated pharmacological agents (1 μM). Scale=5 μm. (C) Violin plot of lysosomal membrane potential in presence of indicated pharmacological chemicals. (D) Table comparing the changes in $V_{Lys}$ measured by electrophysiology and by Voltair$^{IM}$ when indicated ion channels are inhibited or activated.

Next, the effect of modulating specific channels on the lysosomal membrane was tested. While on the lysosome, the mTORC1 complex inhibits both TPC2 and TRPML1 channels (FIG. 24A). When nutrient levels plummet, mTORC1 dissociates from the lysosome, relieving the inhibition on TPC2 and TRPML1 channels. This triggers lysosomal $Ca^{2+}$ release and is expected to reduce $V_{Lys}$. Low $V_{Lys}$ is expected to activate the voltage dependent channel Slo1, which would promote $K^+$ influx into the lysosome and activate TRPML1. Cytosolic $Ca^{2+}$ elevation caused by TRPML1 channel opening is expected to induce a positive feedback loop to release lysosomal $Ca^{2+}$ and drive further $K^+$ influx.

Figure 25:
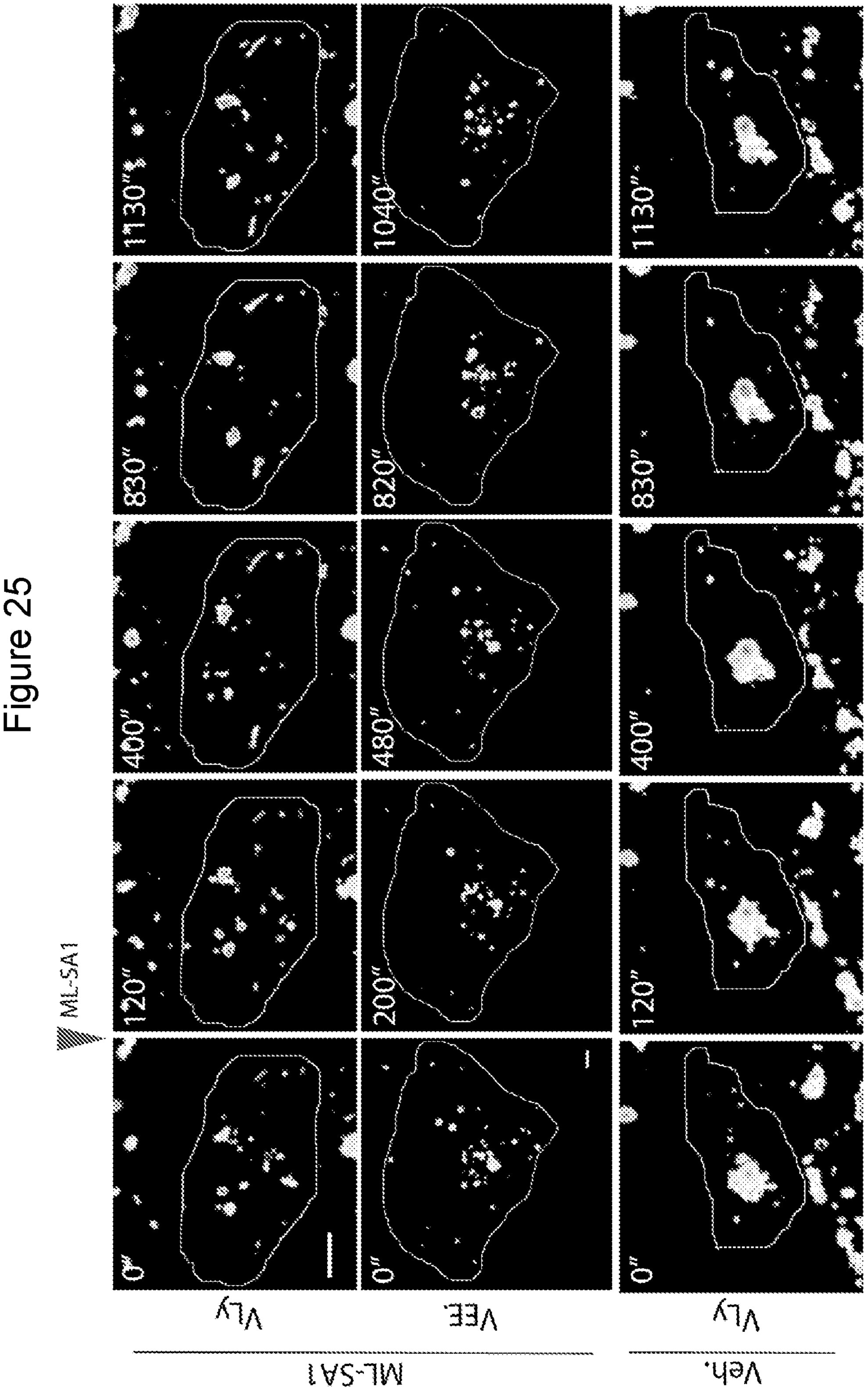
FIG. 25 illustrates representative time lapse images of lysosomal and early endosomal G/R intensity ratios in presence of TRPML1 activator, ML-SA1 at t=100 s (Veh.=DMSO); Images represents the computed intensity ratio of Voltair$^{IM}$ in G (RVF) and R (ATTO™647N) channel. The cell of interest is represented by ROI (region of interest). Scale=10 μm.

Indeed, treating HEK 293T cells with an activator of TRPML1 (ML-SA1, 20 μM) gave a $\Delta V_{Lys}$ of 90 mV using Voltair$^{IM}$ (FIG. 3E, 24B, D). This decrease in membrane potential was specific to the lysosome, because time-lapse imaging of membrane potential in early endosomes ($V_{EE}$) stayed constant upon ML-SA1 treatment, unlike that of lysosomes (FIG. 3F, 25). Treating HEK 293T cells with ML-SA1 as well as the BK channel agonist, NS1619 gave $\Delta V_{Lys}$ of 50 mV (FIG. 3E, 24D). These values are in good agreement with electrophysiological studies that inhibited TRPML1 or activated Slo1. Inhibiting mTORC1 with Torin-1 (1 μM) reduced $V_{Lys}$, by nearly 60 mV from the resting $V_{Lys}$, presumably due to TPC2 and TRPML1 channel activation (FIG. 24B, C). In the presence of Torin-1 and a TPC2 channel inhibitor (trans-ned-19, 1 μM), $V_{Lys}$ was reduced to +80 mV giving $\Delta V_{Lys}$ of 35 mV due to TPC2 channel inhibition (FIG. 24B, C). This is in excellent agreement with analogous measurements by electrophysiology on isolated lysosomes where TPC2 channel inhibition gave $\Delta V_{Lys}$ of 20 mV.

Membrane Potential as a Function of Endosomal Maturation

Figure 4:
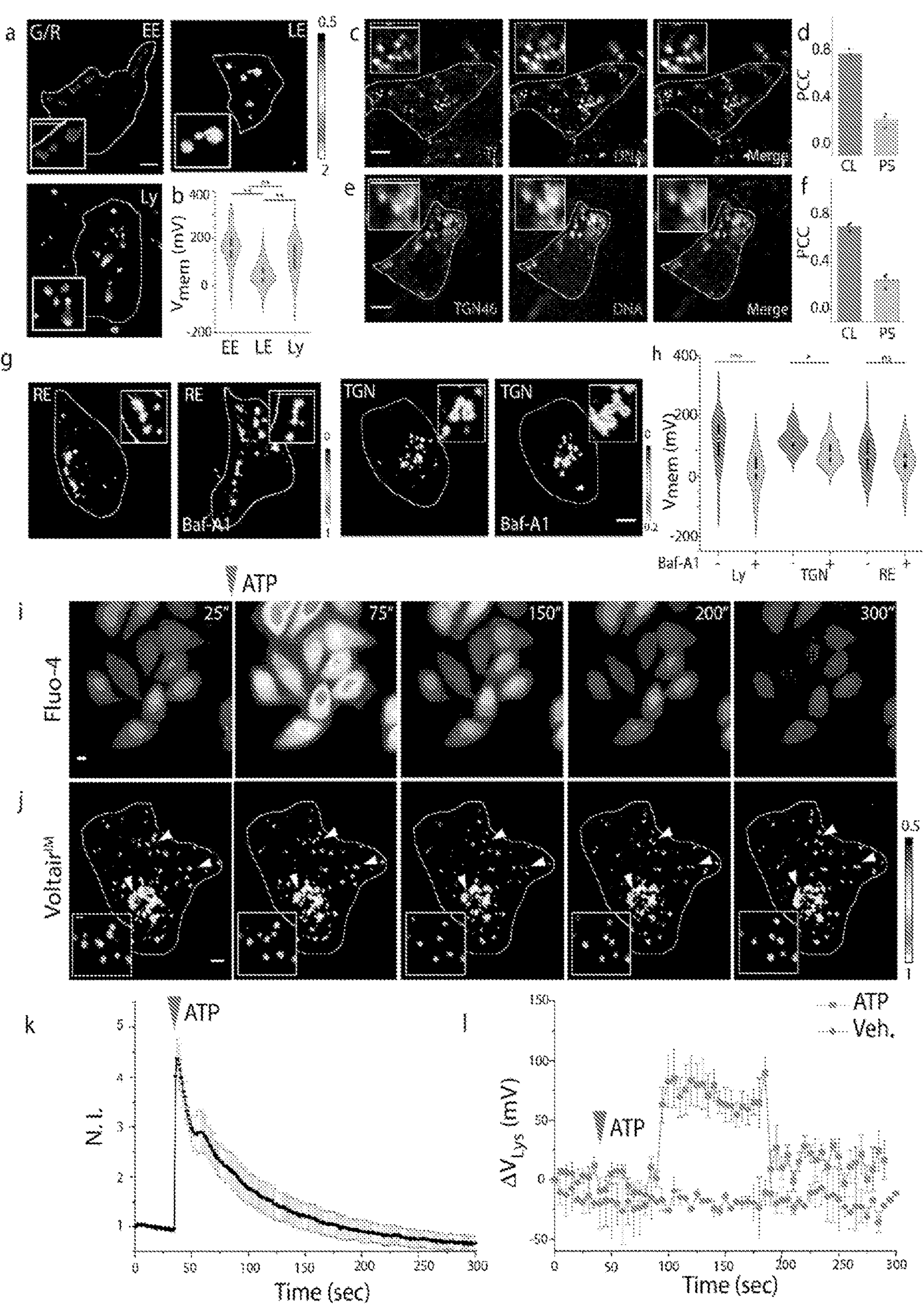
FIG. 4 illustrates membrane potential of organelles along endocytic, recycling and retrograde trafficking pathway. (A) Representative G/R images of the indicated organelles labeled with Voltair$^{IM}$. Scale: 5 μm. (B) Measured membrane potentials of early endosomes (EE), late endosomes (LE) and lysosomes (Ly). Violin plots show kernel smooth distribution, box indicates interquartile range 25-75; Error bars indicate mean±s.d. of 200 vesicles; P<0.01 (one-way ANOVA with Tukey post hoc test). (C) Colocalization between internalized Voltair$^{RE}$ and recycling endosome marker (Transferrin-ALEXA FLUOR®546) in HEK 293T cells. (D) Pearson's correlation coefficient (PCC) of colocalization (CL) and pixel shift (PS) in (C). (E) Colocalization between internalized Voltair$^{TGN}$ and trans-Golgi network marker (TGN46-mCherry) in ScFv-Furin transfected HEK 293T cells. Scale=5 μm, inset=5 μm. (F) Pearson's correlation coefficient (PCC) of colocalization (CL) and pixel shift (PS) in (E). (G) Representative G/R images of RE and TGN of HEK 293T cells in absence and presence of bafilomycin A1 (500 nM). Scale=5 μm. (H) Violin plot of resting membrane potential of organelles and changes upon inhibition of V-ATPase. Box indicates interquartile range 25-75; Error bars indicate mean±s.d; ns, not significant (P>0.05); *P<0.001, *P<0.05 (one-way ANOVA with Tukey post hoc test). (I) Representative time lapse images of ATP induced cytosolic calcium increase imaged using Fluo-4 AM dye. (J) Representative time lapse images of G/R ratio from Voltair$^{IM}$ in presence of 100 μM ATP. (K) Quantification of (I) as a fluorescent intensity vs time plot, error bar represents standard deviation from n=10 cells; Scale=10 μm. (L) Quantification of (J) as a normalized G/R ratio vs time plot, 100 μM ATP treated, Untreated, error bar represents standard deviation from n=6 cells; Scale=10 μm
Figure 26:
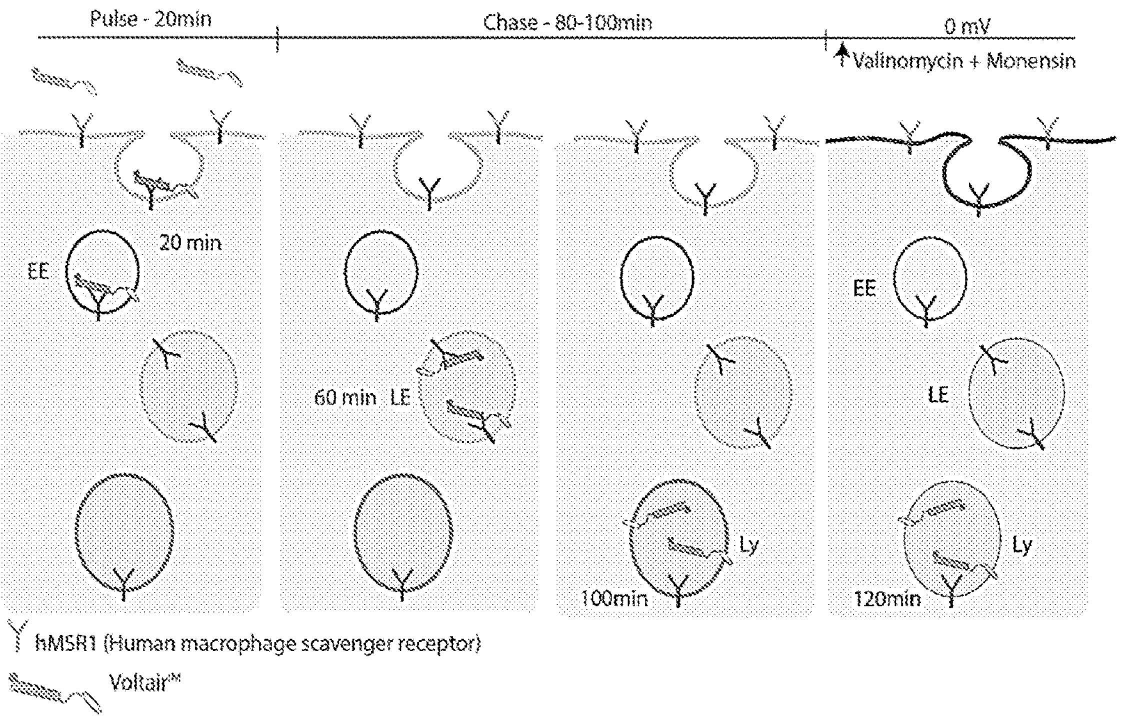
FIG. 26 illustrates schematic representation of pulse-chase protocol for organellar measurements. HEK cells transfected with hMSR-1 were incubated with Voltair$^{IM}$, washed and chased for the indicated chase times to achieve localization in the early endosome (EE), late endosome (LE) and lysosome (Ly) respectively. Images are recorded at indicated chase times. This followed by the addition of a cocktail of valinomycin and monensin to neutralize the membrane potential across all organelles, after which, images are again recorded to obtain the G/R value for 0 mV. G/R values of every organelle are normalized to the G/R value at 0 mV from which organelle membrane potential is quantified.

Encouraged by the accuracy in absolute membrane potential afforded by Voltair in lysosomes, the resting membrane potential of other endocytic organelles was measured as a function of endosomal maturation. Although, the membrane potential of lysosomes has been measured on isolated organelles, no prior values are known for early or late endosomes. Early endosomes, late endosomes and lysosomes were each specifically labelled with Voltair$^{IM}$, as described earlier in FIG. 2D (FIG. 26). The G/R values of ~200 organelles were computed for each endosomal stage and from the intracellular calibration plot it could be determined the corresponding organelle membrane potential (FIG. 4A, B) Measurements with Voltair$^{IM}$ revealed the membrane potential of early endosomes ($V_{EE}$) and late endosomes ($V_{LE}$) to be +153 mV and +46 mV respectively (Table 2). A spread in values of membrane potential in endocytic organelles was observed (FIG. 4B). At least endo-lysosomes are heterogenous and comprise subpopulations that enclose different ionic concentrations. This could in part explain the observed spread in organellar membrane potential.

TABLE 2

Membrane potential values for different endocytic organelles.

| Compartments | Membrane potential (mV)* |
|---|---|
| EE | 153 ± 14 |
| LE | 46 ± 6 |
| Ly | 114 ± 11 |
| RE | 65 ± 14 |
| TGN | 121 ± 18 |

*The error consists of two components, measurement error for G/R and calibration error. Calculation of error is explained above in the Organellar Membrane Potential Measurement section.

Figure 27:
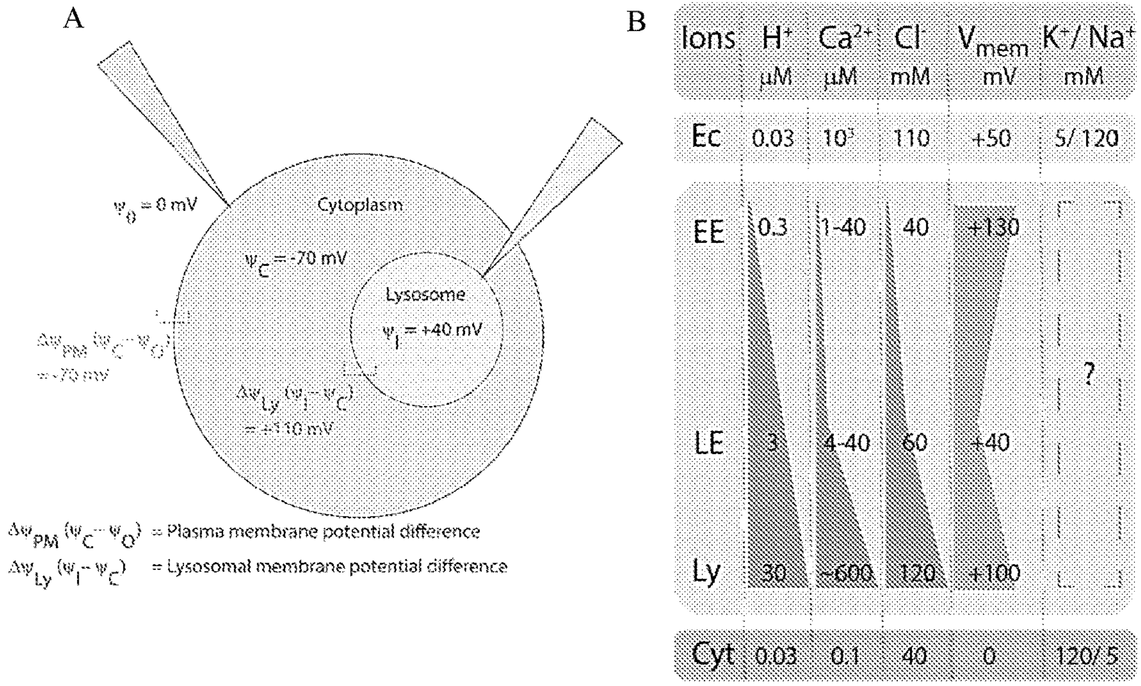
FIG. 27. (A) Schematic showing the convention followed in representing organellar membrane potential. (B) Tabular column summarizing approximate ionic concentration and voltage difference in organelles along the endosomal pathway. Cytosolic (Cyt), extracellular (Ec) and organellar concentrations of main ions that maintain membrane potential.

Surprisingly the gradient of membrane potential accompanying endosomal maturation did not reflect that of ion gradients that have been previously mapped (FIG. 27). The concentrations of protons, chloride and calcium increase progressively during endosomal maturation (FIG. 27). In contrast, membrane potential is highest in the early endosome, drops ~3 fold in the late endosome and increases again in lysosomes. With respect to cytoplasmic concentrations, the levels of lumenal [$Ca^{2+}$] and [$Cl^-$] for the early endosome or the lysosome, are very similar i.e., ~$10^2$-$10^3$ fold higher [$Ca^{2+}$], 1-2-fold higher [$Cl^-$](FIG. 27). However, the lysosome lumen has ~$10^3$ fold higher [$H^+$], while the early endosome lumen has only ~10 fold higher [$H^+$] than the cytosol. Yet the observed membrane potentials for both these organelles are consistent with lower rather than higher membrane potential compared to the early endosome ($V_{EE}$=+153 mV; $V_{LY}$=+114 mV). Considering the low abundances of other free ions, this provides a compelling case for $Na^+$ and $K^+$ transporters or exchangers in maintaining the high positive membrane potential of the early endosome. In fact, late endosomes are posited to contain high $K^+$, which is consistent with the observations. The differences in [$Ca^{2+}$] and [$Cl^-$] across the plasma membrane are comparable, yet its membrane potential is set by the differences in [Na+] and [$K^+$ ] across the membrane.

Membrane Potential of Recycling Endosomes and the Trans Golgi Network

It was then sought to measure membrane potential in organelles that were off the endolysosomal pathway by targeting Voltair to these organelles. Voltair was re-designed to give Voltair$^{RE}$ and Voltair$^{TGN}$ that could access the recycling and retrograde pathways and measure the membrane potential of these respective organelles. Recycling endosomes and the trans-Golgi network have been only hypothesized to have membrane potential which is thought to be regulated by the electrogenic activity of vacuolar $H^+$-ATPases. Voltair$^{RE}$ displays an RNA aptamer against the human transferrin receptor (FIG. 28) and was uptaken by the transferrin receptor pathway. Voltair$^{RE}$ was trafficked to recycling endosomes and evidenced by co-localization with ALEXA FLUOR®546 labelled transferrin (FIG. 4C, D). Voltair$^{TGN}$ was targeted to the trans-Golgi network in HEK 293 cells expressing furin fused to a single-chain variable fragment recombinant antibody, scFv. The scFv domain selectively binds any DNA duplex containing a $d(AT)_4$ sequence. Voltair$^{TGN}$ included a $d(AT)_4$ sequence in the duplex so that the scFv-Furin chimera acts as a carrier protein for the former. Voltair$^{TGN}$ is thus trafficked along the retrograde pathway localizing in the trans Golgi network evidenced by clear colocalization with TGN46-mCherry and absence of colocalization with endocytic organelles (FIG. 4E, F, 29).

The resting membrane potential of the recycling endosome and trans-Golgi network was then measured, neither of which has been previously possible, and evaluated the contribution of V-ATPase to membrane potential in each organelle. Voltair$^{RE}$ labelled cells were imaged in the G and R channels, and G/R values of ~50 recycling endosomes were computed (FIG. 4G, H). It was found that the membrane potential of recycling endosome ($V_{RE}$) was +65 mV (lumen positive), similar to plasma membrane (cytosol negative). When V-ATPase activity was inhibited by treating cells with 500 nM bafilomycin A1, $V_{RE}$ showed no change revealing a negligible contribution of V-ATPase in recycling endosome membranes. The magnitude and the V-ATPase dependence of membrane potential in the recycling endosome mirrors that of the plasma membrane, indicating that both membranes share similar electrical characteristics.

Voltair$^{TGN}$ labelled cells were similarly imaged and G/R values of the TGN in ~30 cells were computed. It was found that the membrane potential of the trans Golgi network ($V_{TGN}$) was +121 mV (lumen positive) (FIG. 4G, H). The high membrane potential of the trans-Golgi network is surprising as the Golgi has been envisaged to have negligible membrane potential, since its high permeability to $K^+$ ions could electrically balance the $H^+$ influx needed to acidify its lumen. In contrast to what was observed for recycling endosomes, V-ATPase inhibition substantially reduced $V_{TGN}$. However, unlike in lysosomes, the membrane potential of the TGN could not be completely neutralized and still showed +75 mV across the membrane. This suggests that other electrogenic transporters at the TGN, possibly Na+/$K^+$ ATPases could significantly contribute to the $V_{TGN}$. It also reveals that different organelle membranes have distinct electrochemical behaviors.

Time Lapse Imaging of Membrane Potential Changes in Lysosomes

Finally, to test the ability of Voltair technology to provide temporal information, the membrane potential of large numbers of intact lysosomes was mapped in situ in response to acute pharmacological triggers. Cytosolic $Ca^{2+}$ levels are stringently regulated by various intracellular organelles such as endoplasmic reticulum, mitochondria and plasma membrane. Lysosomes are also hypothesized to buffer cytosolic $Ca^{2+}$, which, when increased is expected to perturb electrochemical homeostasis of the lysosome. Cytosolic $Ca^{2+}$ was elevated using a physiological trigger such as ATP and measured lysosomal membrane potential along with cytosolic $Ca^{2+}$ levels in COS-7 cells labeled with Voltair$^{IM}$ and Fluo-4-AM. Extracellular ATP increases cytosolic $Ca^{2+}$ by interacting with P2 purinergic receptors on the plasma membrane, generating Ins(1,4,5)$P_3$ or $IP_3$. This activates $IP_3$ receptors on the endoplasmic reticulum, releasing calcium.

Cytosolic $Ca^{2+}$ levels were followed as a function of time by continuously imaging the intensity of Fluo-4 and lysosomal membrane potential by imaging Voltair$^{IM}$ (FIG. 41, J). As expected, cytosolic $Ca^{2+}$ levels reach the maximum ~5 seconds after ATP addition (FIG. 4K). Interestingly, ~80 seconds after maximal cytosolic $Ca^{2+}$ elevation an acute hyperpolarization of the lysosomal membrane was observed by +75 mV. This hyperpolarization lasted for ~100 seconds, before it reverted to normal resting lysosomal membrane potential (FIG. 4J, L). Further, the lysosomal membrane potential is restored when cytosolic $Ca^{2+}$ levels are also restored. The coupling between high cytosolic $Ca^{2+}$ and lysosomal membrane potential, suggests the existence of $Ca^{2+}$-responsive transporters or channels on the lysosomal membrane that modulate membrane potential, possibly through feedback with other ions and lysosomal ion channels e.g., $K^+$ and SLO-1 or $Na^+$ and TPC channels.

CONCLUSION

Protein-based voltage indicators while powerful, have limited applicability to acidic organelles, due to their pH sensitivity and cannot yet provide measures of absolute membrane potential. Voltage sensitive dyes are attractive due to their low capacitive loads and pH insensitivity, but, on their own, cannot be targeted to organelles. Voltair unites the advantages of voltage sensitive dyes with the organelle-targetability of proteins to non-invasively measure the membrane potential of organelles. Voltair nanodevices leverage the 1:1 stoichiometry inherent in DNA duplexes to integrate the following functions with stoichiometric precision: (i) a voltage sensing function using voltage sensitive dyes (ii) an internal reference dye for ratiometric quantitation and (iii) an organelle targeting function for stable organelle localization.

This hybrid, nanoscale DNA-based voltmeter of the disclosure now enables non-invasive, in situ measurement of membrane potential for a range of sub-cellular organelles. For many of these organelles, the endogenous membrane potential was previously unknown. The membrane potential changes that occur during endosomal maturation were now mapped by addressing organelles on the endolysosomal pathway.

Recycling endosomes showed a high similarity with the plasma membrane in terms of the magnitude of the membrane potential as well as its dependence on V-ATPase. The membrane potential of the trans Golgi network, previously hypothesized to be negligible, is revealed to be as high as the lysosome. Yet, unlike the lysosome, it is not completely driven by V-ATPase. Non-invasively interrogating membrane potential in organelles that have proved previously impossible to address, offers the capacity to uncover how these organelles exploit membrane potential to regulate their function.

More broadly, Voltair can function as a quantitative reporter at biotic-abiotic interfaces and can be used to aid the rational design of biocompatible electronics. The inherent three-dimensional nature of biological systems has been predicted to drive the design of open network constructs that can interact with living systems throughout volumes in addition to surfaces. Electrophysiology provides absolute membrane potential, but no spatial information. Voltage indicators provide spatial information but not absolute membrane potential. The capacity of Voltair to provide both allows to model the responses of cells and their organelles to applied electrical stimuli. It could also act as a reporter of organelle damage, because when an organelle membrane breaks, the membrane potential is expected to fall to zero.

While Voltair is not two-photon compatible, it can be redesigned to display two-photon compatible dyes for deep tissue imaging. Unlike genetically encoded voltage reporters, Voltair cannot yet be targeted tissue specifically. Thus, mechanisms to target DNA nanodevices to excitable tissues would significantly expand its applicability; however, DNA nanodevices are preferentially internalized by immune cells in vivo; hence one can readily image organelles in transparent systems such as coelomocytes in nematodes or microglia in zebrafish brains.

When an organelle membrane breaks, the membrane potential is expected to fall to zero. Thus, Voltair may also act as a real-time reporter of organelle damage and membrane repair. As Voltair is a quantitative reporter at the biotic-abiotic interface, it may be used to rationally guide the design of biocompatible electronics.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A nucleic acid complex comprising:

a first single-stranded nucleic acid molecule comprising a voltage-sensing fluorophore crosslinked to the first strand; and a second single-stranded nucleic acid molecule that is partially or fully complementary to the first single-stranded molecule, wherein the nucleic acid complex further comprises a reference label conjugated to the first single-stranded nucleic acid molecule or the second single-stranded nucleic acid molecule and the reference label is capable of producing a signal.

2. The nucleic acid complex of claim 1, further comprising a third single-stranded nucleic acid molecule that is partially complementary to the first single-stranded molecule.

3. The nucleic acid complex of claim 1, wherein the nucleic acid complex further comprises a targeting moiety.

4. The nucleic acid complex of claim 3, wherein the targeting moiety is:

a) a nucleic acid sequence;

b) is encoded on the same nucleic acid strand as the first single-stranded nucleic acid molecule, the second single-stranded nucleic acid molecule, the third single-stranded nucleic acid molecule, or any combination thereof;

c) is encoded in the third single-stranded nucleic acid molecule;

d) is selected from an aptamer, a duplex domain targeted to an artificial protein receptor, a nucleic acid sequence that binds an anionic-ligand binding receptor, and an endocytic ligand;

e) comprises a peptide directly or indirectly conjugated to the nucleic acid molecule;

f) comprises one or more membrane-anchoring groups; or g) comprises one or more of a fusogenic peptide, a membrane-anchoring peptide, a sub-cellular localization sequence, or a cell-receptor ligand.

5. The nucleic acid complex of claim 4, wherein the targeting moiety is the one or more membrane-anchoring groups and the one or more membrane-anchoring groups comprises a 1-palmitoyl-2-oleoyl-sn-glycero-3-phosphoethanolamine (POPE) moiety.

6. The nucleic acid complex of claim 5, wherein the POPE moiety is conjugated to the one or more membrane-anchoring groups through an optional linker a tetra ethylene glycol linker).

7. The nucleic acid complex of claim 1, wherein the voltage-sensing fluorophore comprises a moiety configured to insert into the biological membrane and optionally a spacer moiety; or wherein the voltage-sensing fluorophore is:

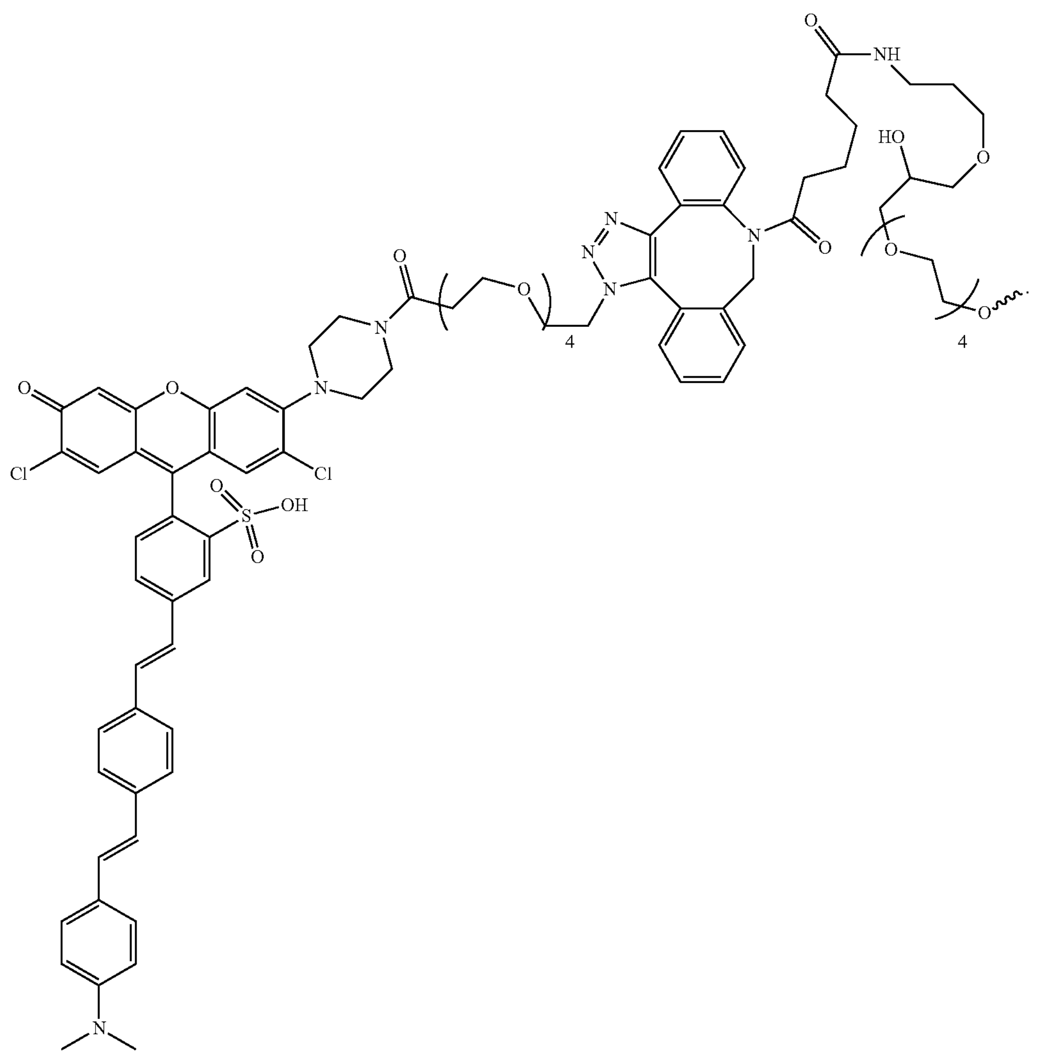

8. The nucleic acid complex of claim 1, wherein the reference label is conjugated to the second single-stranded nucleic acid molecule.

9. The nucleic acid complex of claim 1, wherein the voltage-sensing fluorophore and the reference label are present in 1:0.5 to 0.5:1 stoichiometry or in about 1:1 stoichiometry.

10. The nucleic acid complex of claim 1, wherein the first and/or second single-stranded nucleic acid molecule is less than 200 nucleotides; or less than 100 nucleotides; or less than 50 nucleotides.

11. The nucleic acid complex of claim 2, wherein the nucleic acid complex comprises the first single-stranded nucleic acid molecule having the sequence 5'-AT-CAACACTGCACACCAGACAGCAAGATCC-TATATATA/the voltage-sensing fluorophore/-3' (SEQ ID NO:01), the second single-stranded nucleic acid molecule having the sequence 5'-/the reference label/GGTGTGCAGTGTTGAT-3' (SEQ ID NO:02), and the third single-stranded nucleic acid molecule having the sequence 5'-/membrane-anchoring group/TATATATAG-GATCTTGCTGTCT-3' (SEQ ID NO:04).

12. The nucleic acid complex of claim 1, wherein the first single-stranded nucleic acid molecule has the sequence 5'-ATCAACACTGCACACCAGACAGCAAGATCC-TATATATA/the voltage-sensing fluorophore/-3' (SEQ ID NO:01) and the second single-stranded nucleic acid molecule has the sequence 5'-TATATATAG-GATCTTGCTGTCTGGTGTGCAGTGTTGAT-/the reference label/-3' (SEQ ID NO:03).

13. The nucleic acid complex of claim 2, wherein the first single-stranded nucleic acid molecule has the sequence 5'-/the voltage-sensing fluorophore/-TATATATAG-GATCTTGCTTCTGTGCCTGCAGTGTTGAT-3' (SEQ ID NO: 05), the second single-stranded nucleic acid molecule has the sequence 5'-/the reference label/AT-CAACACTGCAGGCACAGAGTCTGGTG-3' (SEQ ID NO: 06), and the third single-stranded nucleic acid molecule has the sequence 5'-CACCAGACAGCAAGATCC-TATATATAGGGGGAUCAAUCCAAGGGACCCG-GAAACG CUCCCUUACACCCC-3' (SEQ ID NO: 07).

14. A method for determining the membrane potential in a cell comprising:

providing a nucleic acid complex according to claim 1;

measuring the intensity of the signal of the voltage-sensing fluorophore and the signal of the reference probe label, wherein the intensity of the signal of the reference probe label is independent on change in membrane potential; and determining the membrane potential from the measured signals ratiometrically by comparing the intensity of the signal of the voltage-sensing fluorophore and the signal of the reference label.

15. The method of claim 14, wherein the membrane potential is determined in early endosome, late endosome, plasma membrane, lysosome, autophagolysosome, recycling endosome, cis Golgi network, trans Golgi network, endoplasmic reticulum, peroxisomes, or secretory vesicles.

16. The method of claim 14, wherein the intensity of one or both signals varies as a function of at least the orientation of the voltage-sensing fluorophore in or on the membrane.

17. The method of claim 15, wherein the membrane potential is determined in a single organelle or in a plurality of individual organelles.

18. A cell comprising a nucleic acid complex according to claim 1, wherein the nucleic acid complex is conjugated to the cell or to an organellar membrane of the cell.

19. The cell according to claim 18, wherein the nucleic acid complex is reversibly conjugated or irreversibly conjugated to the cell.

* * * * *

SEQUENCE LISTING

<160> NUMBER OF SEQ ID NOS: 9

<210> SEQ ID NO 1
<211> LENGTH: 38
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (38)..(38)
<223> OTHER INFORMATION: 3' voltage-sensing fluorophore.

<400> SEQUENCE: 1
atcaacactg cacaccagac agcaagatcc tatatata 38

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (1)..(1)
<223> OTHER INFORMATION: 5' reference label.

<400> SEQUENCE: 2
ggtgtgcagt gttgat 16

<210> SEQ ID NO 3
<211> LENGTH: 38
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (38)..(38)
<223> OTHER INFORMATION: 3' reference label.

<400> SEQUENCE: 3
tatatatagg atcttgctgt ctggtgtgca gtgttgat 38

<210> SEQ ID NO 4
<211> LENGTH: 22
<212> TYPE: DNA
<213> ORGANISM: Artificial Sequence
<220> FEATURE:

<223> OTHER INFORMATION: Synthetic oligonucleotide.
<220> FEATURE:
<221> NAME/KEY: misc_feature
<222> LOCATION: (1)..(1)
<223> OTHER INFORMATION: 5' membrane-anchoring group.

<400> SEQUENCE: 4
tatatatagg atcttgctgt ct 22

<210> SEQ ID NO 5
<211> LENGTH: 38
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (1)..(1)
<223> OTHER INFORMATION: 5' voltage-sensing fluorophore.

<400> SEQUENCE: 5
tatatatagg atcttgcttc tgtgcctgca gtgttgat 38

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (1)..(1)
<223> OTHER INFORMATION: 5' reference label.

<400> SEQUENCE: 6
atcaacactg caggcacaga gtctggtg 28

<210> SEQ ID NO 7
<211> LENGTH: 69
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (33)..(34)
<223> OTHER INFORMATION: 2' fluoro modified base
<220> FEATURE:
<221> NAME/KEY: misc_feature
<222> LOCATION: (37)..(39)
<223> OTHER INFORMATION: 2' fluoro modified base
<220> FEATURE:
<221> NAME/KEY: misc_feature
<222> LOCATION: (46)..(48)
<223> OTHER INFORMATION: 2' fluoro modified base
<220> FEATURE:
<221> NAME/KEY: misc_feature
<222> LOCATION: (54)..(54)
<223> OTHER INFORMATION: 2' fluoro modified base
<220> FEATURE:
<221> NAME/KEY: misc_feature
<222> LOCATION: (56)..(62)
<223> OTHER INFORMATION: 2' fluoro modified base -continued

```
<220> FEATURE:
<221> NAME/KEY: misc_feature
<222> LOCATION: (64)..(64)
<223> OTHER INFORMATION: 2' fluoro modified base
<220> FEATURE:
<221> NAME/KEY: misc_feature
<222> LOCATION: (66)..(69)
<223> OTHER INFORMATION: 2' fluoro modified base

<400> SEQUENCE: 7

caccagacag caagatccta tatatagggg gaucaaucca agggacccgg aaacgcuccc     60

uuacacccc                                                             69


<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 8

gggacatggg aatgcaatag                                                 20


<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 9

ctcaaggtct gagaatgttc cc                                              22
```